United States Patent
Renner et al.

(10) Patent No.: US 10,799,284 B2
(45) Date of Patent: Oct. 13, 2020

(54) ELECTROSURGICAL INSTRUMENT WITH TEXTURED JAWS

(71) Applicant: Ethicon LLC, Guaynabo, PR (US)

(72) Inventors: Ellen M. Renner, Cincinnati, OH (US); Kevin A. Bash, Cincinnati, OH (US); Joshua M. Basler, Cincinnati, OH (US); Christopher Q. Seow, Fitchburg, WI (US)

(73) Assignee: Ethicon LLC, Guaynabo, PR (US)

( * ) Notice: Subject to any disclaimer, the term of this patent is extended or adjusted under 35 U.S.C. 154(b) by 328 days.

(21) Appl. No.: 15/459,499

(22) Filed: Mar. 15, 2017

(65) Prior Publication Data

US 2018/0263683 A1 Sep. 20, 2018

(51) Int. Cl.
*A61B 18/14* (2006.01)
*A61B 18/12* (2006.01)
*A61B 18/00* (2006.01)

(52) U.S. Cl.
CPC ........... *A61B 18/1445* (2013.01); *A61B 2018/00083* (2013.01); *A61B 2018/00589* (2013.01);
(Continued)

(58) Field of Classification Search
CPC ............ A61B 18/1445; A61B 18/1442; A61B 2018/1455; A61B 2018/00607
See application file for complete search history.

(56) References Cited

U.S. PATENT DOCUMENTS 2,366,274 A 1/1945 Luth et al.
2,458,152 A 1/1949 Eakins
(Continued)

FOREIGN PATENT DOCUMENTS

CN 1634601 A 7/2005
CN 1922563 A 2/2007
(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
(Continued)

*Primary Examiner* — Michael F Peffley
*Assistant Examiner* — Bo Ouyang

(57) ABSTRACT

An electrosurgical system includes an RF current generator, a handle body, and an end effector in mechanical communication with the handle body. The end effector has a first jaw including a first electrode having a first electrode surface in electrical communication with a first terminal of the generator. The end effector also includes a second jaw including a second electrode having an essentially planar second electrode surface in electrical communication with a second terminal of the generator The first jaw includes at least one feature configured to apply an amount of a compressive force to a tissue compressed between the at least one feature and the second electrode surface that differs from an amount of a compressive force applied to the tissue compressed between the first electrode surface and the second electrode surface when the first jaw is placed in a proximate position to the second jaw.

22 Claims, 29 Drawing Sheets

(52) U.S. Cl.
CPC ........... *A61B 2018/00607* (2013.01); *A61B 2018/00642* (2013.01); *A61B 2018/00666* (2013.01); *A61B 2018/00702* (2013.01); *A61B 2018/00767* (2013.01); *A61B 2018/00827* (2013.01); *A61B 2018/126* (2013.01); *A61B 2018/1455* (2013.01)

(56) References Cited

U.S. PATENT DOCUMENTS

| | | |
|---|---|---|
| 2,510,693 A | 6/1950 | Green |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,633,874 A | 1/1987 | Chow et al. |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,188,102 A | 2/1993 | Idemoto et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |
| 5,254,130 A | 10/1993 | Poncet et al. |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,293,863 A | 3/1994 | Zhu et al. |
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |

(56) References Cited

U.S. PATENT DOCUMENTS

| | | |
|---|---|---|
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,741,305 A | 4/1998 | Vincent et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |

(56) References Cited

U.S. PATENT DOCUMENTS

| | | | |
|---|---|---|---|
| 5,836,943 A | 11/1998 | Miller, III | |
| 5,836,990 A | 11/1998 | Li | |
| 5,843,109 A | 12/1998 | Mehta et al. | |
| 5,853,412 A | 12/1998 | Mayenberger | |
| 5,876,401 A | 3/1999 | Schulze et al. | |
| 5,878,193 A | 3/1999 | Wang et al. | |
| 5,879,364 A | 3/1999 | Bromfield et al. | |
| 5,880,668 A | 3/1999 | Hall | |
| 5,883,454 A | 3/1999 | Hones et al. | |
| 5,887,018 A | 3/1999 | Bayazitoglu et al. | |
| 5,891,142 A * | 4/1999 | Eggers | A61B 18/1442 606/51 |
| 5,893,835 A | 4/1999 | Witt et al. | |
| 5,897,569 A | 4/1999 | Kellogg et al. | |
| 5,902,239 A | 5/1999 | Buurman | |
| 5,904,147 A | 5/1999 | Conlan et al. | |
| 5,906,579 A | 5/1999 | Vander Salm et al. | |
| 5,906,625 A | 5/1999 | Bito et al. | |
| 5,910,129 A | 6/1999 | Koblish et al. | |
| 5,921,956 A | 7/1999 | Grinberg et al. | |
| 5,929,846 A | 7/1999 | Rosenberg et al. | |
| 5,935,143 A | 8/1999 | Hood | |
| 5,935,144 A | 8/1999 | Estabrook | |
| 5,938,633 A | 8/1999 | Beaupre | |
| 5,944,298 A | 8/1999 | Koike | |
| 5,944,718 A | 8/1999 | Austin et al. | |
| 5,944,737 A | 8/1999 | Tsonton et al. | |
| 5,954,736 A | 9/1999 | Bishop et al. | |
| 5,954,746 A | 9/1999 | Holthaus et al. | |
| 5,957,849 A | 9/1999 | Munro | |
| 5,957,882 A | 9/1999 | Nita et al. | |
| 5,957,943 A | 9/1999 | Vaitekunas | |
| 5,968,007 A | 10/1999 | Simon et al. | |
| 5,968,060 A | 10/1999 | Kellogg | |
| D416,089 S | 11/1999 | Barton et al. | |
| 5,984,938 A | 11/1999 | Yoon | |
| 5,989,182 A | 11/1999 | Hori et al. | |
| 5,989,274 A | 11/1999 | Davison et al. | |
| 5,989,275 A | 11/1999 | Estabrook et al. | |
| 5,993,972 A | 11/1999 | Reich et al. | |
| 6,003,517 A | 12/1999 | Sheffield et al. | |
| 6,007,484 A | 12/1999 | Thompson | |
| 6,013,052 A | 1/2000 | Durman et al. | |
| 6,014,580 A | 1/2000 | Blume et al. | |
| 6,024,741 A | 2/2000 | Williamson, IV et al. | |
| 6,024,744 A | 2/2000 | Kese et al. | |
| 6,033,375 A | 3/2000 | Brumbach | |
| 6,033,399 A | 3/2000 | Gines | |
| 6,039,734 A | 3/2000 | Goble | |
| 6,050,996 A | 4/2000 | Schmaltz et al. | |
| 6,053,172 A | 4/2000 | Hovda et al. | |
| 6,063,098 A | 5/2000 | Houser et al. | |
| 6,066,132 A | 5/2000 | Chen et al. | |
| 6,068,629 A | 5/2000 | Haissaguerre et al. | |
| 6,068,647 A | 5/2000 | Witt et al. | |
| 6,074,389 A | 6/2000 | Levine et al. | |
| 6,077,285 A | 6/2000 | Boukhny | |
| 6,080,152 A | 6/2000 | Nardella et al. | |
| 6,083,151 A | 7/2000 | Renner et al. | |
| 6,083,191 A | 7/2000 | Rose | |
| 6,086,584 A | 7/2000 | Miller | |
| 6,090,120 A | 7/2000 | Wright et al. | |
| 6,091,995 A | 7/2000 | Ingle et al. | |
| 6,099,483 A | 8/2000 | Palmer et al. | |
| 6,099,550 A | 8/2000 | Yoon | |
| 6,109,500 A | 8/2000 | Alli et al. | |
| 6,113,594 A | 9/2000 | Savage | |
| 6,113,598 A | 9/2000 | Baker | |
| 6,123,466 A | 9/2000 | Persson et al. | |
| H1904 H | 10/2000 | Yates et al. | |
| 6,127,757 A | 10/2000 | Swinbanks | |
| 6,132,368 A | 10/2000 | Cooper | |
| 6,139,320 A | 10/2000 | Hahn | |
| 6,144,402 A | 11/2000 | Norsworthy et al. | |
| 6,152,902 A | 11/2000 | Christian et al. | |
| 6,152,923 A | 11/2000 | Ryan | |
| 6,154,198 A | 11/2000 | Rosenberg | |
| 6,159,160 A | 12/2000 | Hsei et al. | |
| 6,159,175 A | 12/2000 | Strukel et al. | |
| 6,162,208 A | 12/2000 | Hipps | |
| 6,173,199 B1 | 1/2001 | Gabriel | |
| 6,173,715 B1 | 1/2001 | Sinanan et al. | |
| 6,174,309 B1 | 1/2001 | Wrublewski et al. | |
| 6,176,857 B1 | 1/2001 | Ashley | |
| 6,190,386 B1 | 2/2001 | Rydell | |
| 6,206,844 B1 | 3/2001 | Reichel et al. | |
| 6,206,876 B1 | 3/2001 | Levine et al. | |
| 6,206,877 B1 | 3/2001 | Kese et al. | |
| 6,210,403 B1 | 4/2001 | Klicek | |
| 6,214,023 B1 | 4/2001 | Whipple et al. | |
| 6,219,572 B1 | 4/2001 | Young | |
| 6,221,007 B1 | 4/2001 | Green | |
| 6,228,080 B1 | 5/2001 | Gines | |
| 6,231,565 B1 | 5/2001 | Tovey et al. | |
| 6,233,476 B1 | 5/2001 | Strommer et al. | |
| 6,238,366 B1 | 5/2001 | Savage et al. | |
| 6,241,724 B1 | 6/2001 | Fleischman et al. | |
| 6,248,074 B1 | 6/2001 | Ohno et al. | |
| D444,365 S | 7/2001 | Bass et al. | |
| 6,254,623 B1 | 7/2001 | Haibel, Jr. et al. | |
| 6,258,034 B1 | 7/2001 | Hanafy | |
| 6,258,086 B1 | 7/2001 | Ashley et al. | |
| 6,259,230 B1 | 7/2001 | Chou | |
| 6,267,761 B1 | 7/2001 | Ryan | |
| 6,270,831 B2 | 8/2001 | Kumar et al. | |
| 6,273,852 B1 | 8/2001 | Lehe et al. | |
| 6,273,887 B1 | 8/2001 | Yamauchi et al. | |
| 6,274,963 B1 | 8/2001 | Estabrook et al. | |
| 6,277,115 B1 | 8/2001 | Saadat | |
| 6,277,117 B1 | 8/2001 | Tetzlaff et al. | |
| 6,278,218 B1 | 8/2001 | Madan et al. | |
| 6,283,981 B1 | 9/2001 | Beaupre | |
| 6,292,700 B1 | 9/2001 | Morrison et al. | |
| 6,309,400 B2 | 10/2001 | Beaupre | |
| 6,315,789 B1 | 11/2001 | Cragg | |
| 6,319,221 B1 | 11/2001 | Savage et al. | |
| 6,325,799 B1 | 12/2001 | Goble | |
| 6,325,811 B1 | 12/2001 | Messerly | |
| 6,328,751 B1 | 12/2001 | Beaupre | |
| 6,340,878 B1 | 1/2002 | Oglesbee | |
| 6,352,532 B1 | 3/2002 | Kramer et al. | |
| 6,364,888 B1 | 4/2002 | Niemeyer et al. | |
| 6,371,952 B1 | 4/2002 | Madhani et al. | |
| 6,379,320 B1 | 4/2002 | Lafon et al. | |
| D457,958 S | 5/2002 | Dycus et al. | |
| 6,383,194 B1 | 5/2002 | Pothula | |
| 6,387,094 B1 | 5/2002 | Eitenmuller | |
| 6,387,109 B1 | 5/2002 | Davison et al. | |
| 6,388,657 B1 | 5/2002 | Natoli | |
| 6,391,026 B1 | 5/2002 | Hung et al. | |
| 6,391,042 B1 | 5/2002 | Cimino | |
| 6,398,779 B1 | 6/2002 | Buysse et al. | |
| 6,409,722 B1 | 6/2002 | Hoey et al. | |
| H2037 H | 7/2002 | Yates et al. | |
| 6,416,469 B1 | 7/2002 | Phung et al. | |
| 6,416,486 B1 | 7/2002 | Wampler | |
| 6,419,675 B1 | 7/2002 | Gallo, Sr. | |
| 6,423,073 B2 | 7/2002 | Bowman | |
| 6,423,082 B1 | 7/2002 | Houser et al. | |
| 6,430,446 B1 | 8/2002 | Knowlton | |
| 6,432,118 B1 | 8/2002 | Messerly | |
| 6,436,114 B1 | 8/2002 | Novak et al. | |
| 6,436,115 B1 | 8/2002 | Beaupre | |
| 6,443,968 B1 | 9/2002 | Holthaus et al. | |
| 6,443,969 B1 | 9/2002 | Novak et al. | |
| 6,454,781 B1 | 9/2002 | Witt et al. | |
| 6,454,782 B1 | 9/2002 | Schwemberger | |
| 6,458,128 B1 | 10/2002 | Schulze | |
| 6,458,130 B1 | 10/2002 | Frazier et al. | |
| 6,458,142 B1 | 10/2002 | Faller et al. | |
| 6,461,363 B1 | 10/2002 | Gadberry et al. | |
| 6,464,689 B1 | 10/2002 | Qin et al. | |
| 6,464,702 B2 | 10/2002 | Schulze et al. | |
| 6,464,703 B2 | 10/2002 | Bartel | |

(56) References Cited

U.S. PATENT DOCUMENTS

| | | | |
|---|---|---|---|
| 6,471,172 B1 | 10/2002 | Lemke et al. |
| 6,475,211 B2 | 11/2002 | Chess et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Sater |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |

(56) References Cited

U.S. PATENT DOCUMENTS

| | | |
|---|---|---|
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |
| 7,479,160 B2 | 1/2009 | Branch et al. |
| 7,487,899 B2 | 2/2009 | Shelton, IV et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |

(56) References Cited

U.S. PATENT DOCUMENTS

| | | | |
|---|---|---|---|
| 7,553,309 | B2 | 6/2009 | Buysse et al. |
| 7,559,452 | B2 | 7/2009 | Wales et al. |
| 7,566,318 | B2 | 7/2009 | Haefner |
| 7,567,012 | B2 | 7/2009 | Namikawa |
| 7,582,086 | B2 | 9/2009 | Privitera et al. |
| 7,582,087 | B2 | 9/2009 | Tetzlaff et al. |
| 7,586,289 | B2 | 9/2009 | Andruk et al. |
| 7,588,176 | B2 | 9/2009 | Timm et al. |
| 7,588,177 | B2 | 9/2009 | Racenet |
| 7,594,925 | B2 | 9/2009 | Danek et al. |
| 7,597,693 | B2 | 10/2009 | Garrison |
| 7,599,743 | B2 | 10/2009 | Hassler, Jr. et al. |
| 7,601,119 | B2 | 10/2009 | Shahinian |
| 7,604,150 | B2 | 10/2009 | Boudreaux |
| 7,611,512 | B2 | 11/2009 | Ein-Gal |
| 7,617,961 | B2 | 11/2009 | Viola |
| 7,621,910 | B2 | 11/2009 | Sugi |
| 7,621,930 | B2 | 11/2009 | Houser |
| 7,625,370 | B2 | 12/2009 | Hart et al. |
| 7,628,791 | B2 | 12/2009 | Garrison et al. |
| 7,628,792 | B2 | 12/2009 | Guerra |
| 7,632,267 | B2 | 12/2009 | Dahla |
| 7,632,269 | B2 | 12/2009 | Truckai et al. |
| 7,637,410 | B2 | 12/2009 | Marczyk |
| 7,640,447 | B2 | 12/2009 | Qiu |
| 7,641,653 | B2 | 1/2010 | Dalla Betta et al. |
| 7,641,671 | B2 | 1/2010 | Crainich |
| 7,644,848 | B2 | 1/2010 | Swayze et al. |
| 7,645,277 | B2 | 1/2010 | McClurken et al. |
| 7,648,499 | B2 | 1/2010 | Orszulak et al. |
| 7,658,311 | B2 | 2/2010 | Boudreaux |
| 7,662,151 | B2 | 2/2010 | Crompton, Jr. et al. |
| 7,665,647 | B2 | 2/2010 | Shelton, IV et al. |
| 7,666,206 | B2 | 2/2010 | Taniguchi et al. |
| 7,670,334 | B2 | 3/2010 | Hueil et al. |
| 7,678,043 | B2 | 3/2010 | Gilad |
| 7,678,105 | B2 | 3/2010 | McGreevy et al. |
| 7,686,804 | B2 | 3/2010 | Johnson et al. |
| 7,691,095 | B2 | 4/2010 | Bednarek et al. |
| 7,691,098 | B2 | 4/2010 | Wallace et al. |
| 7,691,103 | B2 | 4/2010 | Fernandez et al. |
| 7,703,459 | B2 | 4/2010 | Saadat et al. |
| 7,703,653 | B2 | 4/2010 | Shah et al. |
| 7,708,735 | B2 | 5/2010 | Chapman et al. |
| 7,708,751 | B2 | 5/2010 | Hughes et al. |
| 7,708,758 | B2 | 5/2010 | Lee et al. |
| 7,717,312 | B2 | 5/2010 | Beetel |
| 7,717,914 | B2 | 5/2010 | Kimura |
| 7,717,915 | B2 | 5/2010 | Miyazawa |
| 7,722,527 | B2 | 5/2010 | Bouchier et al. |
| 7,722,607 | B2 | 5/2010 | Dumbauld et al. |
| 7,725,214 | B2 | 5/2010 | Diolaiti |
| D618,797 | S | 6/2010 | Price et al. |
| 7,726,537 | B2 | 6/2010 | Olson et al. |
| 7,744,615 | B2 | 6/2010 | Couture |
| 7,751,115 | B2 | 7/2010 | Song |
| 7,753,904 | B2 | 7/2010 | Shelton, IV et al. |
| 7,753,908 | B2 | 7/2010 | Swanson |
| 7,753,909 | B2 | 7/2010 | Chapman et al. |
| 7,762,445 | B2 | 7/2010 | Heinrich et al. |
| D621,503 | S | 8/2010 | Otten et al. |
| 7,766,210 | B2 | 8/2010 | Shelton, IV et al. |
| 7,766,910 | B2 | 8/2010 | Hixson et al. |
| 7,770,774 | B2 | 8/2010 | Mastri et al. |
| 7,770,775 | B2 | 8/2010 | Shelton, IV et al. |
| 7,775,972 | B2 | 8/2010 | Brock et al. |
| 7,776,036 | B2 | 8/2010 | Schechter et al. |
| 7,776,037 | B2 | 8/2010 | Odom |
| 7,780,651 | B2 | 8/2010 | Madhani et al. |
| 7,780,659 | B2 | 8/2010 | Okada et al. |
| 7,780,663 | B2 | 8/2010 | Yates et al. |
| 7,784,663 | B2 | 8/2010 | Shelton, IV |
| 7,789,283 | B2 | 9/2010 | Shah |
| 7,789,878 | B2 | 9/2010 | Dumbauld et al. |
| 7,789,883 | B2 | 9/2010 | Takashino et al. |
| 7,793,814 | B2 | 9/2010 | Racenet et al. |
| 7,799,027 | B2 | 9/2010 | Hafner |
| 7,803,156 | B2 | 9/2010 | Eder et al. |
| 7,806,891 | B2 | 10/2010 | Nowlin et al. |
| 7,810,692 | B2 | 10/2010 | Hall et al. |
| 7,810,693 | B2 | 10/2010 | Broehl et al. |
| 7,815,641 | B2 | 10/2010 | Dodde et al. |
| 7,819,298 | B2 | 10/2010 | Hall et al. |
| 7,819,299 | B2 | 10/2010 | Shelton, IV et al. |
| 7,819,872 | B2 | 10/2010 | Johnson et al. |
| D627,066 | S | 11/2010 | Romero |
| 7,824,401 | B2 | 11/2010 | Manzo et al. |
| 7,832,408 | B2 | 11/2010 | Shelton, IV et al. |
| 7,832,612 | B2 | 11/2010 | Baxter, III et al. |
| 7,837,699 | B2 | 11/2010 | Yamada et al. |
| 7,845,537 | B2 | 12/2010 | Shelton, IV et al. |
| 7,846,159 | B2 | 12/2010 | Morrison et al. |
| 7,846,160 | B2 | 12/2010 | Payne et al. |
| 7,850,688 | B2 | 12/2010 | Hafner |
| D631,155 | S | 1/2011 | Peine et al. |
| 7,861,906 | B2 | 1/2011 | Doll et al. |
| 7,862,560 | B2 | 1/2011 | Marion |
| 7,867,228 | B2 | 1/2011 | Nobis et al. |
| 7,871,392 | B2 | 1/2011 | Sartor |
| 7,871,423 | B2 | 1/2011 | Livneh |
| D631,965 | S | 2/2011 | Price et al. |
| 7,877,852 | B2 | 2/2011 | Unger et al. |
| 7,877,853 | B2 | 2/2011 | Unger et al. |
| 7,879,035 | B2 | 2/2011 | Garrison et al. |
| 7,879,070 | B2 | 2/2011 | Ortiz et al. |
| 7,892,606 | B2 | 2/2011 | Thies et al. |
| 7,896,875 | B2 | 3/2011 | Heim et al. |
| 7,896,878 | B2 | 3/2011 | Johnson et al. |
| 7,901,400 | B2 | 3/2011 | Wham et al. |
| 7,901,423 | B2 | 3/2011 | Stulen et al. |
| 7,905,881 | B2 | 3/2011 | Masuda et al. |
| 7,909,220 | B2 | 3/2011 | Viola |
| 7,919,184 | B2 | 4/2011 | Mohapatra et al. |
| 7,922,061 | B2 | 4/2011 | Shelton, IV et al. |
| 7,922,651 | B2 | 4/2011 | Yamada et al. |
| 7,922,953 | B2 | 4/2011 | Guerra |
| 7,931,649 | B2 | 4/2011 | Couture et al. |
| D637,288 | S | 5/2011 | Houghton |
| D638,540 | S | 5/2011 | Ijiri et al. |
| 7,935,114 | B2 | 5/2011 | Takashino et al. |
| 7,942,303 | B2 | 5/2011 | Shah |
| 7,942,868 | B2 | 5/2011 | Cooper |
| 7,951,165 | B2 | 5/2011 | Golden et al. |
| 7,955,331 | B2 | 6/2011 | Truckai et al. |
| 7,959,050 | B2 | 6/2011 | Smith et al. |
| 7,959,626 | B2 | 6/2011 | Hong et al. |
| 7,963,963 | B2 | 6/2011 | Francischelli et al. |
| 7,967,602 | B2 | 6/2011 | Lindquist |
| 7,976,544 | B2 | 7/2011 | McClurken et al. |
| 7,980,443 | B2 | 7/2011 | Scheib et al. |
| 7,981,113 | B2 | 7/2011 | Truckai et al. |
| 7,988,567 | B2 | 8/2011 | Kim et al. |
| 7,997,278 | B2 | 8/2011 | Utley et al. |
| 8,020,743 | B2 | 9/2011 | Shelton, IV |
| 8,033,173 | B2 | 10/2011 | Ehlert et al. |
| 8,038,612 | B2 | 10/2011 | Paz |
| 8,038,693 | B2 | 10/2011 | Allen |
| 8,048,070 | B2 | 11/2011 | O'Brien et al. |
| 8,052,672 | B2 | 11/2011 | Laufer et al. |
| 8,056,720 | B2 | 11/2011 | Hawkes |
| 8,056,787 | B2 | 11/2011 | Boudreaux et al. |
| 8,057,498 | B2 | 11/2011 | Robertson |
| 8,058,771 | B2 | 11/2011 | Giordano et al. |
| 8,061,014 | B2 | 11/2011 | Smith et al. |
| 8,062,211 | B2 | 11/2011 | Duval et al. |
| 8,066,167 | B2 | 11/2011 | Measamer et al. |
| 8,070,036 | B1 | 12/2011 | Knodel |
| 8,070,748 | B2 | 12/2011 | Hixson et al. |
| 8,075,555 | B2 | 12/2011 | Truckai et al. |
| 8,075,558 | B2 | 12/2011 | Truckai et al. |
| 8,092,475 | B2 | 1/2012 | Cotter et al. |
| 8,100,894 | B2 | 1/2012 | Mucko et al. |
| 8,105,323 | B2 | 1/2012 | Buysse et al. |
| 8,105,324 | B2 | 1/2012 | Palanker et al. |

(56) References Cited

U.S. PATENT DOCUMENTS

| | | |
|---|---|---|
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Horner |
| 8,496,682 B2 | 7/2013 | Guerra et al. |
| 8,512,336 B2 | 8/2013 | Couture |
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |

(56) References Cited

U.S. PATENT DOCUMENTS

| | | | |
|---|---|---|---|
| 8,579,937 | B2 | 11/2013 | Gresham |
| 8,591,459 | B2 | 11/2013 | Clymer et al. |
| 8,591,506 | B2 | 11/2013 | Wham et al. |
| D695,407 | S | 12/2013 | Price et al. |
| 8,596,513 | B2 | 12/2013 | Olson et al. |
| 8,597,182 | B2 | 12/2013 | Stein et al. |
| 8,597,297 | B2 | 12/2013 | Couture et al. |
| 8,608,044 | B2 | 12/2013 | Hueil et al. |
| 8,613,383 | B2 | 12/2013 | Beckman et al. |
| 8,622,274 | B2 | 1/2014 | Yates et al. |
| 8,623,011 | B2 | 1/2014 | Spivey |
| 8,623,016 | B2 | 1/2014 | Fischer |
| 8,623,027 | B2 | 1/2014 | Price et al. |
| 8,623,044 | B2 | 1/2014 | Timm et al. |
| 8,628,529 | B2 | 1/2014 | Aldridge et al. |
| 8,632,461 | B2 | 1/2014 | Glossop |
| 8,632,539 | B2 | 1/2014 | Twomey et al. |
| 8,636,648 | B2 | 1/2014 | Gazdzinski |
| 8,636,736 | B2 | 1/2014 | Yates et al. |
| 8,636,761 | B2 | 1/2014 | Cunningham et al. |
| 8,638,428 | B2 | 1/2014 | Brown |
| 8,640,788 | B2 | 2/2014 | Dachs, II et al. |
| 8,641,712 | B2 | 2/2014 | Couture |
| 8,647,350 | B2 | 2/2014 | Mohan et al. |
| 8,650,728 | B2 | 2/2014 | Wan et al. |
| 8,652,120 | B2 | 2/2014 | Giordano et al. |
| 8,652,155 | B2 | 2/2014 | Houser et al. |
| 8,663,220 | B2 | 3/2014 | Wiener et al. |
| 8,663,222 | B2 | 3/2014 | Anderson et al. |
| 8,663,223 | B2 | 3/2014 | Masuda et al. |
| 8,668,691 | B2 | 3/2014 | Heard |
| RE44,834 | E | 4/2014 | Dumbauld et al. |
| 8,684,253 | B2 | 4/2014 | Giordano et al. |
| 8,685,020 | B2 | 4/2014 | Weizman et al. |
| 8,685,056 | B2 | 4/2014 | Evans et al. |
| 8,696,662 | B2 | 4/2014 | Eder et al. |
| 8,696,665 | B2 | 4/2014 | Hunt et al. |
| 8,702,609 | B2 | 4/2014 | Hadjicostis |
| 8,702,704 | B2 | 4/2014 | Shelton, IV et al. |
| 8,708,213 | B2 | 4/2014 | Shelton, IV et al. |
| 8,709,035 | B2 | 4/2014 | Johnson et al. |
| 8,715,270 | B2 | 5/2014 | Weitzner et al. |
| 8,715,277 | B2 | 5/2014 | Weizman |
| 8,721,640 | B2 | 5/2014 | Taylor et al. |
| 8,734,443 | B2 | 5/2014 | Hixson et al. |
| 8,747,238 | B2 | 6/2014 | Shelton, IV et al. |
| 8,747,351 | B2 | 6/2014 | Schultz |
| 8,747,404 | B2 | 6/2014 | Boudreaux et al. |
| 8,752,264 | B2 | 6/2014 | Ackley et al. |
| 8,752,749 | B2 | 6/2014 | Moore et al. |
| 8,753,338 | B2 | 6/2014 | Widenhouse et al. |
| 8,758,342 | B2 | 6/2014 | Bales et al. |
| 8,764,747 | B2 | 7/2014 | Cummings et al. |
| 8,770,459 | B2 | 7/2014 | Racenet et al. |
| 8,784,418 | B2 | 7/2014 | Romero |
| 8,789,740 | B2 | 7/2014 | Baxter, III et al. |
| 8,790,342 | B2 | 7/2014 | Stulen et al. |
| 8,795,274 | B2 | 8/2014 | Hanna |
| 8,795,276 | B2 | 8/2014 | Dietz et al. |
| 8,795,327 | B2 | 8/2014 | Dietz et al. |
| 8,800,838 | B2 | 8/2014 | Shelton, IV |
| 8,801,752 | B2 | 8/2014 | Fortier et al. |
| 8,808,319 | B2 | 8/2014 | Houser et al. |
| 8,814,856 | B2 | 8/2014 | Elmouelhi et al. |
| 8,814,865 | B2 | 8/2014 | Reschke |
| 8,814,870 | B2 | 8/2014 | Paraschiv et al. |
| 8,827,992 | B2 | 9/2014 | Koss et al. |
| 8,827,995 | B2 | 9/2014 | Schaller et al. |
| 8,834,466 | B2 | 9/2014 | Cummings et al. |
| 8,834,488 | B2 | 9/2014 | Farritor et al. |
| 8,834,518 | B2 | 9/2014 | Faller et al. |
| 8,845,630 | B2 | 9/2014 | Mehta et al. |
| 8,851,354 | B2 | 10/2014 | Swensgard et al. |
| 8,852,184 | B2 | 10/2014 | Kucklick |
| 8,864,757 | B2 | 10/2014 | Klimovitch et al. |
| 8,864,761 | B2 | 10/2014 | Johnson et al. |
| 8,870,867 | B2 | 10/2014 | Walberg et al. |
| 8,876,858 | B2 | 11/2014 | Braun |
| 8,882,766 | B2 | 11/2014 | Couture et al. |
| 8,882,791 | B2 | 11/2014 | Stulen |
| 8,888,776 | B2 | 11/2014 | Dietz et al. |
| 8,888,783 | B2 | 11/2014 | Young |
| 8,888,809 | B2 | 11/2014 | Davison et al. |
| 8,906,016 | B2 | 12/2014 | Boudreaux et al. |
| 8,906,017 | B2 | 12/2014 | Rioux et al. |
| 8,911,438 | B2 | 12/2014 | Swoyer et al. |
| 8,911,460 | B2 | 12/2014 | Neurohr et al. |
| 8,926,607 | B2 | 1/2015 | Norvell et al. |
| 8,926,608 | B2 | 1/2015 | Bacher et al. |
| 8,929,888 | B2 | 1/2015 | Rao et al. |
| 8,931,682 | B2 | 1/2015 | Timm et al. |
| 8,939,287 | B2 | 1/2015 | Markovitch |
| 8,939,974 | B2 | 1/2015 | Boudreaux et al. |
| 8,939,975 | B2 | 1/2015 | Twomey et al. |
| 8,944,997 | B2 | 2/2015 | Fernandez et al. |
| 8,945,125 | B2 | 2/2015 | Schechter et al. |
| 8,951,248 | B2 | 2/2015 | Messerly et al. |
| 8,951,272 | B2 | 2/2015 | Robertson et al. |
| 8,956,349 | B2 | 2/2015 | Aldridge et al. |
| 8,960,520 | B2 | 2/2015 | McCuen |
| 8,961,515 | B2 | 2/2015 | Twomey et al. |
| 8,961,547 | B2 | 2/2015 | Dietz et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,332 | B2 | 3/2015 | Farritor et al. |
| 8,978,845 | B2 | 3/2015 | Kim |
| 8,979,838 | B2 | 3/2015 | Woloszko et al. |
| 8,979,843 | B2 | 3/2015 | Timm et al. |
| 8,979,844 | B2 | 3/2015 | White et al. |
| 8,979,890 | B2 | 3/2015 | Boudreaux |
| 8,986,302 | B2 | 3/2015 | Aldridge et al. |
| 8,989,855 | B2 | 3/2015 | Murphy et al. |
| 8,992,422 | B2 | 3/2015 | Spivey et al. |
| 8,992,526 | B2 | 3/2015 | Brodbeck et al. |
| 9,005,199 | B2 | 4/2015 | Beckman et al. |
| 9,011,437 | B2 | 4/2015 | Woodruff et al. |
| 9,017,326 | B2 | 4/2015 | DiNardo et al. |
| 9,017,372 | B2 | 4/2015 | Artale et al. |
| 9,028,494 | B2 | 5/2015 | Shelton, IV et al. |
| 9,028,519 | B2 | 5/2015 | Yates et al. |
| 9,031,667 | B2 | 5/2015 | Williams |
| 9,033,983 | B2 | 5/2015 | Takashino et al. |
| 9,039,695 | B2 | 5/2015 | Giordano et al. |
| 9,039,705 | B2 | 5/2015 | Takashino |
| 9,039,731 | B2 | 5/2015 | Joseph |
| 9,044,243 | B2 | 6/2015 | Johnson et al. |
| 9,044,245 | B2 | 6/2015 | Condie et al. |
| 9,044,256 | B2 | 6/2015 | Cadeddu et al. |
| 9,044,261 | B2 | 6/2015 | Houser |
| 9,050,093 | B2 | 6/2015 | Aldridge et al. |
| 9,050,098 | B2 | 6/2015 | Deville et al. |
| 9,055,961 | B2 | 6/2015 | Manzo et al. |
| 9,060,770 | B2 | 6/2015 | Shelton, IV et al. |
| 9,060,775 | B2 | 6/2015 | Wiener et al. |
| 9,060,776 | B2 | 6/2015 | Yates et al. |
| 9,066,723 | B2 | 6/2015 | Beller et al. |
| 9,072,535 | B2 | 7/2015 | Shelton, IV et al. |
| 9,072,536 | B2 | 7/2015 | Shelton, IV et al. |
| 9,078,664 | B2 | 7/2015 | Palmer et al. |
| 9,089,327 | B2 | 7/2015 | Worrell et al. |
| 9,089,360 | B2 | 7/2015 | Messerly et al. |
| 9,094,006 | B2 | 7/2015 | Gravati et al. |
| 9,095,362 | B2 | 8/2015 | Dachs, II et al. |
| 9,101,385 | B2 | 8/2015 | Shelton, IV et al. |
| 9,107,672 | B2 | 8/2015 | Tetzlaff et al. |
| 9,113,900 | B2 | 8/2015 | Buysse et al. |
| 9,119,630 | B2 | 9/2015 | Townsend et al. |
| 9,119,657 | B2 | 9/2015 | Shelton, IV et al. |
| 9,119,957 | B2 | 9/2015 | Gantz et al. |
| 9,125,662 | B2 | 9/2015 | Shelton, IV |
| 9,125,667 | B2 | 9/2015 | Stone et al. |
| 9,138,289 | B2 | 9/2015 | Conley et al. |
| 9,149,324 | B2 | 10/2015 | Huang et al. |

(56) References Cited

U.S. PATENT DOCUMENTS

| | | |
|---|---|---|
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,326,812 B2 | 5/2016 | Waaler et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,662,131 B2 | 5/2017 | Omori et al. |
| 9,668,806 B2 | 6/2017 | Unger et al. |
| 9,687,295 B2 | 6/2017 | Joseph |
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,713,491 B2 | 7/2017 | Roy et al. |
| 9,724,118 B2 | 8/2017 | Schulte et al. |
| 9,724,152 B2 | 8/2017 | Horlle et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,782,214 B2 | 10/2017 | Houser et al. |
| 9,782,220 B2 | 10/2017 | Mark et al. |
| 9,795,436 B2 | 10/2017 | Yates et al. |
| 9,802,033 B2 | 10/2017 | Hibner et al. |
| 9,808,244 B2 | 11/2017 | Leimbach et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,877,782 B2 | 1/2018 | Voegele et al. |
| 9,888,958 B2 | 2/2018 | Evans et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,918,730 B2 | 3/2018 | Trees et al. |
| 9,931,157 B2 | 4/2018 | Strobl et al. |
| 9,937,001 B2 | 4/2018 | Nakamura |
| 9,943,357 B2 | 4/2018 | Cunningham et al. |
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,041,822 B2 | 8/2018 | Zemlok |
| 10,052,044 B2 | 8/2018 | Shelton, IV et al. |
| 10,058,376 B2 | 8/2018 | Horner et al. |
| 10,070,916 B2 | 9/2018 | Artale |
| 10,080,606 B2 | 9/2018 | Kappus et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,702 B2 | 11/2018 | Danziger et al. |
| 10,130,410 B2 | 11/2018 | Strobl et al. |
| 10,130,414 B2 | 11/2018 | Weiler et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,194,911 B2 | 2/2019 | Miller et al. |
| 10,194,972 B2 | 2/2019 | Yates et al. |
| 10,194,976 B2 | 2/2019 | Boudreaux |
| 10,194,977 B2 | 2/2019 | Yang |

(56) References Cited

U.S. PATENT DOCUMENTS

| | | |
|---|---|---|
| 10,211,586 B2 | 2/2019 | Adams et al. |
| 10,231,776 B2 | 3/2019 | Artale et al. |
| 10,238,387 B2 | 3/2019 | Yates et al. |
| 10,245,095 B2 | 4/2019 | Boudreaux |
| 10,258,404 B2 | 4/2019 | Wang |
| 10,265,118 B2 | 4/2019 | Gerhardt |
| 10,278,721 B2 | 5/2019 | Dietz et al. |
| 10,314,638 B2 | 6/2019 | Gee et al. |
| 10,321,950 B2 | 6/2019 | Yates et al. |
| 10,342,602 B2 | 7/2019 | Strobl et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0143678 A1 | 6/2009 | Keast et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |

(56) References Cited

U.S. PATENT DOCUMENTS

| | | |
|---|---|---|
| 2009/0254080 A1 | 10/2009 | Honda |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |
| 2011/0087224 A1 | 4/2011 | Cadeddu et al. |
| 2011/0257680 A1 | 10/2011 | Reschke et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078139 A1 | 3/2012 | Aldridge et al. |
| 2012/0078244 A1 | 3/2012 | Worrell et al. |
| 2012/0085358 A1 | 4/2012 | Cadeddu et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1* | 1/2014 | Shelton, IV ............ A61B 34/37 606/1 |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0194864 A1 | 7/2014 | Martin et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0263541 A1 | 9/2014 | Leimbach et al. |
| 2014/0263552 A1 | 9/2014 | Hall et al. |
| 2014/0353869 A1* | 12/2014 | Goodman .......... A61B 18/1445 264/104 |
| 2015/0032150 A1 | 1/2015 | Ishida et al. |
| 2015/0080876 A1 | 3/2015 | Worrell et al. |
| 2015/0230861 A1 | 8/2015 | Woloszko et al. |
| 2015/0250531 A1 | 9/2015 | Dycus et al. |
| 2015/0272659 A1 | 10/2015 | Boudreaux et al. |
| 2015/0272660 A1 | 10/2015 | Boudreaux et al. |
| 2015/0327918 A1 | 11/2015 | Sobajima et al. |
| 2016/0038225 A1 | 2/2016 | Couture et al. |
| 2016/0045248 A1 | 2/2016 | Unger et al. |
| 2016/0051316 A1 | 2/2016 | Boudreaux |
| 2016/0066980 A1 | 3/2016 | Schall et al. |
| 2016/0074108 A1 | 3/2016 | Woodruff et al. |
| 2016/0128762 A1 | 5/2016 | Harris et al. |
| 2016/0143687 A1 | 5/2016 | Hart et al. |
| 2016/0157923 A1 | 6/2016 | Ding |
| 2016/0157927 A1 | 6/2016 | Corbett et al. |
| 2016/0175029 A1 | 6/2016 | Witt et al. |
| 2016/0199123 A1 | 7/2016 | Thomas et al. |
| 2016/0199124 A1 | 7/2016 | Thomas et al. |
| 2016/0199125 A1 | 7/2016 | Jones |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296270 A1 | 10/2016 | Strobl et al. |
| 2017/0056097 A1 | 3/2017 | Monson et al. |
| 2017/0105787 A1 | 4/2017 | Witt et al. |
| 2017/0105789 A1 | 4/2017 | Boudreaux et al. |
| 2017/0135751 A1 | 5/2017 | Rothweiler et al. |
| 2017/0189102 A1 | 7/2017 | Hibner et al. |
| 2017/0312014 A1 | 11/2017 | Strobl et al. |
| 2017/0312015 A1 | 11/2017 | Worrell et al. |
| 2017/0312016 A1 | 11/2017 | Strobl et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325878 A1 | 11/2017 | Messerly et al. |
| 2017/0367751 A1 | 12/2017 | Ruddenklau et al. |
| 2018/0085156 A1 | 3/2018 | Witt et al. |
| 2018/0125571 A1 | 5/2018 | Witt et al. |
| 2018/0228530 A1 | 8/2018 | Yates et al. |
| 2018/0280075 A1 | 10/2018 | Nott et al. |
| 2018/0368906 A1 | 12/2018 | Yates et al. |
| 2019/0000468 A1 | 1/2019 | Adams et al. |
| 2019/0000470 A1 | 1/2019 | Yates et al. |
| 2019/0000528 A1 | 1/2019 | Yates et al. |
| 2019/0000530 A1 | 1/2019 | Yates et al. |
| 2019/0000555 A1 | 1/2019 | Schings et al. |
| 2019/0099209 A1 | 4/2019 | Witt et al. |
| 2019/0099212 A1 | 4/2019 | Davison et al. |
| 2019/0099213 A1 | 4/2019 | Witt et al. |
| 2019/0099217 A1 | 4/2019 | Witt et al. |

FOREIGN PATENT DOCUMENTS

| | | |
|---|---|---|
| CN | 2868227 Y | 2/2007 |
| DE | 4300307 A1 | 7/1994 |
| DE | 29623113 U1 | 10/1997 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0705571 A1 | 4/1996 |
| EP | 1862133 A1 | 12/2007 |
| EP | 2060238 A1 | 5/2009 |
| EP | 1747761 B1 | 10/2009 |
| EP | 1767164 B1 | 1/2013 |
| EP | 2578172 A2 | 4/2013 |
| GB | 2032221 A | 4/1980 |
| JP | S537994 A | 1/1978 |
| JP | H08229050 A | 9/1996 |
| JP | 2002186627 A | 7/2002 |
| WO | WO-8103272 A1 | 11/1981 |
| WO | WO-9314708 A1 | 8/1993 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-02080794 A1 | 10/2002 |
| WO | WO-2004078051 A2 | 9/2004 |
| WO | WO-2008130793 A1 | 10/2008 |
| WO | WO-2009067649 A2 | 5/2009 |
| WO | WO-2010104755 A1 | 9/2010 |
| WO | WO-2011008672 A2 | 1/2011 |
| WO | WO-2011044343 A2 | 4/2011 |
| WO | WO-2012044606 A2 | 4/2012 |
| WO | WO-2013131823 A1 | 9/2013 |

OTHER PUBLICATIONS

Henriques. F.C., "Studies in thermal injury V. The predictability and the significance of thermally induced rate processes leading to

(56) References Cited

OTHER PUBLICATIONS irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Glaser and Subak-Sharpe,Integrated Circuit Engineering, Addison-Wesley Publishing, Reading, MA (1979). (book—not attached).
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Abbott, et al. Proceedings of the 2007 IEEEIRDJ International Conference on Intelligent Robots and Systems. 410-416, 2007.
Cadeddu et al., "Magnetic positioning system for trocarless laparoscopic instruments," American College of Surgeons Poster, 2004.
Cadeddu et al., "Novel magnetically guided intra-abdominal camera to facilitate laparoendoscopic single site surgery: initial human experience," Surgical Endoscopy, SAGES Oral Manuscript, 2009.
Cadeddu et al., "Transabdominal magnetic anchoring system for trocar-less laparoscopic surgery," American Urological Association Poster, 2002.
Cadeddu et al., "Transabdominal magnetic anchoring system for trocar-less laparoscopic surgery," Journal of Urology Abstract, 2002.
Castellvi et al., "Completely transvaginal NOTES cholecystectomy in a porcine model using novel endoscopic instrumentation," Accepted for Poster Presentation, SAGES Annual Meeting, 2009.
Castellvi et al., "Hybrid transgastric NOTES cholecystectomy in a porcine model using a magnetically anchored cautery and novel instrumentation," Submitted for Presentation, ASGE, 2009.
Castellvi et al., "Hybrid transvaginal NOTES sleeve gastrectomy in a porcine model using a magnetically anchored camera and novel instrumentation," Accepted for Poster Presentation, SAGES Annual Meeting, 2009.
Duchene et al., "Magnetic positioning system for trocarless laparoscopic instruments," Engineering and Urology Society Poster, 2004.
Fernandez et al., "Development of a transabdominal anchoring system for trocar-less laparoscopic surgery," ASME Proceedings of/MECE, 2003.
Gedeon et al., "Maximizing coupling strength of magnetically anchored notes instruments: How thick can we go?" Submittedfor Presentation, Poster, SAGES Annual Meeting, 2008.
Gedeon et al., "Maximizing coupling strength of magnetically anchored notes instruments: How thick can we go?" SAGES Annual Meeting Poster, 2008.
Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.
Peirs et al., "A miniature manipulator for integration in self-propelling endoscope," Sensors and Actuators, 92:343-9, 2001.
Raman et al., "Complete transvaginal NOTES nephrectomy using magnetically anchored instrumentation," Journal of Endourology, 23(3):, 2009.367-371,2009.
Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.
Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.
Scott et al., "Completely transvaginal NOTES cholecystectomy using magnetically anchored instruments," Surg. Endosc., 21:2308-2316, 2007.
Scott et al., "Evaluation of a novel air seal access port for transvaginal notes cholecystectomy," Submitted for Presentation, SAGES Annual Meeting, 2008.
Scott et al., "Magnetically anchored instruments for transgastric endoscopic surgery," Oral Presentation for SAGES Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Short-term survival outcomes following transvaginal NOTES cholecystectomy using magnetically anchored instruments," Oral Presentation, ASGE Annual Meeting/DDW, 2007.
Scott et al., "Trans gastric, transcolonic, and transvaginal cholecystectomy using magnetically anchored instruments," SAGES Annual Meeting Poster, 2007.
Scott et al., "Transvaginal NOTES cholecystectomy using magnetically anchored instruments," Abstract for Video Submission, ASGE II1h Annual Video Forum, 2007.
Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.
Swain et al., "Wireless endosurgery for NOTES," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.

(56) References Cited

OTHER PUBLICATIONS

Zeltser et al., "Single trocar laparoscopic nephrectomy using magnetic anchoring and guidance system in the porcine model," The Journal of Urology, 178:288-291, 2007.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Wright, et al., "Time-Temperature Equivalence of Heat-Induced Changes in Cells and Proteins," Feb. 1998. ASME Journal of Biomechanical Engineering, vol. 120, pp. 22-26.
Douglas, S.C. "Introduction to Adaptive Filter". Digital Signal Processing Handbook. Ed. Vijay K. Madisetti and Douglas B. Williams. Boca Raton: CRC Press LLC, 1999.
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

Leonard I. Malis, M.D., "The Value of Irrigation During Bipolar Coagulation," 1989.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in Medical Infrared Imaging, N. A. Diakides and J. D. Bronzino, Eds. (2008).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Technology Overview, printed from www.harmonicscalpel.com, Internet site, website accessed on Jun. 13, 2007, (3 pages).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

\* cited by examiner

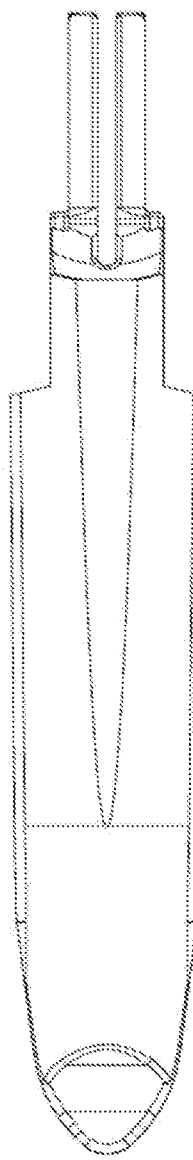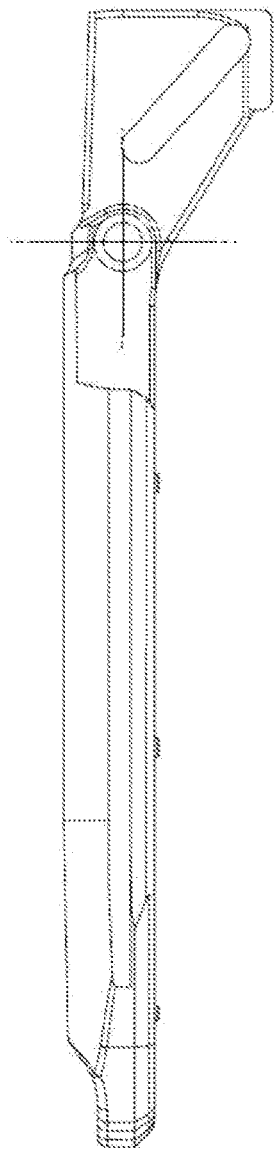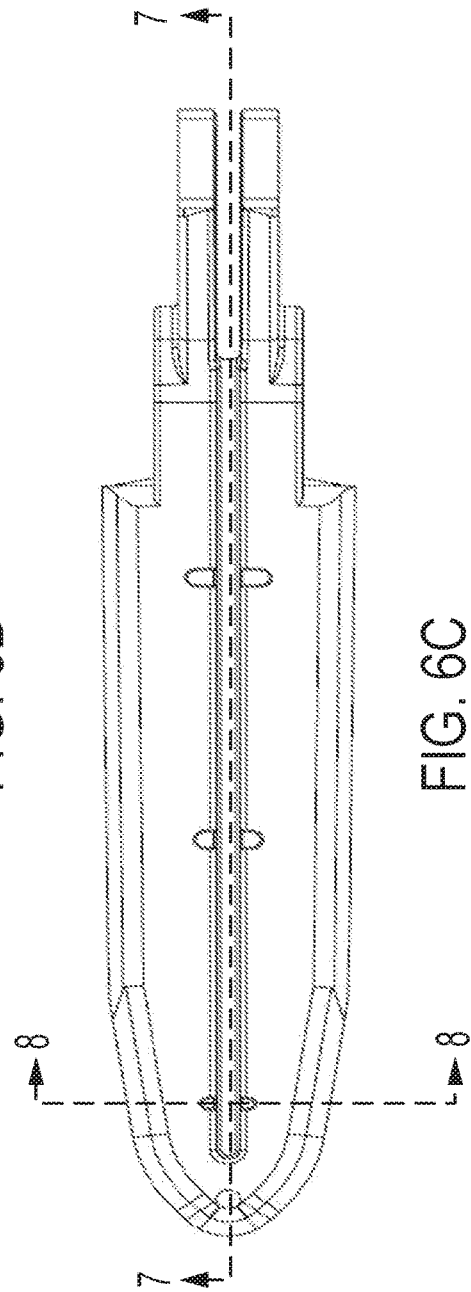

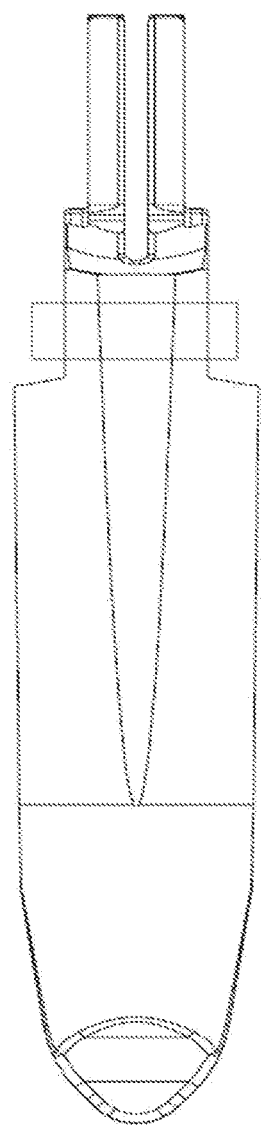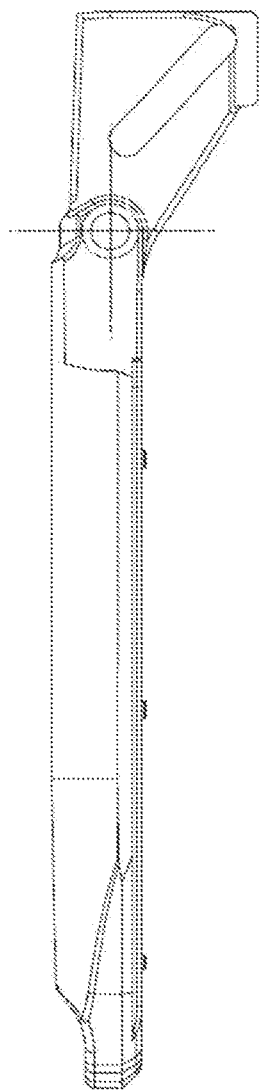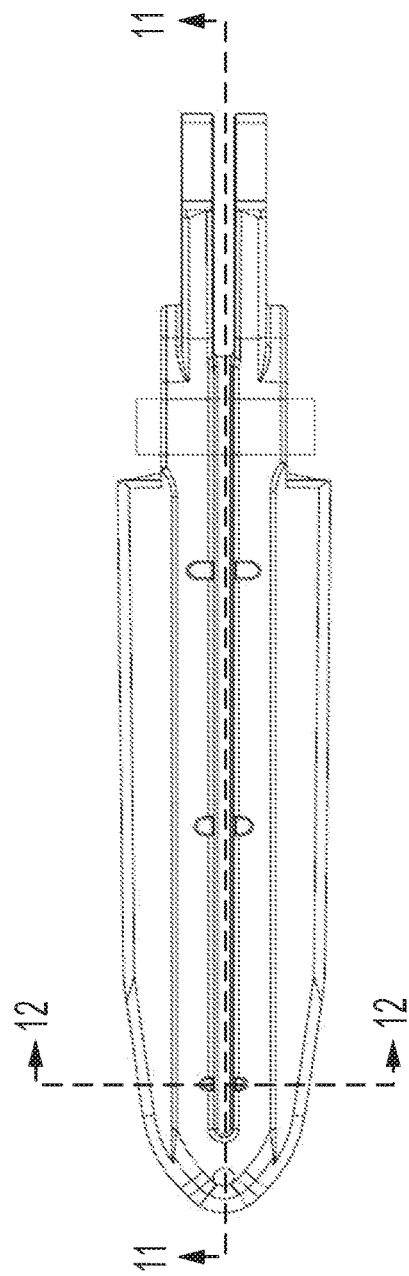
FIG. 10A
FIG. 10B
FIG. 10C

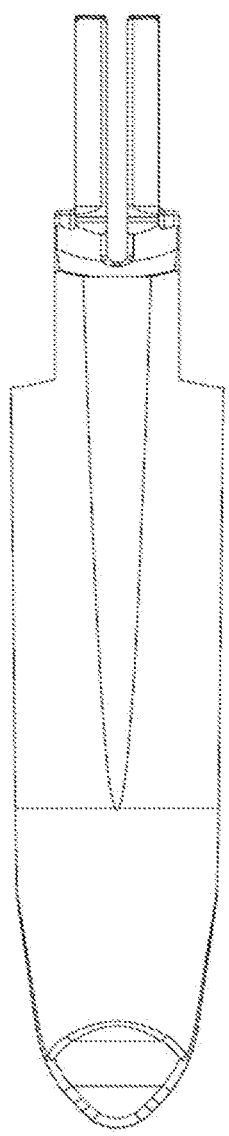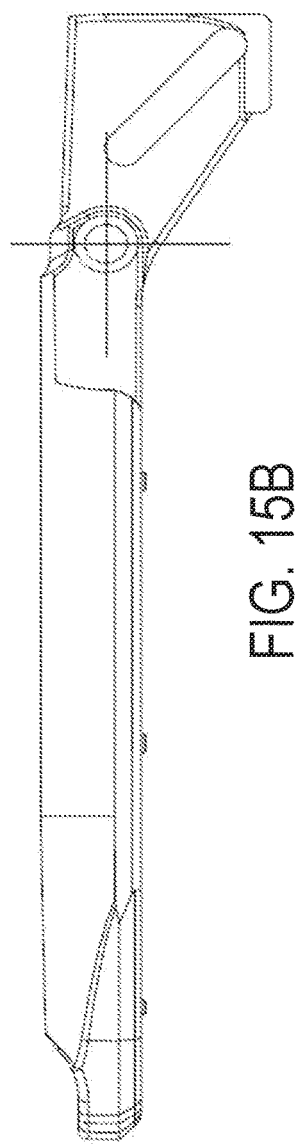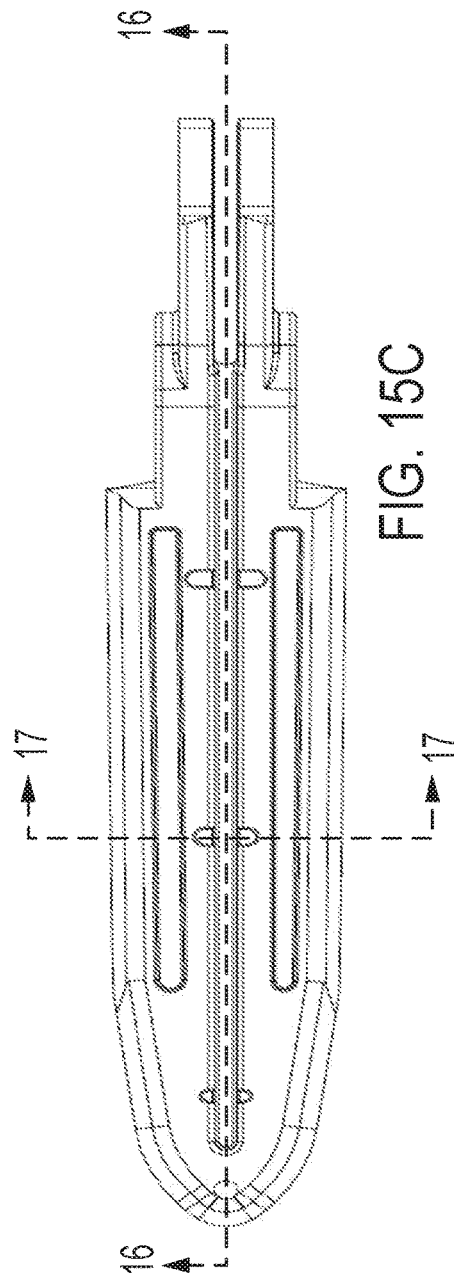

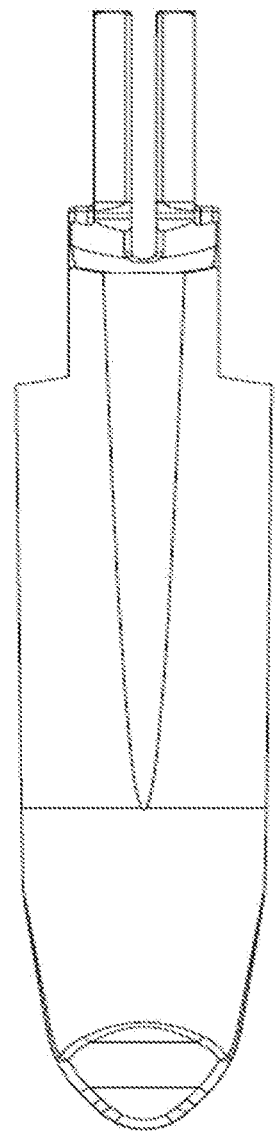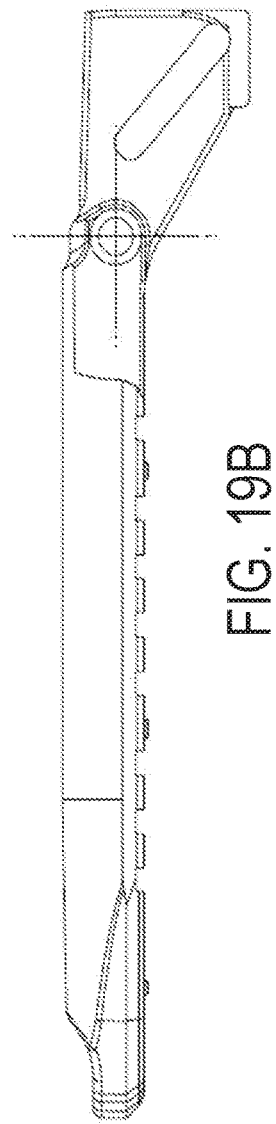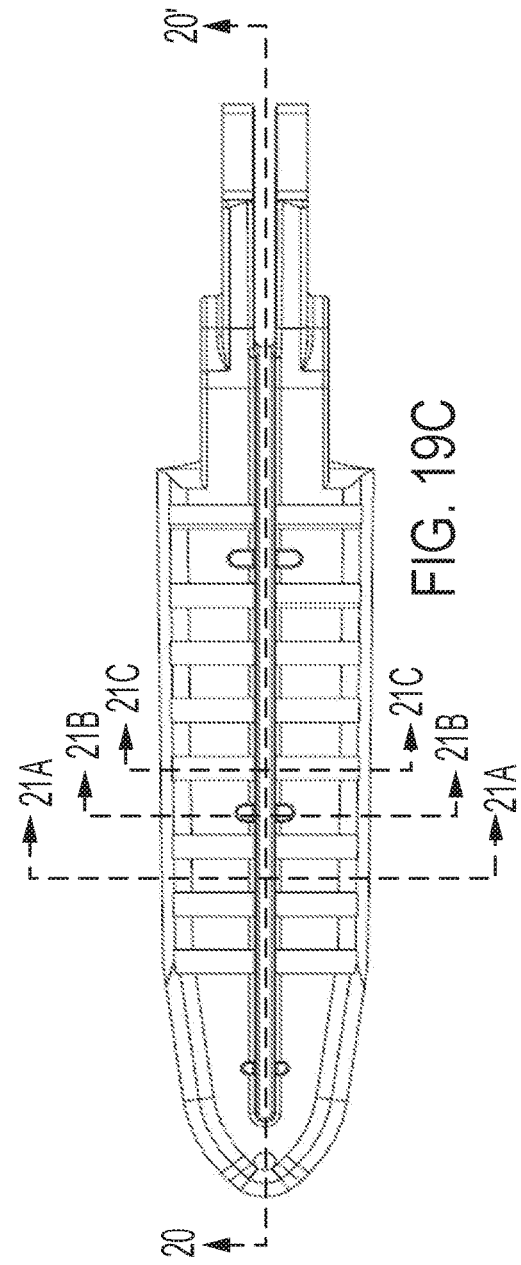

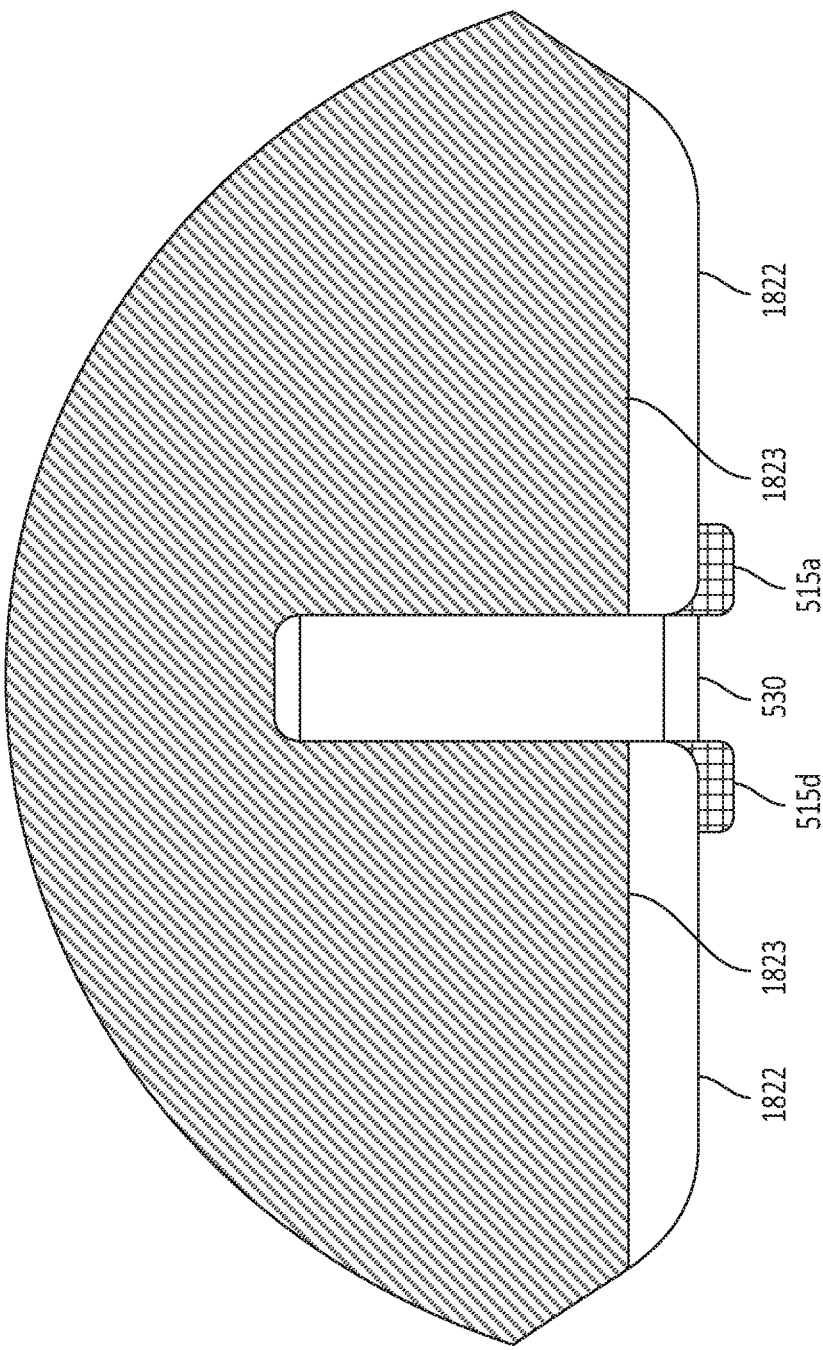

ELECTROSURGICAL INSTRUMENT WITH TEXTURED JAWS

BACKGROUND

Electrosurgical devices are used in many surgical operations. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar operation. During bipolar operation, current is introduced into and returned from the tissue by active and return electrodes, respectively, of the end effector. Bipolar devices may also have an end effector consisting of two or more jaws each having at least one of the active and or return electrodes. At least one of the jaws is moveable from a position spaced apart from the opposing jaw for receiving tissues to a position in which the space between the jaws is less than that of the first position. Movement of the moveable jaw compresses the tissue held between. Heat generated by the current flow through the tissue in combination with the compression achieved by the jaw movement may form hemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrosurgical devices also may include mechanisms to clamp tissue together, such as a stapling device, and/or mechanisms to sever tissue, such as a tissue knife. An electrosurgical device may include a shaft for placing the end effector proximate to tissue undergoing treatment. The shaft may be straight or curved, bendable or non-bendable. In an electrosurgical device including a straight and bendable shaft, the shaft may have one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

Electrical energy applied by an electrosurgical device can be transmitted to the instrument by a generator. The electrical energy may be in the form of radio frequency ("RF") energy. The electrical energy may be in the form of radio frequency ("RF") energy that may be in a frequency range described in EN 60601-2-2:2009+A11:2011, Definition 201.3.218—HIGH FREQUENCY. For example, the frequency in monopolar RF applications is typically restricted to less than 5 MHz. However, in bipolar RF applications, the frequency can be almost anything. Frequencies above 200 kHz can be typically used for monopolar applications in order to avoid the unwanted stimulation of nerves and muscles which would result from the use of low frequency current. Lower frequencies may be used for bipolar techniques if the risk analysis shows the possibility of neuromuscular stimulation has been mitigated to an acceptable level. Normally, frequencies above 5 MHz are not used in order to minimize the problems associated with high frequency leakage currents. However, higher frequencies may be used in the case of bipolar techniques. It is generally recognized that 10 mA is the lower threshold of thermal effects on tissue.

During its operation, an electrosurgical device can transmit RF energy through tissue compressed between the two or more jaws. Such RF energy may cause ionic agitation in the tissue, in effect producing resistive heating, and thereby increasing the temperature of the tissue. Increased temperature of the tissue may lead to tissue cauterization. RF energy may work particularly well on connective tissue, which is primarily comprised of collagen and shrinks when contacted by heat. Because a sharp boundary may be created between the affected tissue and the surrounding tissue, surgeons can operate with a high level of precision and control, without sacrificing untargeted adjacent tissue. In some surgical procedures, RF energy may be useful for sealing blood vessels.

During surgical resection of tissue, blood vessels may be severed either as part of the procedure or ancillary to the resection of a tissue of interest. Once a blood vessel has been severed, blood may flow into the surgical site, potentially obscuring the site from view and rendering the surgical procedure more difficult. If the severed blood vessel is a major vessel, such as an artery or vein, the patient may suffer significant blood loss during the procedure thereby significantly compromising the patient's health.

Many blood vessels comprise a three-layer structure. The inner most layer, the intima (or tunica interna), may line the lumen of the blood vessel. The intermediate layer (tunica media) may comprise smooth muscle cells that may contract to assist blood flow. The outermost layer, the adventitia (or tunica externa) is a complex structure that may include multiple cell types, such as leukocytes, fibroblasts, and myofibroblasts, imbedded in an extracellular matrix that may include a variety of collagen fibrils, fibronectin, and various proteoglycans.

It may be understood that successful cauterization of a blood vessel requires the application of both a sufficient compressive force to close the blood vessel as well as the application of the RF energy to heat and cauterize the tissue under compression. In order to apply the sufficient compressive force to the blood vessel, the end effector jaws of the electrosurgical device must securely grasp the adventitia of the blood vessel and apply sufficient pressure to overcome forces generated by the smooth muscle as well as the blood flow within. It may be recognized that the structure and composition of the adventitia may make it difficult for the end effector jaws to grasp a blood vessel securely enough to allow the compressive force and RF energy to be delivered for proper cauterization. Therefore, it may be useful to design an end effector of an electrosurgical device with features or textures to assure that the end effector jaws can securely grasp a blood vessel prior to and during cauterization.

SUMMARY

In one aspect, an electrosurgical system may include an RF current generator, a handle body, and an end effector in mechanical communication with the handle body. The end effector may include a first jaw comprising a first electrode having a first electrode surface, in which the first electrode is in electrical communication with a first terminal of the RF current generator, and a second jaw comprising a second electrode having a second electrode surface, in which the second electrode is in electrical communication with a second terminal of the RF current generator, and in which the first jaw comprises at least one feature configured to apply an amount of a compressive force to a tissue compressed between the at least one feature and the second electrode surface that differs from an amount of a compressive force applied to the tissue compressed between the first electrode surface and the second electrode surface when the first jaw is placed in a proximate position to the second jaw. Additionally, the second electrode is a planar surface.

In one aspect of the electrosurgical system, the at least one feature includes an at least one longitudinal channel disposed in the first electrode.

In one aspect of the electrosurgical system, the at least one feature includes an at least one transverse channel disposed in the first electrode.

In one aspect of the electrosurgical system, the second electrode is disposed on an insulating layer.

In one aspect, the electrosurgical system further includes a plurality of insulating pads in which each of the plurality of insulating pads has a surface co-planar with the second electrode surface, in which the at least one feature comprises a plurality of raised bosses extending from and in electrical communication with the first electrode, and in which at least one of the plurality of raised bosses is configured to engage at least one of the plurality of insulating pads when the first jaw is placed in the proximate position to the second jaw.

In one aspect of the electrosurgical system, the at least one feature further includes an at least one longitudinal ridge extending from and in electrical communication with the first electrode and wherein the plurality of raised bosses extend from a surface of the at least one longitudinal ridge.

In one aspect of the electrosurgical system, the at least one feature further includes an at least one longitudinal channel disposed in the first electrode.

In one aspect of the electrosurgical system, the at least one feature further includes an at least one transverse ridge extending from and in electrical communication with the first electrode and in which the plurality of raised bosses extend from a surface of the at least one transverse ridge.

In one aspect of the electrosurgical system, the at least one feature further includes an at least one transverse channel disposed in the first electrode.

In one aspect of the electrosurgical system, the second jaw is movable with respect to the first jaw when a force is applied to the end effector.

In one aspect of the electrosurgical system, the first jaw is movable with respect to the second jaw when a force is applied to the end effector.

In one aspect, an end effector for an electrosurgical device may include a first jaw comprising a first electrode having a first electrode surface, in which the first electrode is configured to be in electrical communication with a first terminal of an RF current generator and a second jaw comprising a second electrode having a second electrode surface, in which the second electrode is configured to be in electrical communication with a second terminal of the RF current generator. Further to the aspect, the first jaw includes at least one feature configured to apply an amount of a compressive force to a tissue compressed between the at least one feature and the second electrode surface that differs from an amount of a compressive force applied to the tissue compressed between the first electrode surface and the second electrode surface by the first electrode when the first jaw is placed in a proximate position to the second jaw, and further, the second electrode is a planar surface.

In one aspect of the end effector, the at least one feature is configured to apply an amount of a compressive force to the tissue compressed between the at least one feature and the second jaw that is greater than the amount of a compressive force applied to the tissue compressed between the first electrode surface and the second electrode surface by the first electrode when the first jaw is placed in the proximate position to the second jaw.

In one aspect of the end effector, the at least one feature includes at least one longitudinal ridge extending from and in electrical communication with the first electrode.

In one aspect of the end effector, the at least one feature includes at least one transverse ridge extending from and in electrical communication with the first electrode.

In one aspect of the end effector, the at least one feature is configured to apply an amount of a compressive force to the tissue compressed between the a least one feature and the second electrode surface that is less than the amount of a compressive force applied to the tissue compressed between the first electrode surface and the second electrode surface by the first electrode when the first jaw is placed in the proximate position to the second jaw.

In one aspect of the end effector, the at least one feature includes at least one longitudinal channel disposed in the first electrode.

In one aspect of the end effector, the at least one features includes at least one transverse channel disposed in the first electrode.

In one aspect of the end effector, the at least one feature is configured to apply an amount of a compressive force to the tissue compressed between the at least one feature and the second electrode surface that is greater than the amount of a compressive force applied to the tissue compressed between the first electrode surface and the second electrode surface by the first electrode when the first jaw is placed in the proximate position to the second jaw, and, further, at least a second feature is configured to apply an amount of a compressive force to the tissue compressed between the at least second feature and the second electrode surface that is less than the amount of a compressive force applied to the tissue compressed between the first electrode surface and the second electrode surface by the first electrode when the first jaw is placed in the proximate position to the second jaw.

In one aspect of the end effector, the second electrode is disposed on an insulating layer.

In one aspect, the end effector further includes at least one insulating pad in which the at least one insulating pad has a surface co-planar with the second electrode, in which the at least one feature has at least one raised boss extending from and in electrical communication with the first electrode, and in which the at least one raised boss is configured to engage the at least one insulating pad when the first jaw is placed in the proximate position to the second jaw.

In one aspect of the end effector, the at least one feature further includes at least one longitudinal ridge extending from and in electrical communication with the first electrode and in which the at least one raised boss extends from a surface of the at least one longitudinal ridge.

In one aspect of the end effector, the at least one feature further includes at least one transverse ridge extending from and in electrical communication with the first electrode and wherein the at least one raised boss extends from a surface of the at least one transverse ridge.

In one aspect of the end effector, the second jaw is movable with respect to the first jaw.

In one aspect of the end effector, the first jaw is movable with respect to the second jaw.

BRIEF DESCRIPTION OF THE FIGURES

The features of the various aspects are set forth with particularity in the appended claims. The various aspects, however, both as to organization and methods of operation, together with advantages thereof, may best be understood by reference to the following description, taken in conjunction with the accompanying drawings as follows:

FIGS. 6A, 6B, and 6C are planar views of a top, a side, and a bottom, respectively, of the aspect of the movable jaw depicted in FIG. 5.

FIGS. 10A, 10B, and 10C are planar views of a top, a side, and a bottom, respectively, of the aspect of the movable jaw depicted in FIG. 9.

FIGS. 15A, 15B, and 15C are planar views of a top, a side, and a bottom, respectively, of the aspect of the movable jaw depicted in FIG. 14.

FIGS. 19A, 19B, and 19C are planar views of a top, a side, and a bottom, respectively, of the aspect of the movable jaw depicted in FIG. 18.

FIG. 21C is a transverse sectional view taken along line 21C-21C of the aspect of the movable jaw depicted in FIG. 19C.

DETAILED DESCRIPTION

Figure 1:
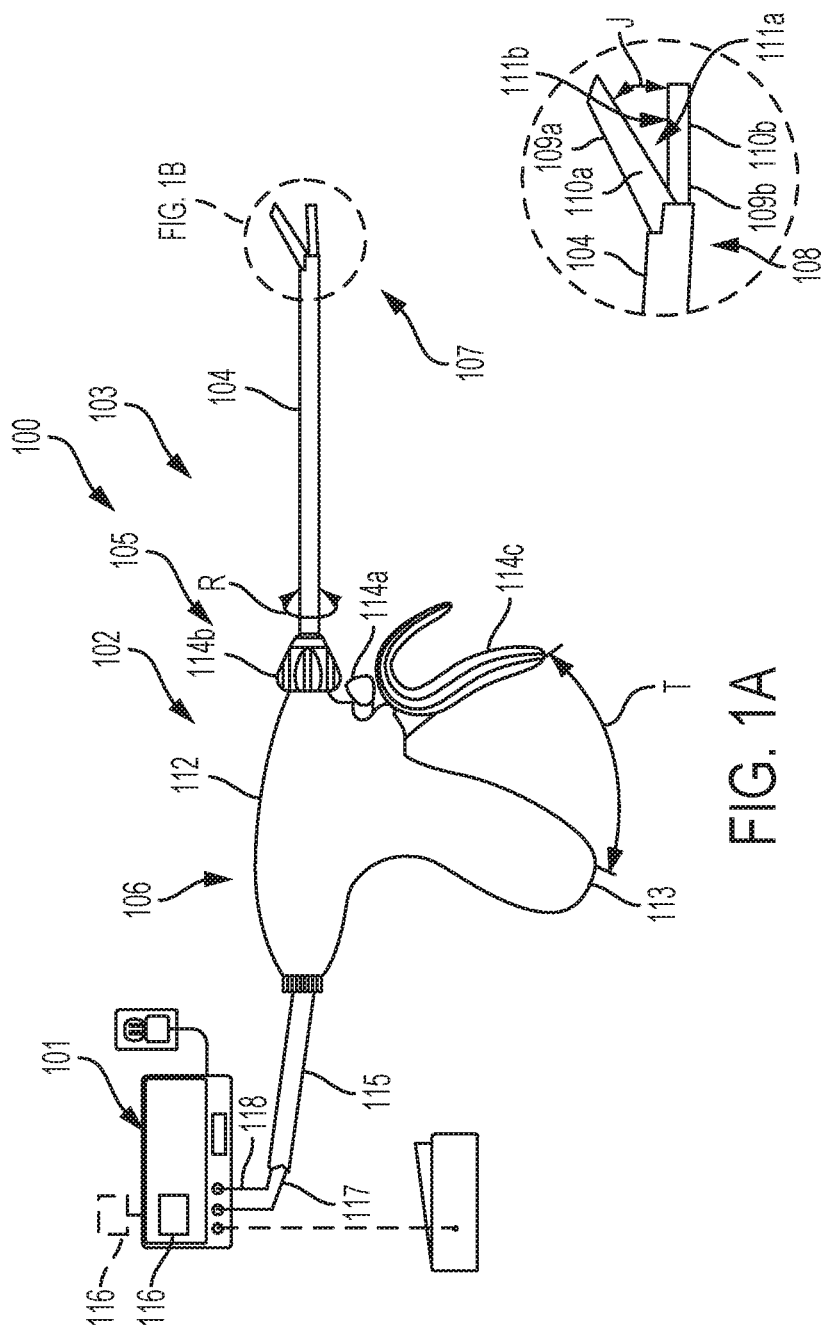
FIG. 1A shows a surgical instrument in electrical communication with an energy source, according to one aspect of the present disclosure.
FIG. 1B is a detailed view of the end effector of the surgical instrument shown in FIG. 1A, according to one aspect of the present disclosure.

The following description of certain examples of the technology should not be used to limit its scope. Other examples, features, aspects, aspects, and advantages of the technology will become apparent to those skilled in the art from the following description. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, aspects, examples, etc. described herein may be combined with any one or more of the other teachings, expressions, aspects, examples, etc. that are described herein. The following described teachings, expressions, aspects, examples, etc. should, therefore, not be viewed in isolation relative to each other. Various suitable ways in which the teachings herein may be combined will be readily apparent to those of ordinary skill in the art in view of the teachings herein. Such modifications and variations are intended to be included within the scope of the claims.

Also, in the following description, it is to be understood that terms such as front, back, inside, outside, upper, lower, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings. Throughout this disclosure, the term "proximal" is used to describe the side of a component, e.g., a shaft, a handle assembly, etc., closer to a user operating the surgical instrument, e.g., a surgeon, and the term "distal" is used to describe the side of the component farther from the user operating the surgical instrument.

Aspects of the present disclosure are presented for a single electrosurgical device configured for grasping tissue and performing sealing procedures using electrical and/or other energy. An end effector of the electrosurgical device may include multiple members arranged in various configurations to collectively perform the aforementioned functions. As used herein, an end effector may be referred to as a jaw assembly or clamp jaw assembly comprising an upper jaw member and a lower jaw member where at least one of the upper jaw member and the lower jaw member may be movable relative to the other. Jaw members may be adapted to connect to an electrosurgical energy source. A jaw member may incorporate an electrode. The electrode may be a positive or negative electrode. In a bipolar electrosurgical device, the electrodes may be adapted for connection to the opposite terminals of the electrosurgical energy source, such as a bipolar radio frequency (RF) generator, so as to generate a current flow therebetween. An electrosurgical energy may be selectively communicated through tissue held between the jaw members to effect a tissue seal and/or treatment. Tissue may be coagulated from the current flowing between the opposite polarity electrodes on a jaw member.

At least one jaw member may include a knife channel defined therein configured to reciprocate a knife therealong for severing tissue held between the jaw members. The knife channel may be an extended slot in the jaw member. The knife may be provided within a recess associated with the at least one jaw member. The electrosurgical device may have both coagulation and cutting functions. This may eliminate or reduce instrument interchange during a surgery. Cutting may be achieved using mechanical force alone or a combination of mechanical force and the electrosurgical energy. The electrosurgical energy may be selectively used for coagulation and/or cutting. The knife may be made from an electrically conductive material adapted to connect to the electrosurgical source, and selectively activatable to separate tissue disposed between the jaw members. The knife may be spring biased such that once tissue is severed, the knife may automatically return to an unengaged position within the knife channel or a retracted position in the recess.

In some aspects, the jaw members may be movable relative to each other. During operation of the electrosurgical device, at least one of the jaw members may move from a first, open position where the jaw members can be disposed around a mass of tissue, to a second, closed position where the jaw members grasp the tissue. The jaw members therefore may move through a graspers-like range of motion, similar to that of conventional pliers. In the second position, current flows between the jaw members to achieve hemostasis of the tissue captured therebetween. The jaw members may be configured to have a relatively thick proximal portion to resist bending. At least one of the jaw members may have a three-dimensional configuration with a D-shaped cross-sectional. The three-dimensional configuration with the D-shaped cross-sectional may resist bending. A lock mechanism may be included to lock the jaw members in the closed position. The lock mechanism may set the clamp pressure between the jaw members. At least one electrically conductive gap setting member may be provided between the jaw members to establish a desired gap between electrodes in bipolar electrosurgical devices.

The electrosurgical device may incorporate components to set a gap between the jaws of the end effector, grasp a tissue via the end effector, deliver energy to the tissue via one or more electrodes, and cut the tissue via a dissecting device such as a tissue knife. The structural capabilities of any aspect of an electrosurgical device may be designed for use in one or more of a variety of surgical procedures. In some surgical procedures, the treated tissue may be readily accessible to an end effector affixed to a relatively straight and unbendable shaft. In some alternative surgical procedures, the tissue may not be readily accessible to the end effector on such a shaft. In such procedures, the electrosurgical device may incorporate a shaft designed to bend so that the end effector may contact the tissue requiring treatment. In such a device, the shaft may include one or more articulated joints that may permit the shaft to bend under control by the user. A sliding knife may include a feature to provide actuating force to the sliding knife. A knife actuator may be operably coupled to the shaft for selectively reciprocating the knife through the knife channel.

A front portion assembly may be designed for a specific surgical procedure, while a reusable handle assembly, configured to releasably attach to a front portion assembly, may be designed to provide control of surgical functions common to each front portion assembly, such as tissue grasping, cauterizing, and cutting. Consequently, the number and types of devices required for surgeries can be reduced. The reusable handle assembly may be designed to automate common functions of the electrosurgical device. Device intelligence may be provided by a controller located in the reusable handle assembly that is configured to receive information from a front portion assembly. Such information may include data regarding the type and use of the front portion assembly. Alternatively, information may include data indicative of the position and/or activation of control components (such as buttons or slides that can be manipulated) that may indicate what system functions should be activated and in what manner.

In some non-limiting examples, the controller may supply the RF current when the energy activation control is placed in an activating position by the user. In some alternative non-limiting examples, the controller may supply the RF current for a predetermined period of time once the energy activation control is placed in an activing position. In yet another non-limiting example, the controller may receive data related to the position of the jaw members and prevent the RF current from being supplied to the to the one or more tissue cauterization power contacts if the jaw members are not in a closed position.

In some aspects, any of the mentioned examples also may be configured to articulate along at least one axis through various means, including, for example, a series of joints, one or more hinges or flexure bearings, and one or more cam or pulley systems. Other features may include cameras or lights coupled to one or more of the members of the end effector, and various energy options for the surgical device.

The electrosurgical device can be configured to source energy in various forms including, without limitation, electrical energy, monopolar and/or bipolar RF energy, microwave energy, reversible and/or irreversible electroporation energy, and/or ultrasonic energy, heat energy, or any combination thereof, to the tissue of a patient either independently or simultaneously. The energy can be transmitted to the electrosurgical device by a power source in electrical communication with the electrosurgical device. The power source may be a generator. The power source may be connected to the electrosurgical device via a suitable transmission medium such as a cable. The power source may be separate from the electrosurgical device or may be made integrally with the electrosurgical device to form a unitary electrosurgical system. In one non-limiting example, the power source may include one or more batteries located within a portion of the electrosurgical device. It may be understood that the power source may source energy for use on the tissue of the patient as well as for any other electrical use by other devices, including, without limitation, lights, sensors, communication systems, indicators, and displays, which operate in relation to and/or with the electrosurgical device to form an electrosurgical system.

As disclosed above, the electrosurgical device may be configured to source electrical energy in the form of RF energy. The electrosurgical device can transmit the RF energy through tissue compressed between two or more jaw members. In some surgical procedures, RF energy may be useful for removing, shrinking, or sculpting soft tissue while simultaneously sealing blood vessels. RF energy may work particularly well on connective tissue, which is primarily composed of collagen and shrinks when contacted by heat. Because a sharp boundary may be created between the affected tissue and the surrounding tissue, surgeons can operate with a high level of precision and control, without sacrificing untargeted adjacent tissue.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

As discussed above, the electrosurgical device may be used in conjunction with a generator. The generator may be an electrosurgical generator characterized by a fixed internal impedance and fixed operating frequency that deliver maximum power to an external load (e.g., tissue) having an electrical impedance in the range of about 50 ohms to 150 ohms. In this type of bipolar electrosurgical generator, the applied voltage may increase monotonically as the load impedance increases toward the maximum "open circuit" voltage as the load impedance increases to levels of tens of thousands of ohms or more. In addition, the electrosurgical device may be used with a bipolar electrosurgical generator having a fixed operating frequency and an output voltage that may be substantially constant over a range of load impedances of tens of ohms to tens of thousands of ohms including "open circuit" conditions. The electrosurgical device may be advantageously used with a bipolar electrosurgical generator of either a variable voltage design or substantially constant voltage design in which the applied voltage may be interrupted when the delivered current decreases below a predetermined level. Such bipolar generators may be referred to as automatic generators in that they may sense the completion of the coagulation process and terminate the application of voltage, often accompanied by an audible indication in the form of a cessation of a "voltage application" tone or the annunciation of a unique "coagulation complete" tone. Further, the electrosurgical device may be used with an electrosurgical generator whose operating frequency may vary with the load impedance as a means to modulate the applied voltage with changes in load impedance.

Various aspects of electrosurgical devices use therapeutic and/or sub-therapeutic electrical energy to treat tissue. Some aspects may be utilized in robotic applications. Some aspects may be adapted for use in a hand operated manner. In one non-limiting example, an electrosurgical device may include a proximal handle, a distal working end or end effector, and an introducer or elongated shaft disposed in-between.

In some non-limiting medical procedures, the electrosurgical device may be used to weld or seal vessels prior to tissue resection. Such vessels also may be removed as part of procedures to resect other tissue such as cysts, tumors, or infected materials. Blood vessel sealing may reduce bleeding, thereby decreasing potential harmful effects during a resection procedure. In such procedures, vessels may be cut at the cauterization location. It may be understood that complete sealing may be required at the site of the cut to prevent bleeding. It is therefore useful to have an electrosurgical device that may be prevented from cutting a vessel until complete sealing is assured.

To properly seal vessels, two mechanical parameters that affect thickness of the sealed vessel may be accurately controlled: the pressure applied to the vessel and the gap between the electrodes. Proper sealing may require that sufficient pressure is placed on the vessel to assure that the vessel walls are proximate to each other and no intervening gap remains therebetween. The vessel may be compressed to a pressure within a predetermined range. A typical range of appropriate pressures may be between about 30 pounds per square inch (about 0.2 MPa) and about 250 pounds per square inch (about 1.7 MPa). In addition, proper sealing may require that sufficient power is provided to assure that the vessel walls receive sufficient heat to weld the walls together. Thus, both tissue compression and tissue cauterization may be required to form a proper seal. These can be achieved by the jaw members of the end effector. As mentioned above, the jaw members may grasp, compress, and deliver the energy to the tissue.

To effectively carry out hemostasis, the jaw members should efficiently conduct a proper current flow through the grasped tissue. When that current is insufficient, coagulation of the tissue or vessel may be compromised. When the current is excessive, correspondingly excessive heating may occur with a potential for the generation of damaging electrical arcing. Excessive heating may result in the phenomenon of tissue and blood coagulum sticking to the surface of the jaw members. This may result in increased electrical impedance between the electrodes of the device and the tissue that may subsequently be grasped for the purpose of treatment. Such sticking tissue may evoke a disruption of the coagulated surface, which in itself may compromise the intended hemostatic effect. The end effector may incorporate highly polished electrode surfaces for the purpose of reducing the extent of tissue sticking as well as to facilitate their cleaning when sticking does occur.

When grasping tissue, the jaw members may come into mutual contact, causing a short circuit. For example, when a small tissue component is grasped between the jaw members and/or when the jaw members are compressed hard, the electrodes may be in contact with each other in the vicinity of the grasped tissue, causing short-circuiting. The jaw members may include insulative coatings that may be in contact in some geometry.

In various aspects, an electrically conductive gap setting member may be provided between the jaw members. The electrically conductive gap setting member may be affixed on and/or integral to one jaw member and extend to the other jaw member. The electrically conductive gap setting member may protrude through the jaw member. The electrically conductive gap setting member may define a gap between the jaw members. The electrically conductive gap setting member may be electrically conductive. The gap setting member may be made of a material that is electrically conductive and also is stiff to resist deformation in response to an applied force. The electrically conductive gap setting member may be sized and configured to avoid short-circuiting between the opposing electrodes and/or ensure that the electrodes would not close enough to arc without the presence of tissue between the electrodes.

According to various aspects, an end effector may include an electrically insulative member between the jaw members. The electrically insulative member may be provided on at least one of the jaw members. A jaw member may have a surface. The electrically insulative member may have a surface that is co-planar with the surface of the jaw member. A top surface of the at least one electrically insulative member may be round, square, rectangle, oval, or any other suitable shape. In some aspects where there is more than one electrically insulative member, the electrically insulative members may each have the same shape or different shapes with any combination of various shapes.

In various aspects, there may be more than one electrically insulative member. The electrically insulative members may have different shapes and/or sizes. All or some of the electrically insulative members may change shapes and/or sizes along the length of the electrodes. The electrically insulative members may have increasing or decreasing sizes along the length of the electrodes. The electrically insulative members may change shapes and/or sizes in a regular fashion or randomly.

In various aspects, the electrodes on the surfaces of the jaw members may be made of metal. The exposed portions of the surfaces of the jaw members may have smooth surfaces to minimize sticking to tissue or coagulum and to facilitate their cleaning when tissue debris or coagulum does accumulate. The surfaces of the jaw members may include thermally conductive components such as copper, silver, aluminum, tungsten, nickel, or any other thermally conductive materials that may occur to those skilled in the art. Laminar composites coated with a biocompatible metal coating may be applied to the surfaces. The jaw members may include laminar composites of thermally conductive copper and a mechanically stronger material, particularly, higher modulus stainless steel. Biocompatibility of the jaw members may be maintained through an electro-deposited biocompatible metal coating, such as chromium, that coats both the stainless steel and copper laminate while not affecting the electrically insulative members. In some non-limiting examples, for end effectors with small jaw members, for example, having a width of about 0.039" (1 mm) at their tip, laminar composites having a layer of 304 stainless steel of thickness of about 0.011" and a corresponding layer of copper having about 0.052" thickness may be provided. For larger jaw members, laminar composites having a layer of 304 stainless steel of thickness about 0.015" and a corresponding layer of copper having about 0.075" to about 0.085" thickness may be provided. The biocompatible coating may be provided, for example, as an electro-deposited chromium coating, for example, that identified as MED-COAT 2000 marketed by Electrolyzing Corporation of Ohio, Cleveland, Ohio 44112. This biocompatible coating is described as meeting or exceeding USP Class VI certification.

The at least one electrically insulative member may be made of electrically insulative material. The electrically insulative material may be alumina, ceramic, nylon, polyphthalamide (PPA), TEFLON, polyimide, parylene, any other suitable material, and/or any combinations thereof. In various aspects, smooth metal surfaces may be provided on the surfaces of the jaw members to reduce sticking of tissue or coagulum and these surfaces may be coated with an electrically conductive non-stick coating. Top surfaces of the at least one electrically insulative member may be coated with electrically insulative non-stick coating material.

In various aspects, the length of the jaw members may be set for the particular application in surgery. For example, the length of the jaw members of about 0.4" or 0.5" to about 0.75", such as about 0.47" (12 mm), may be used for smaller anatomical structures or fine work. For larger anatomical structures, the length of the jaw members may be about 1" or greater, for example, about 1.57" (40 mm).

The at least one electrically insulative member may have an appropriate diameter such that the electrically insulative member is neither so small as to pierce tissue nor so large as to take away too much of the electrode surface. The minimum diameter of the electrically insulative member may be about 0.03125" (1/32") as a member of this diameter may not pierce tissue unless the pressure applied on the tissue from the member is very high. If too much of the electrode surface is taken away by the electrically insulative member or members, there may be too little of the electrode surface and therefore, too little of the electrically conductive area adjacent to the electrically insulative member/members, and the electrosurgical device and/or the electrodes may not achieve the requisite performance. In some aspects, there is more than one electrically insulative member or members and may have the same or different diameters of any combination.

In the following detailed description, reference is made to the accompanying drawings, which form a part hereof. In the drawings, similar symbols and reference characters typically identify similar components throughout the several views, unless context dictates otherwise.

FIG. 1A shows an electrosurgical instrument 100 in electrical communication with a generator 101, according to one aspect of the present disclosure. The electrosurgical instrument 100 may be configurable with a flexible circuit 102 according to various aspects. The electrosurgical instrument 100 may comprise an elongate member 103, such as a shaft 104, having a proximal portion 105 coupled to a handle assembly 106. A distal portion 107 of the elongate member 103 may comprise an end effector 108 (see FIG. 1B) coupled to a distal end of the shaft 104. In some aspects, the end effector 108 may comprise a first jaw member 109*a* and a second jaw member 109*b*, each having an outer portion or surface 110*a*, 110*b*. At least one of the first jaw member 109*a* and the second jaw member 109*b* may move relative to the shaft 104. There may be only one jaw movable relative to the shaft 104, and the other jaw may be fixed relative to the shaft 104. At least one of the first jaw member 109*a* and the second jaw member 109*b* may be rotatably movable relative to the other along a path shown by arrow J to transition the first and second jaw members 109*a*, 109*b* between open and closed positions. In operation, the first and second jaw members 109*a*, 109*b* may be transitioned from the open position to a closed position to capture tissue therebetween. Captured tissue may contact one or more working portions of the jaw set 111*a*, 111*b* configured to apply energy to treat target tissue located at or near the end effector 108.

The type of energy may take various forms and includes, without limitation, monopolar and/or bipolar RF energy, microwave energy, reversible and/or irreversible electroporation energy, and/or ultrasonic energy, or any combination thereof. The handle assembly 106 may comprise a housing 112 defining a grip 113. In various aspects, the handle includes one or more control interfaces 114*a-c*, e.g., a button or switch 114*a*, rotation knob 114*b* rotatable along arrow R, and a trigger 114*c* movable relative to the grip 113 along arrow T, configured to provide operation instructions to the end effector 108. Multiple buttons, knobs, or triggers described also may be included as part of the housing 112 in order to manipulate one or more of the functioning members at the end effector 108. In some aspects, the handle assembly 106 may be further configured to electrically couple to a generator 101 to supply the electrosurgical instrument 100 with energy.

The generator 101 may be connected to the electrosurgical instrument 100 via a suitable transmission medium such as a cable 115. In one example, the generator 101 may be coupled to a controller, such as a control unit 116, for example. In various aspects, the control unit 116 may be made integrally with the generator 101, or may be provided as a separate circuit module or device electrically coupled to the generator 101 (shown in phantom to illustrate this option). The control unit 116 may include automated or manually operated controls to control the amount of current delivered by the generator 101 to the electrosurgical instrument 100. Although, as presently disclosed, the generator 101 is shown separate from the electrosurgical instrument 100, in some aspects, the generator 101 (and/or the control unit 116) may be made integrally with the electrosurgical instrument 100 to form a unitary electrosurgical system where a battery located within the electrosurgical instrument 100 may be the energy source and a circuit coupled to the battery produces the suitable electrical energy, ultrasonic energy, or heat energy. While the generator 101 is illustrated as generally coupled to the handle assembly 106, e.g., with a cord, it is to be understood that in some aspects the generator 101 may be positioned within the elongate member 103 and/or the handle assembly 106. For example, in one aspect, the generator 101 comprises one or more direct current batteries positioned in the handle assembly 106, shaft 104, or a portion thereof.

In one aspect, the generator 101 may comprise an input device located on a front panel of the generator 101. The input device may comprise any suitable device that generates signals suitable for programming the operation of the generator 101, such as a keyboard, or input port, for example. In one example, one or more electrodes in the first jaw 109a and one or more electrodes in the second jaw member 109b may be coupled to the generator 101. The cable 115 may comprise multiple electrical conductors for the application of electrical energy to a first electrode (which may be designated as a + electrode) and to a second electrode (which may be designated as a − electrode) of the electrosurgical instrument 100. It may be recognized that + and − designations are made solely for convenience and do not indicate an electrical polarity. An end of each of the conductors may be placed in electrical communication with a terminal of the generator 101. The generator 101 may have multiple terminals, each configured to contact one or more of the conductors. The control unit 116 may be used to activate the generator 101, which may serve as an electrical source. In various aspects, the generator 101 may comprise an RF source, an ultrasonic source, a direct current source, and/or any other suitable type of electrical energy source, for example, one which may be activated independently or simultaneously. In various aspects, the cable 115 may comprise at least one supply conductor 117 and at least one return conductor 118, wherein current can be supplied to the electrosurgical instrument 100 via the at least one supply conductor 117 and wherein the current can flow back to the generator 101 via the at least one return conductor 118. In various aspects, the at least one supply conductor 117 and the at least one return conductor 118 may comprise insulated wires and/or any other suitable type of conductor. As described below, the at least one supply conductor 117 and the at least one return conductor 118 may be contained within and/or may comprise the cable 115 extending between, or at least partially between, the generator 101 and the end effector 108 of the electrosurgical instrument 100. The generator 101 can be configured to apply a sufficient voltage differential between the supply conductor 117 and the return conductor 118 such that sufficient current can be supplied to the end effector 108 to perform the intended electrosurgical operation.

In one example, the generator 101 may be implemented as an electrosurgery unit (ESU) capable of supplying power sufficient to perform bipolar electrosurgery using RF energy. In one example, the ESU can be a Force Triad™ Energy Platform sold by Medtronic of Boulder Colo. In some aspects, such as for bipolar electrosurgery applications, an electrosurgical instrument 100 having an active electrode and a return electrode can be utilized, wherein the active electrode and the return electrode can be positioned against, adjacent to, and/or in electrical communication with the tissue to be treated such that current can flow from the active electrode through the PTC bodies and to the return electrode through the tissue. Thus, in various aspects, the electrosurgical system may comprise a supply path and a return path, wherein the captured tissue being treated completes, or closes, the circuit. In other aspects, the generator 101 may provide sub-therapeutic RF energy levels for purposes of evaluating tissue conditions and providing feedback in the electrosurgical system. Such feedback may be employed to control the therapeutic RF energy output of the electrosurgical instrument 100. Sub-therapeutic RF energy levels may be used for bipolar surgical procedures if a risk analysis shows the possibility of neuromuscular stimulation has been mitigated to an acceptable level. Under some conditions, frequencies above 5 MHz may not be used in order to minimize problems associated with high frequency leakage currents. However, higher frequencies may be used in the case of bipolar techniques. It is generally recognized that 10 mA is the lower threshold of thermal effects on tissue.

During operation of electrosurgical instrument 100, the user generally grasps tissue, supplies energy to the grasped tissue to form a weld or a seal (e.g., by an actuating button and/or pedal), and then drives a tissue-cutting member at the distal end of the electrosurgical instrument through the grasped tissue. According to various aspects, a jaw-closing member may be provided, and the translation of the axial movement of the jaw-closing member may be paced, or otherwise controlled, to aid in driving the jaw-closing member at a suitable rate of travel. By controlling the rate of travel, the likelihood that the captured tissue has been properly and functionally sealed prior to transection with the cutting member may be increased.

Figure 2:
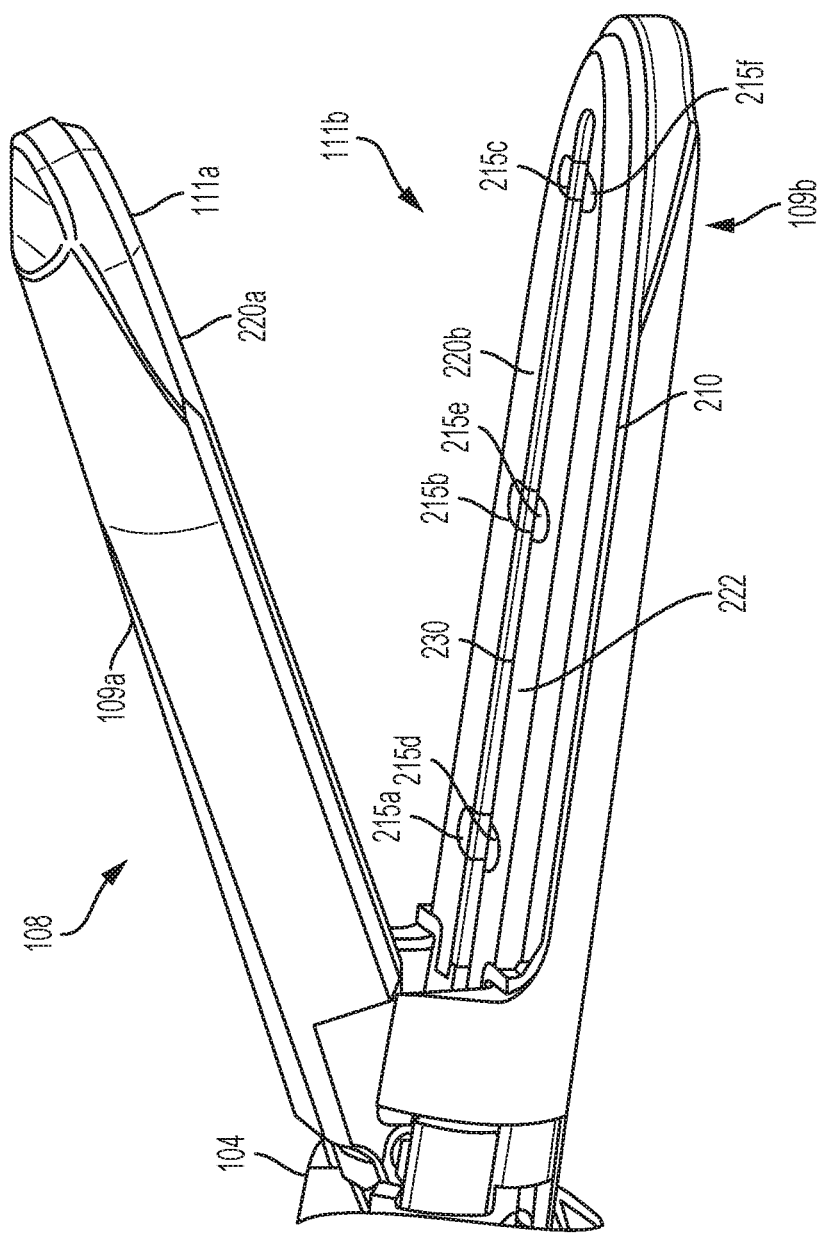
FIG. 2 illustrates a perspective view of one aspect of the end effector of the electrosurgical instrument of FIGS. 1A and 1B with the jaws open.

FIG. 2 is a perspective view of one example of an end effector 108 of a surgical instrument system 100. The end effector 108 may comprise a first jaw member 109a and a second jaw member 109b. As depicted in FIG. 2, the first jaw member 109a may be configured to move relative to the second jaw member 109b, and the second jaw member 109b may remain effectively in a fixed geometry with respect to shaft 104. It may be understood that in an alternative example, the second jaw member 109b may be configured to move relative to the first jaw member 109a, and the first jaw member 109a may remain effectively in a fixed geometry with respect to shaft 104.

FIG. 2 further depicts at least a portion of the working portion 111a of the first jaw member 109a and at least a portion of the working portion 111b of the second jaw member 109b. The working portion 111a of the first jaw member 109a may include at least a first electrode 220a. The working portion 111b of the second jaw member 109b may comprise at least a layered structure that may include, without limitation, an insulating layer 210 and a second electrode 220b.

The electrodes 220a,b may comprise an electrically conducting material. In various aspects, the electrodes 220a,b of the jaw members 109a,b, respectively, may be made of metal. The surfaces of the jaw members 109a,b may include thermally conductive components such as copper, silver, aluminum, tungsten, nickel, or any other thermally conductive materials that may occur to those skilled in the art. Laminar composites coated with a biocompatible metal coating may be applied to the surfaces. The jaw members 109a,b may include laminar composites of thermally conductive copper and a mechanically stronger material, particularly, higher modulus stainless steel. Biocompatibility of the jaw members 109a,b may be maintained through an electro-deposited biocompatible metal coating, such as chromium, that coats both the stainless steel and copper laminate. In some non-limiting examples, for end effectors 108 with small jaw members 109a,b, for example, having a width of about 0.039" (1 mm) at their tip, laminar composites having a layer of 304 stainless steel of thickness of about 0.011" and a corresponding layer of copper having about 0.052" thickness may be provided. For larger jaw members 109a,b, laminar composites having a layer of 304 stainless steel of thickness about 0.015" and a corresponding layer of copper having about 0.075" to about 0.085" thickness may be provided. The biocompatible coating may be provided, for example, as an electro-deposited chromium coating, for example, that identified as MED-COAT 2000 marketed by Electrolyzing Corporation of Ohio, Cleveland, Ohio 44112. This biocompatible coating is described as meeting or exceeding USP Class VI certification.

In one example, the second electrode 220b may have a U-shape that surrounds a knife channel 230, in which a knife may be disposed to reciprocate. The second electrode 220b may have a flat surface 222 that may be disposed against a tissue when the jaw members 109a,b are brought into a proximal position.

The insulating layer 210 may comprise an electrically insulative material. Without limitation, the electrically insulative material may be composed of an alumina, a ceramic, a nylon, a polyphthalamide (PPA), a TEFLON material, a polyimide, a parylene, any other suitable electrically insulative material, and/or any combination or combinations thereof.

As depicted in FIG. 2, the second electrode 220b may be deposited on or otherwise be placed in direct physical communication with the insulating layer 210. Insulating pads 215a-f may be formed on a top surface of the second electrode 220b. Alternatively, each of the insulating pads 215a-f may have a top surface that is co-planar with a surface 222 of the second electrode 220b. For example, the insulating pads 215a-f may comprise a portion of the insulating layer 210 and the second electrode 220b may be fabricated to cover a top surface of the insulating layer 210 and to at least partially surround at least one side of each of the insulating pads 215a-f. In some examples, the second electrode 220b may be fabricated so that the material comprising the second electrode 220b completely surrounds the sides of the insulating pads 215a-f so that only a top surface of each of the insulating pads 215 is exposed.

There may be a single insulating pad 215 or there may be multiple insulating pads 215a-f. The insulating pads 215a-f may be placed along a single side of the second electrode 220b (for example, insulating pads 215a-f along an inner side of a U-shaped second electrode 220b) or along multiple sides of the second electrode 220b (for example, along an inner side and along an outer side of a U-shaped second electrode 220b). Multiple insulating pads 215a-f may have the same dimensions (for example length and/or width) or may have differing dimensions. In one non-limiting example, the pair of insulating pads 215a,d of the second electrode 220b that are proximal to a joint in the end effector 108 may be longer and/or wider than a pair of insulating pads 215b,e located in a medial section of the second electrode 220b. Similarly, the pair of insulating pads 215b,e in a medial section of the second electrode 220b may be longer and/or wider than a pair of insulating pads 215c,f located in a distal section of the second electrode 220b. It may be understood that no limitations are implied regarding the relative dimensions among the multiple insulating pads 215a-f. Multiple insulating pads 215a-f may be equally spaced along a side of the second electrode 220b or may be variably spaced along a side of the second electrode 220b. The insulating pads 215a-f may have any shape appropriate to the function of the insulating pads 215a-f including, without limitation, a circular or partially circular shape, an elliptical or partially elliptical shape, an oval or partially oval shape, a square shape, or a rectangular shape. The insulating pads 215a-f may all have the same shape or may have differing shapes.

Figure 3:
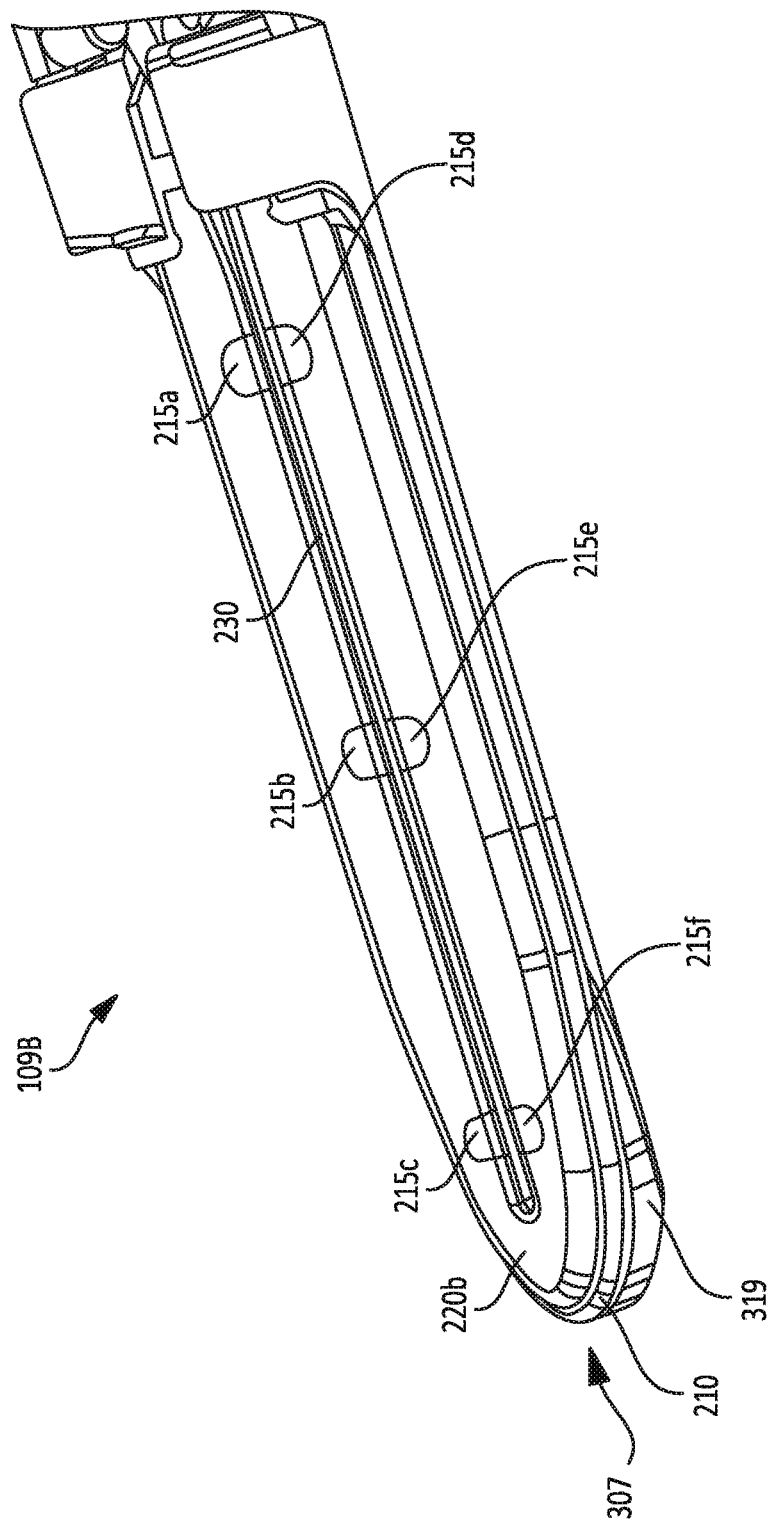
FIG. 3 illustrates a perspective view of one aspect of the non-movable jaw of the end effector depicted in FIG. 2.

FIG. 3 shows a perspective view of the second jaw member 109b of the example of an end effector 108 depicted in FIG. 2. The second jaw member 109b may be comprised of an electrode assembly layer 307 that may be in mechanical communication with a jaw frame 319. The electrode assembly layer 307 may be affixed to (non-removable from) the jaw frame 319. Alternatively, the electrode assembly layer 307 may be removably associated with the jaw frame 319. A removable electrode assembly layer 307 may be useful to permit the removable electrode assembly layer 307 to be removed for replacement purposes (if damaged) or for cleaning purposes (if fouling occurs). A health professional may also choose among a variety of configurations of removable electrode assembly layers 307 depending on the requirements of a particular surgical intervention.

Figure 4A:
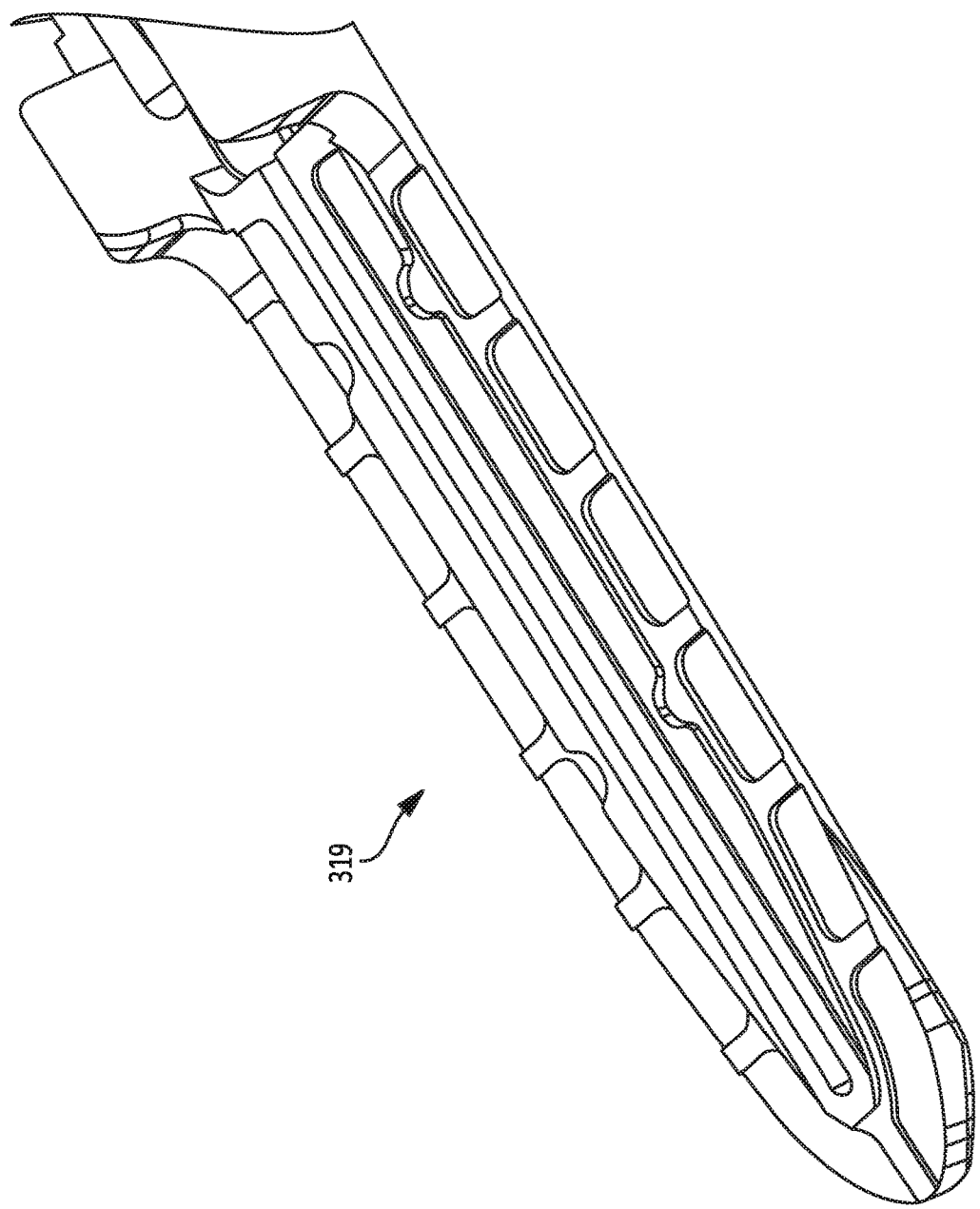
FIG. 4A illustrates a perspective view of one aspect of a jaw member frame of the non-movable jaw depicted in FIG. 3.
Figure 4B:
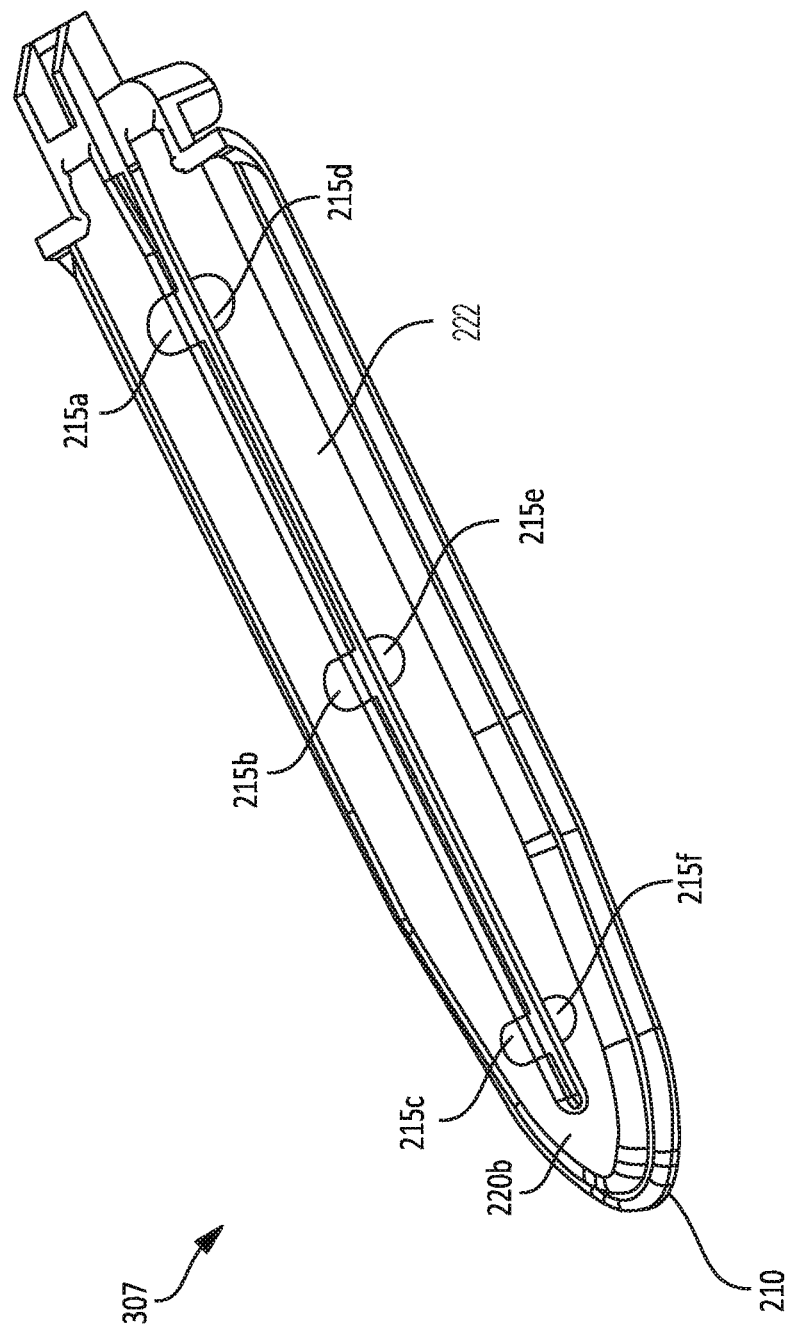
FIG. 4B illustrates a perspective view of one aspect of an electrode assembly of the non-movable jaw depicted in FIG. 3.
Figure 4C:
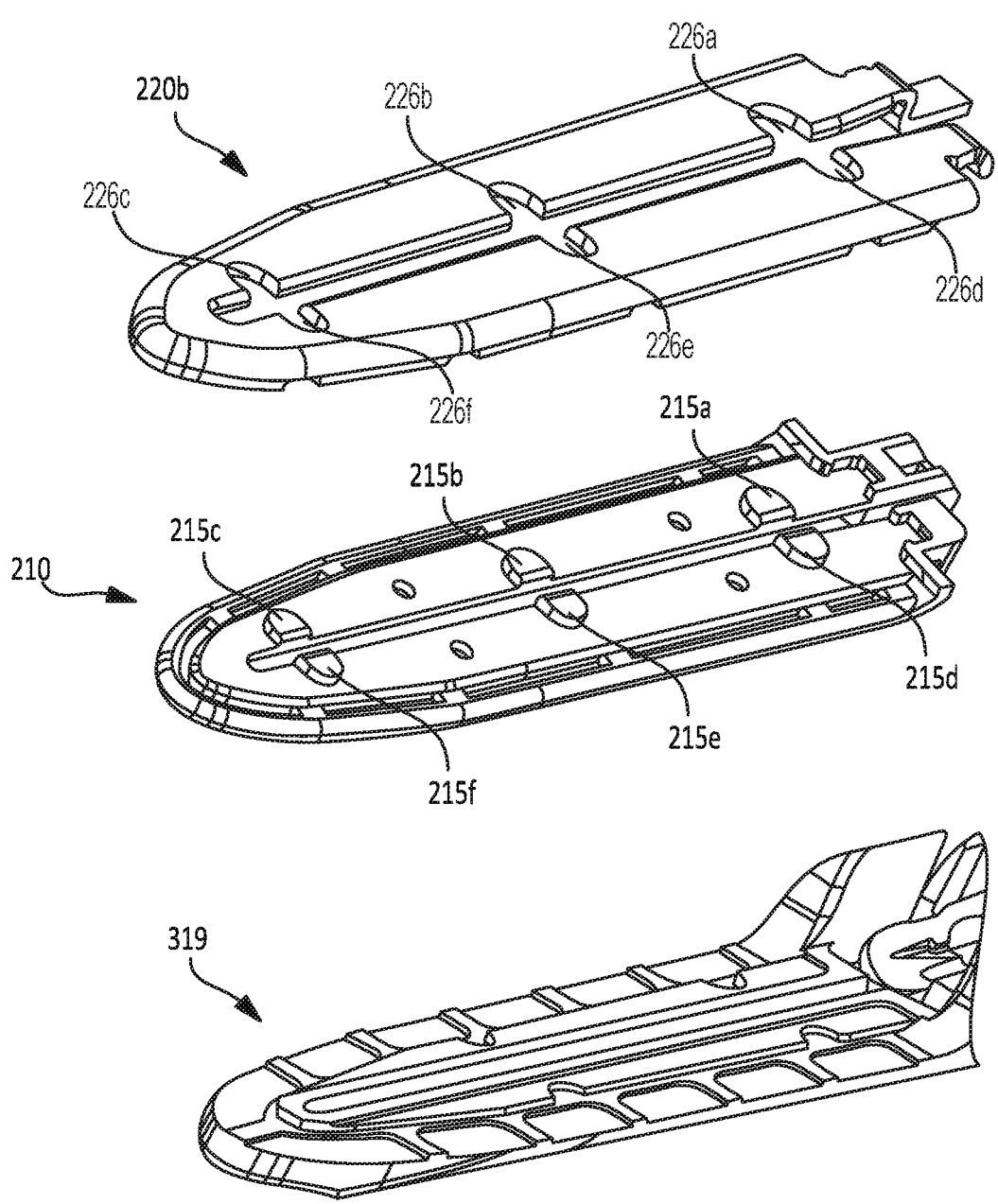
FIG. 4C illustrates an exploded view of the aspect of the non-movable jaw depicted in FIG. 3.

FIGS. 4A-C depict multiple views of the second jaw member 109b and aspects of its components. FIG. 4A depicts one aspect of a jaw frame 319 which may form a component of second jaw member 109b. The jaw frame 319 may be in mechanical communication with electrode assembly layer 307, depicted in FIG. 4B. In one aspect, the jaw frame 319 may be configured to stabilize the electrode assembly layer 307 of the second jaw member 109b against the first jaw member 109a when the jaw members 109a,b are placed in a proximate configuration, for example when compressing and cauterizing a piece of tissue. The electrode assembly layer 307 may comprise a second electrode 220b having a second electrode surface 222 placed in mechanical communication with insulating layer 210. FIG. 4C is an exploded view of the second jaw member 109b depicted in FIG. 3. FIG. 4C illustrates an aspect of the second jaw member 109b comprising a second electrode 220b having a second electrode surface 222, an insulating layer 210, and a jaw frame 319. In one example, the insulating layer 210 may comprise one or more insulating pads 215a-f. The second electrode 220b may have cut-outs 226a-f, each cut-out 226 configured to accept an insulating pad 215 so that the surface of each of the insulating pads 215a-f is co-planar with the surface 222 of the second electrode 220b.

Figure 5:
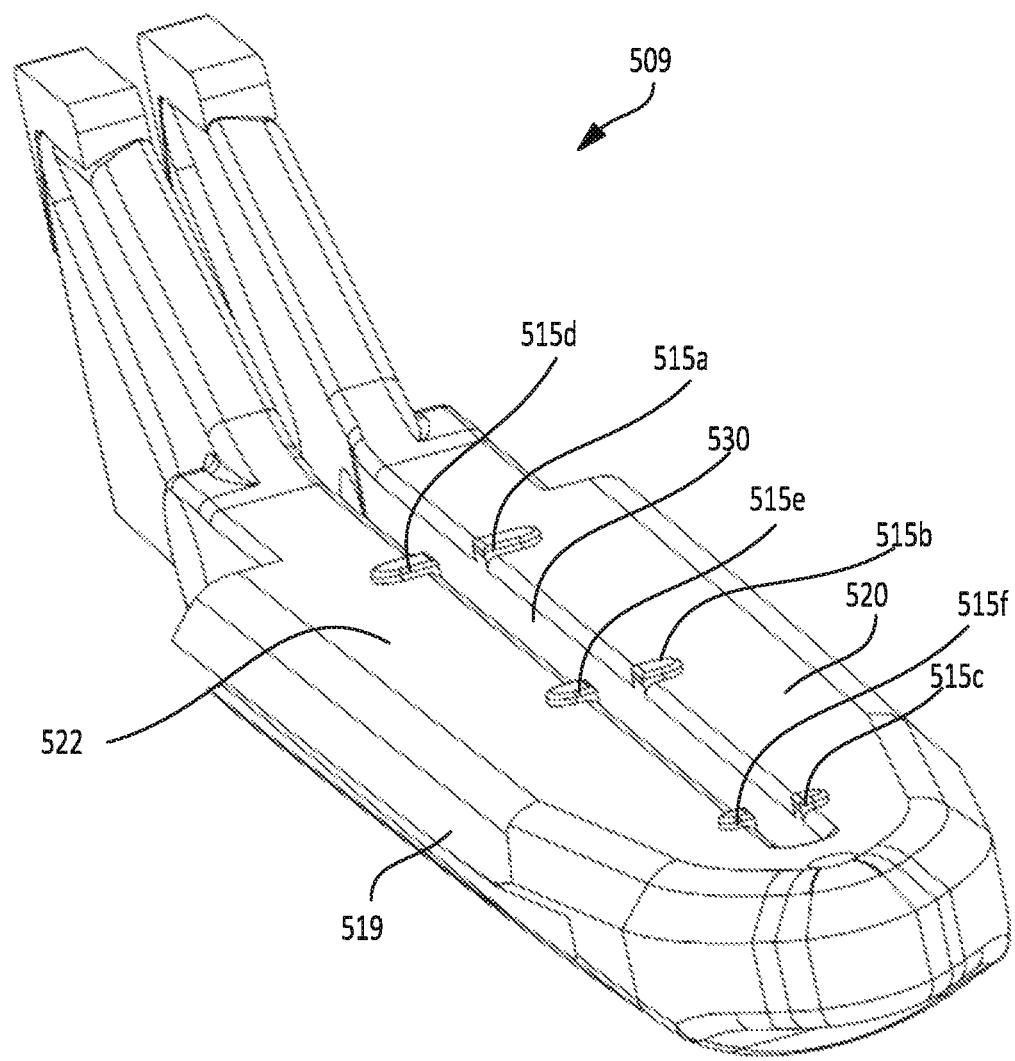
FIG. 5 illustrates a perspective view of one aspect of a movable jaw of the end effector depicted in FIG. 2.

FIG. 5 is a perspective view of a first example of a first jaw member 509 that may be incorporated into an end effector 108 (see FIG. 2) of an electrosurgical instrument 100 (see FIG. 1). The working portion of the first jaw member 509 may include a first jaw assembly 519 including a first electrode 520 having a surface 522 configured to contact a portion of a tissue when the first jaw member 509 is brought into a proximal position with respect to a second jaw member (for example, see 109b of FIG. 2). As depicted in FIG. 5, the surface 522 of the exemplary first jaw member 509 may comprise a primarily flat surface. The first jaw member 509 may also include a knife channel 530 through which a tissue cutting knife may reciprocate. Additionally, the first electrode 520 may incorporate features including one or more raised bosses 515a-f.

There may be a single raised boss 515 or there may be multiple raised bosses 515a-f. The raised bosses 515a-f may be placed along a single side of the first electrode 520 (for example, raised bosses 515a-f along an inner side of a U-shaped first electrode 520) or along multiple sides of the first electrode 520 (for example, along an inner side and along an outer side of a U-shaped first electrode 520). Multiple raised bosses 515a-f may have the same dimensions (for example length and/or width) or may have differing dimensions. In one non-limiting example, the pair of raised bosses 515a,d of the first electrode 520 that are proximate to a proximal joint in the end effector may be longer and/or wider than a pair of raised bosses 515b,e located in a medial section of the first electrode 520. Similarly, the pair of raised bosses 515b,e in a medial section of the first electrode 520 may be longer and/or wider than a pair of raised bosses 515c,f located in a distal section of the first electrode 520. It may be understood that no limitations are implied regarding the relative dimensions among the multiple raised bosses 515a-f. Multiple raised bosses 515a-f may be equally spaced along a side of the first electrode 520 or may be variably spaced along a side of the first electrode 520. The raised bosses 515a-f may have any shape appropriate to the function of the raised bosses 515a-f including, without limitation, a circular or partially circular shape, an elliptical or partially elliptical shape, an oval or partially oval shape, a square shape, or a rectangular shape. The raised bosses 515a-f may all have the same shape or may have differing shapes. The raised bosses 515a-f may be conducting or non-conducting. Conducting raised bosses 515a-f may be in electrical communication with the first electrode 520 and may have the same electrical polarity as the first electrode 520. Alternatively, non-conducting raised bosses 515a-f may not be in electrical communication with the first electrode 520 and may lack an electrical polarity with respect to either the first electrode 520 or a second electrode (for example 220b in FIGS. 4A-C).

Each of the raised bosses 515a-f may be configured to engage one of the multiple insulating pads 215a-f (see FIG. 2) when the first jaw 109a is moved proximate to the second jaw 109b. It may be understood that the term "engage" in this context may include forming a direct physical contact between a surface of a raised boss 515 and a surface of a mating insulating pad 215. However, the term "engage" in this context may also include a raised boss 515 and a mating insulating pad 215 being brought into a proximate but non-contacting position, for example when a piece of tissue is compressed between a raised boss 515 and a surface of a mating insulating pad 215 when the first jaw 109a is moved proximate to the second jaw 109b.

Figure 7:
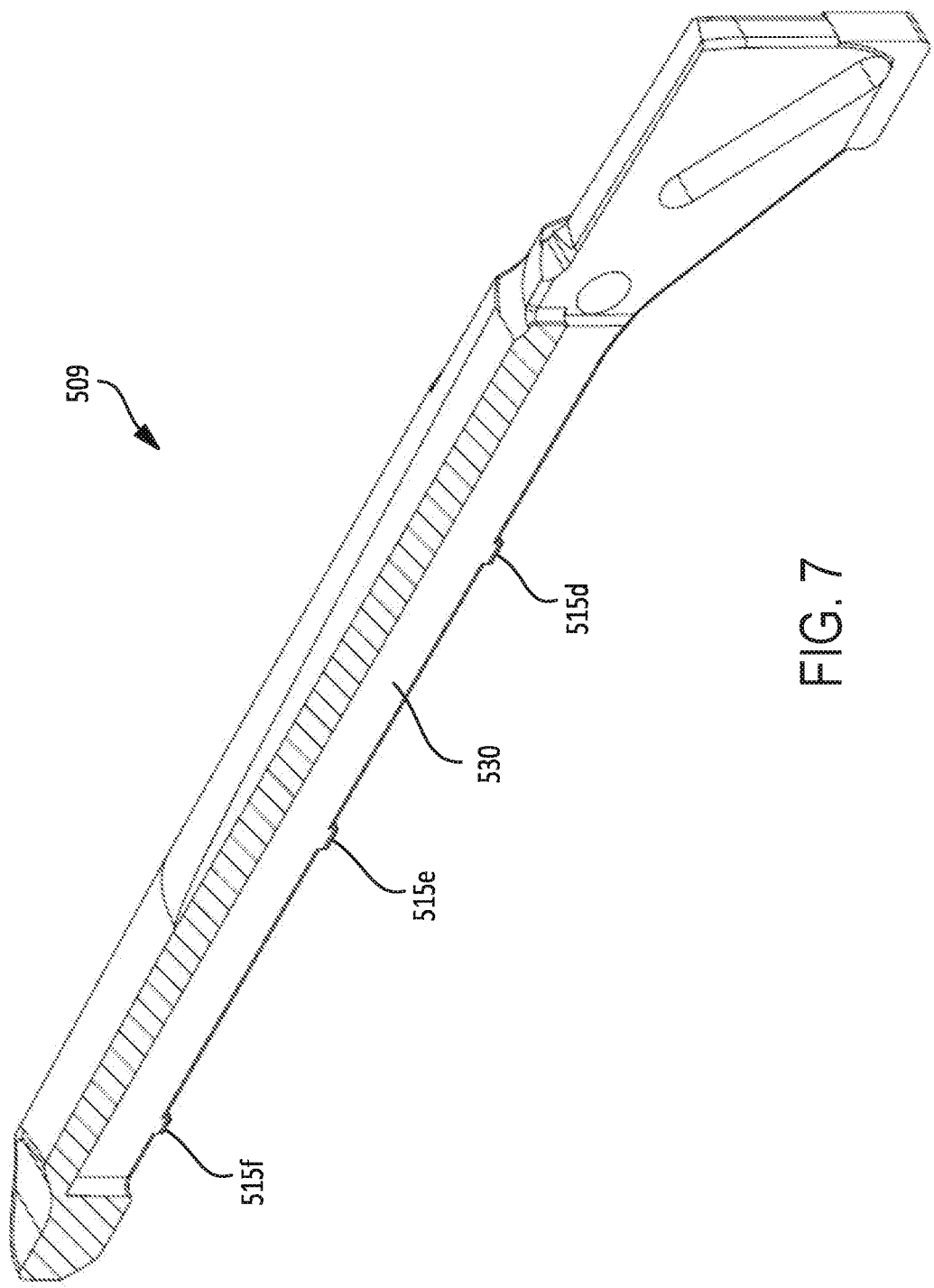
FIG. 7 is a longitudinal sectional view taken along line 7-7 of the aspect of the movable jaw of depicted in FIG. 6C.
Figure 8:
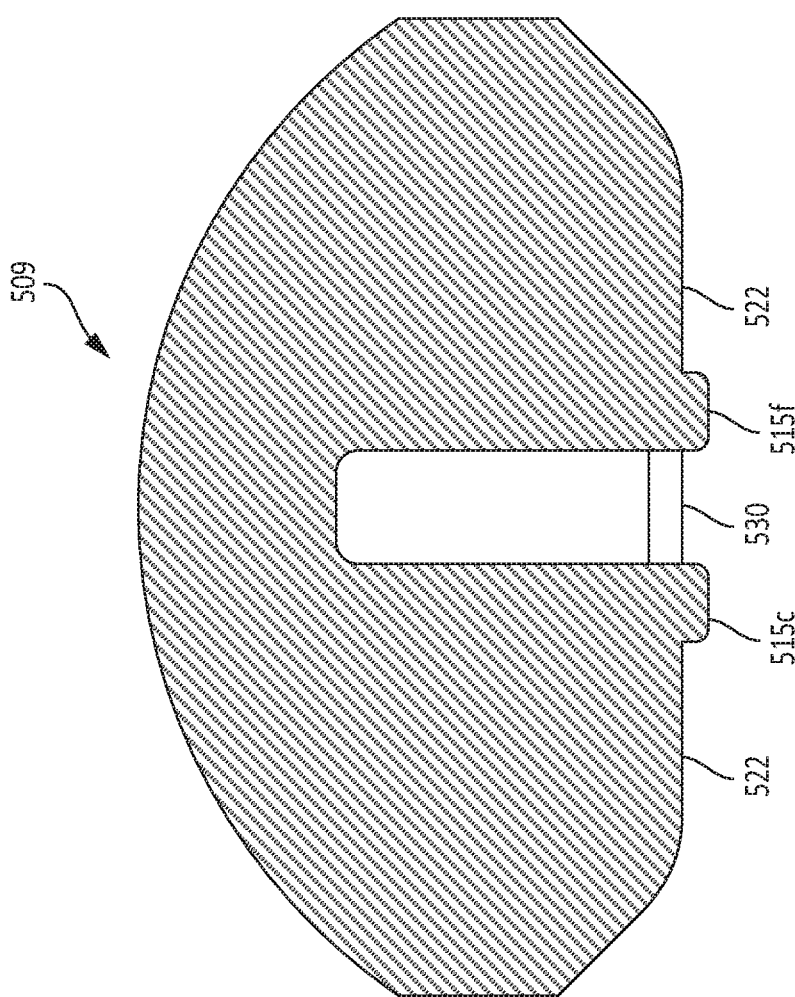
FIG. 8 is a transverse sectional view taken along line 8-8 of the aspect of the movable jaw depicted in FIG. 6C.

FIGS. 6A-C are top, side, and bottom plan views, respectively, of the example of the first jaw member 509 depicted in FIG. 5. FIG. 7 is a longitudinal cross-sectional view of the example of the first jaw member 509 depicted in FIG. 6C taken along line 7-7. The longitudinal cross-sectional view depicted in FIG. 7 particularly illustrates the knife channel 530 as well as cross-sectional views of the raised bosses 515d,e,f of first jaw member 509. FIG. 8 is a transverse cross-sectional view of the example of the first jaw member 509 depicted in FIG. 6C taken along line 8-8. The transverse cross-sectional view of FIG. 8 particularly illustrates the knife channel 530, cross-sectional views of raised bosses 515c,f, and the essentially flat surface 522 of the first electrode of first jaw member 509.

Figure 9:
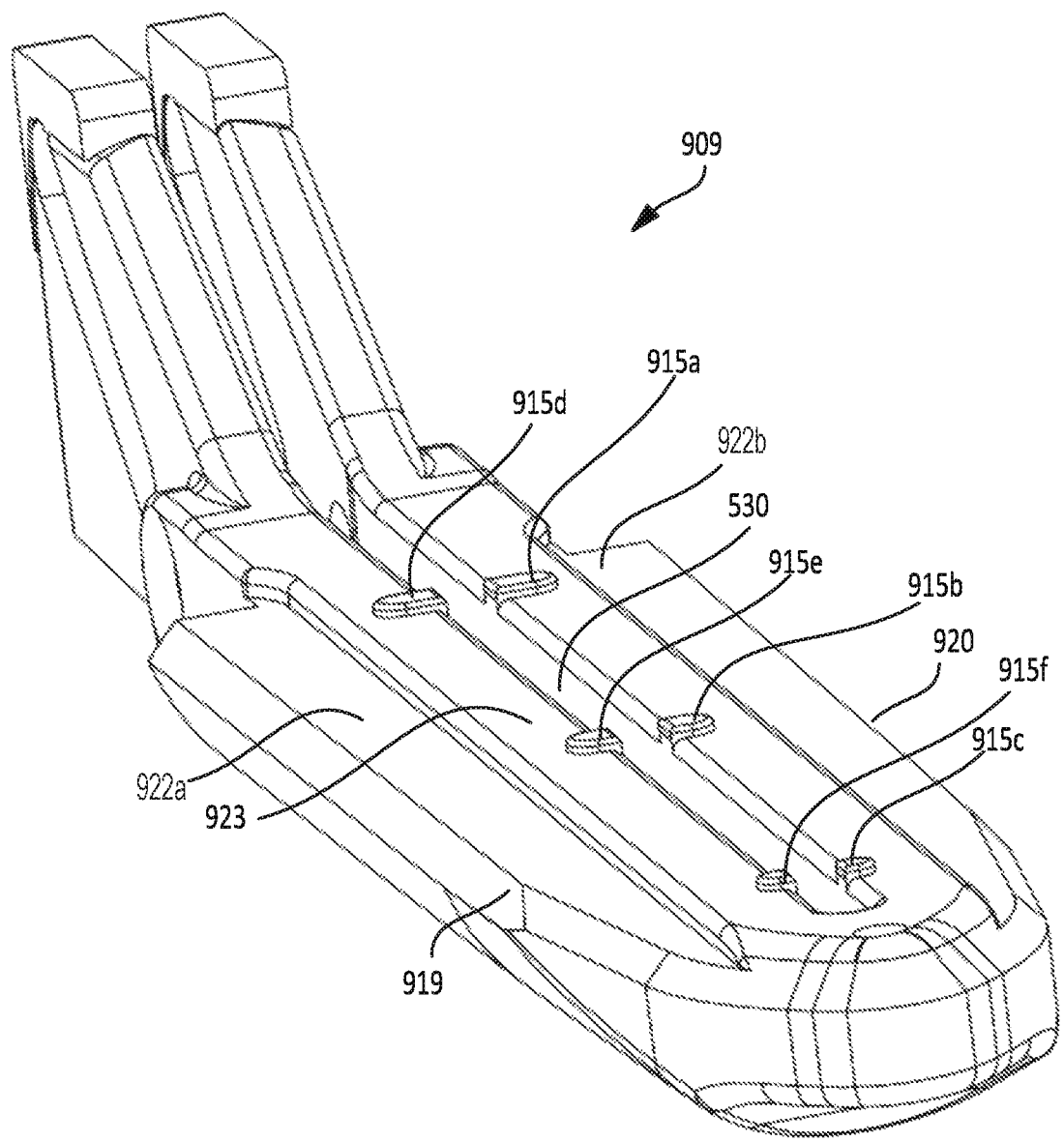
FIG. 9 illustrates a perspective view of a second aspect of a movable jaw of the end effector depicted in FIG. 2.

FIG. 9 is a perspective view of a first example of a first jaw member 909 that may be incorporated into an end effector 108 (see FIG. 2) of an electrosurgical instrument 100 (see FIG. 1). The working portion of the first jaw member 909 may include a first jaw assembly 919 including a first electrode 920 having a surface 922. As depicted in FIG. 9, at least a portion of the surface 922 of the exemplary first electrode 920 may comprise a flat surface. The first jaw member 909 may also include a knife channel 530 through which a tissue cutting knife may reciprocate.

Additionally, the first electrode 920 may incorporate features, for example one or more raised ridges 923. In the aspect depicted in FIG. 9, the first electrode 920 includes a single, U-shaped raised ridge 923 vertically protruding above the surface 922 and which may surround the knife channel 530. Alternatively, the first electrode 920 may include one or more raised ridges 923. The raised ridges 923 may be placed along a single side of the first electrode 920 or along multiple sides of the first electrode 920. Multiple raised ridges 923 may have the same dimensions (for example vertical extent above the electrode surface 922) or may have differing dimensions. The one or more raised ridges 923 may be parallel to each other and may be parallel to, and on opposing sides of, the knife channel 530. It may be recognized that the depiction of the one or more raised ridges 923 in FIG. 9 is not considered limiting either in number, shape, length, height, or width of the one or more raised ridges 923, or their disposition about the first electrode 920. Thus, there may be one, two, three or any number of such raised ridges 923. The one or more raised ridges 923 may have the same length, width, or height or have independently differing lengths, widths or heights in any combination thereof. Further, the one or more raised ridges 923 may be disposed on opposing sides of the knife channel 530, or on any one side of the knife channel 530. Multiple one or more raised ridges 923 may be disposed symmetrically or asymmetrically about the knife channel 530. Multiple one or more raised ridges 923 may be disposed in a mutually parallel orientation to each other, or may not be disposed in a mutually parallel orientation to each other. While the one or more raised ridges 923 depicted in FIG. 9 are shown as linear ridges, such a shape is not limiting. Thus, alternative aspects of the one or more raised ridges 923 may include linear ridges, curved ridges, a combination of linear and curved ridges, or ridges including multiple linear and/or curved segments. Further, multiple one or more raised ridges 923 may have the same shape or differing shapes.

Additional features may include one or more raised bosses 915a-f wherein each of the raised bosses 915a-f extends vertically from a surface of one or more the raised ridges 923. It may be understood that the first electrode 920, the electrode surface 922, the one or more raised ridges 923, and the raised bosses 915a-f, may all be in mutual electrical communication. As a result, a voltage applied to the first electrode 920 may be equally applied to each of the first electrode surface 922, the one or more raised ridges 923, and the raised bosses 915a-f. Alternatively, one or more of the first electrode surface 922, the one or more raised ridges 923, and the raised bosses 915a-f may be electrically insulated from any of the other components of the first jaw assembly 919. It may also be understood that the components of the first jaw assembly 919 may be configured to contact a portion of a tissue when the first jaw member 909 is brought into a proximal position with respect to a second jaw member (for example, see 109b of FIG. 2). The components of the first jaw assembly 919 that may be configured to contact the portion of tissue may include any one or more of the first electrode surface 922, the one or more raised ridges 923, and the raised bosses 915a-f.

There may be a single raised boss 915 or there may be multiple raised bosses 915a-f. The raised bosses 915a-f may be placed along a single side of the first electrode 920 (for example, raised bosses 915a-f along an inner side of a U-shaped first electrode 920) or along multiple sides of the first electrode 920 (for example, along an inner side and along an outer side of a U-shaped first electrode 920). Multiple raised bosses 915a-f may have the same dimensions (for example length and/or width) or may have differing dimensions. In one non-limiting example, the pair of raised bosses 915a,d of the second electrode 920 that are proximate to a proximal joint in the end effector may be longer and/or wider than a pair of raised bosses 915b,e located in a medial section of the first electrode 920. Similarly, the pair of raised bosses 915b,e in a medial section of the first electrode 920 may be longer and/or wider than a pair of raised bosses 915c,f located in a distal section of the first electrode 920. It may be understood that no limitations are implied regarding the relative dimensions among the multiple raised bosses 915a-f. Multiple raised bosses 915a-f may be equally spaced along a side of the first electrode 920 or may be variably spaced along a side of the first electrode 920. The raised bosses 915a-f may have any shape appropriate to the function of the raised bosses 915a-f including, without limitation, a circular or partially circular shape, an elliptical or partially elliptical shape, an oval or partially oval shape, a square shape, or a rectangular shape. The raised bosses 515a-f may all have the same shape or may have differing shapes.

Each of the raised bosses 915a-f may be configured to engage one of the multiple insulating pads 215a-f (see FIG. 2) when the first jaw member 909 is moved proximate to the second jaw 109b. It may be understood that the term "engage" in this context may include forming a direct physical contact between a surface of a raised boss 915 and a surface of a mating insulating pad 215. However, the term "engage" in this context may also include a raised boss 915 and a mating insulating pad 215 being brought into a proximate but non-contacting position, for example when a piece of tissue is compressed between a raised boss 915 and a surface of a mating insulating pad 215 when the first jaw member 909 is moved proximate to the second jaw 109b.

Figure 11:
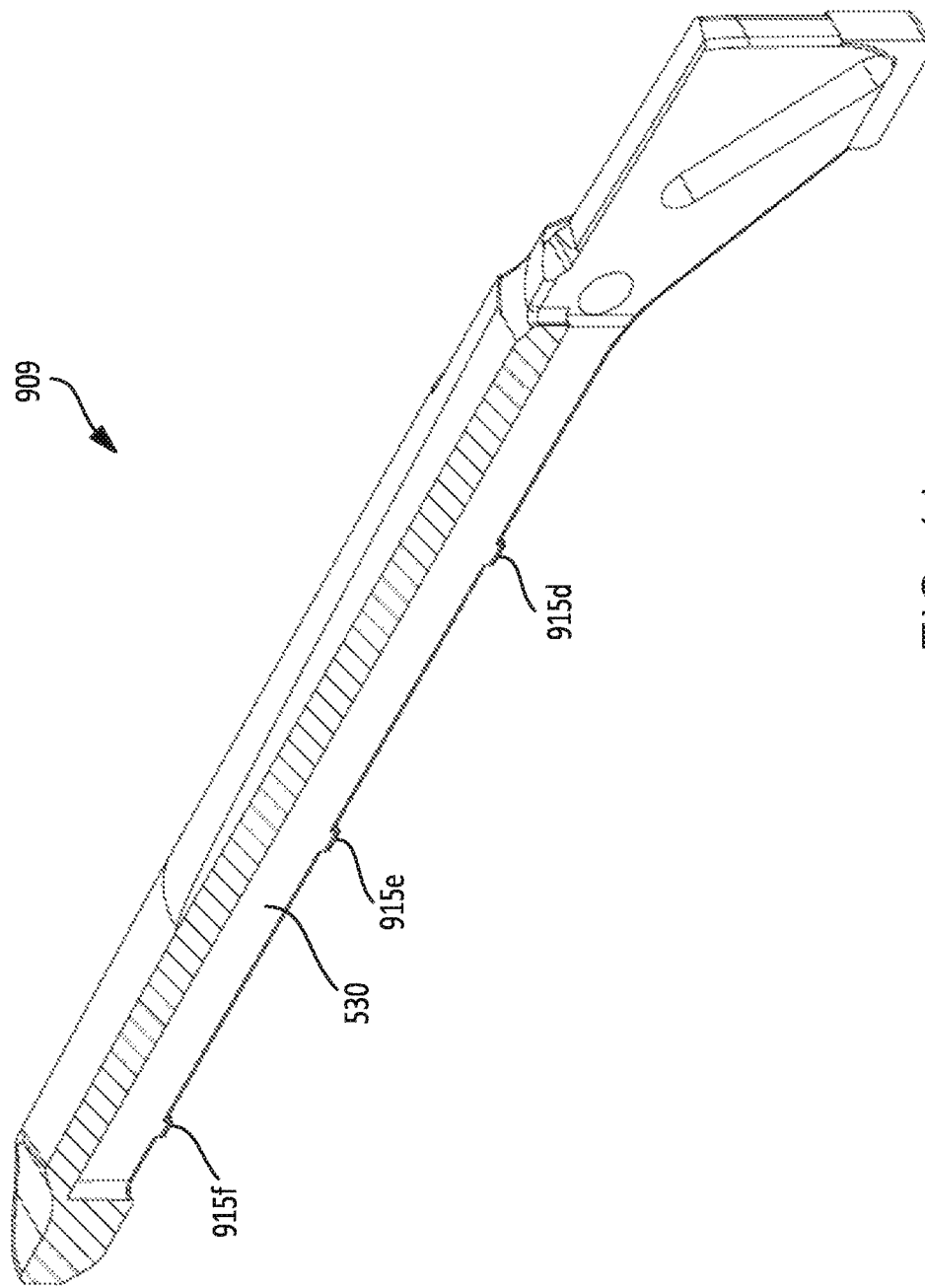
FIG. 11 is a longitudinal sectional view taken along line 11-11 of the aspect of the movable jaw depicted in FIG. 10C.
Figure 12:
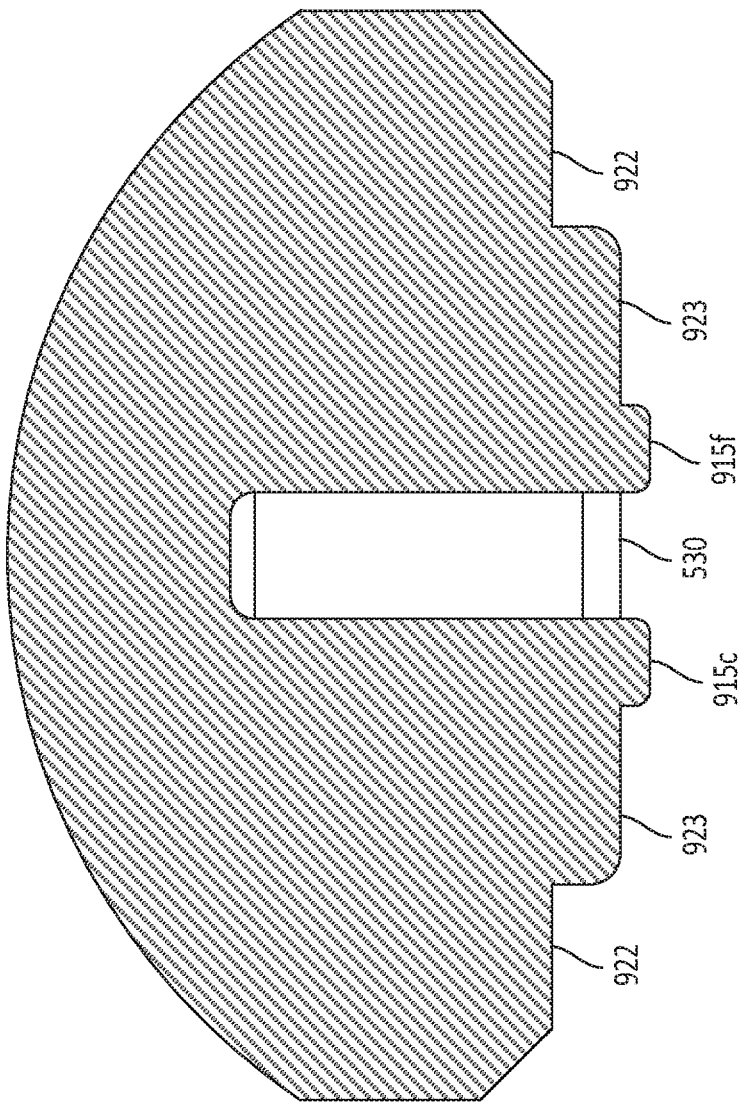
FIG. 12 is a transverse sectional view taken along line 12-12 of the aspect of the movable jaw depicted in FIG. 10C.

FIGS. 10A-C are top, side, and bottom plan views, respectively, of the example of the first jaw member 909 depicted in FIG. 9. FIG. 11 is a longitudinal cross-sectional view of the example of the first jaw member 909 depicted in FIG. 10C taken along line 11-11. The longitudinal cross-sectional view depicted in FIG. 11 particularly illustrates the knife channel 530 as well as cross-sectional views of the raised bosses 915d,e,f of first jaw member 909. FIG. 12 is a transverse cross-sectional view of the example of the first jaw member 509 depicted in FIG. 10C taken along line 12-12. The transverse cross-sectional view of FIG. 12 particularly illustrates the knife channel 530, cross-sectional views of raised bosses 915c,f, the essentially flat surface 522 of the first electrode of first jaw member 909 as well as the surface of the one or more raised ridges 923.

Figure 13:
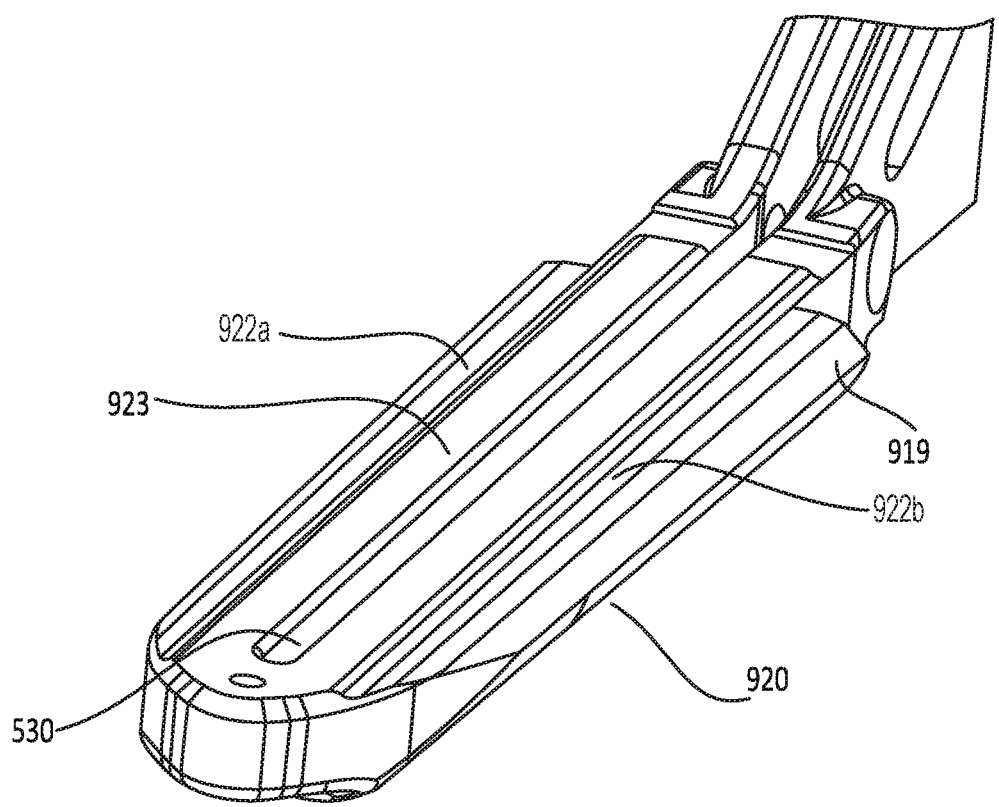
FIG. 13 illustrates a perspective view of a third aspect of a movable jaw of the end effector depicted in FIG. 2.

FIG. 13 depicts a perspective view of an alternative embodiment of the first jaw member depicted in FIG. 9. Similar to the working portion of the first jaw member 909 as depicted in FIG. 9, at least a portion of the surface 922 of the exemplary first electrode 920 may comprise a flat surface. The first jaw member 909 may also include a knife channel 530 through which a tissue cutting knife may reciprocate. Additionally, the first electrode 920 may incorporate features, for example one or more raised ridges 923 similar to those as depicted in FIG. 9. For example, the first electrode 920 may include a single, U-shaped raised ridge 923 vertically protruding above the surface 922 and which may surround the knife channel 530. Alternatively, the first electrode 920 may include multiple raised ridges 923. The raised ridges 923 may be placed along a single side of the first electrode 920 or along multiple sides of the first electrode 920. Multiple raised ridges 923 may have the same dimensions (for example vertical extent above the electrode surface 922) or may have differing dimensions. However, the first electrode 920 as depicted in FIG. 13 lacks the one or more raised bosses 915a-f extending vertically from a surface of one or more the raised ridges 923 as depicted in FIG. 9. It may be understood that the first electrode 920, the electrode surface 922, and the one or more raised ridges 923, may all be in mutual electrical communication.

Figure 14:
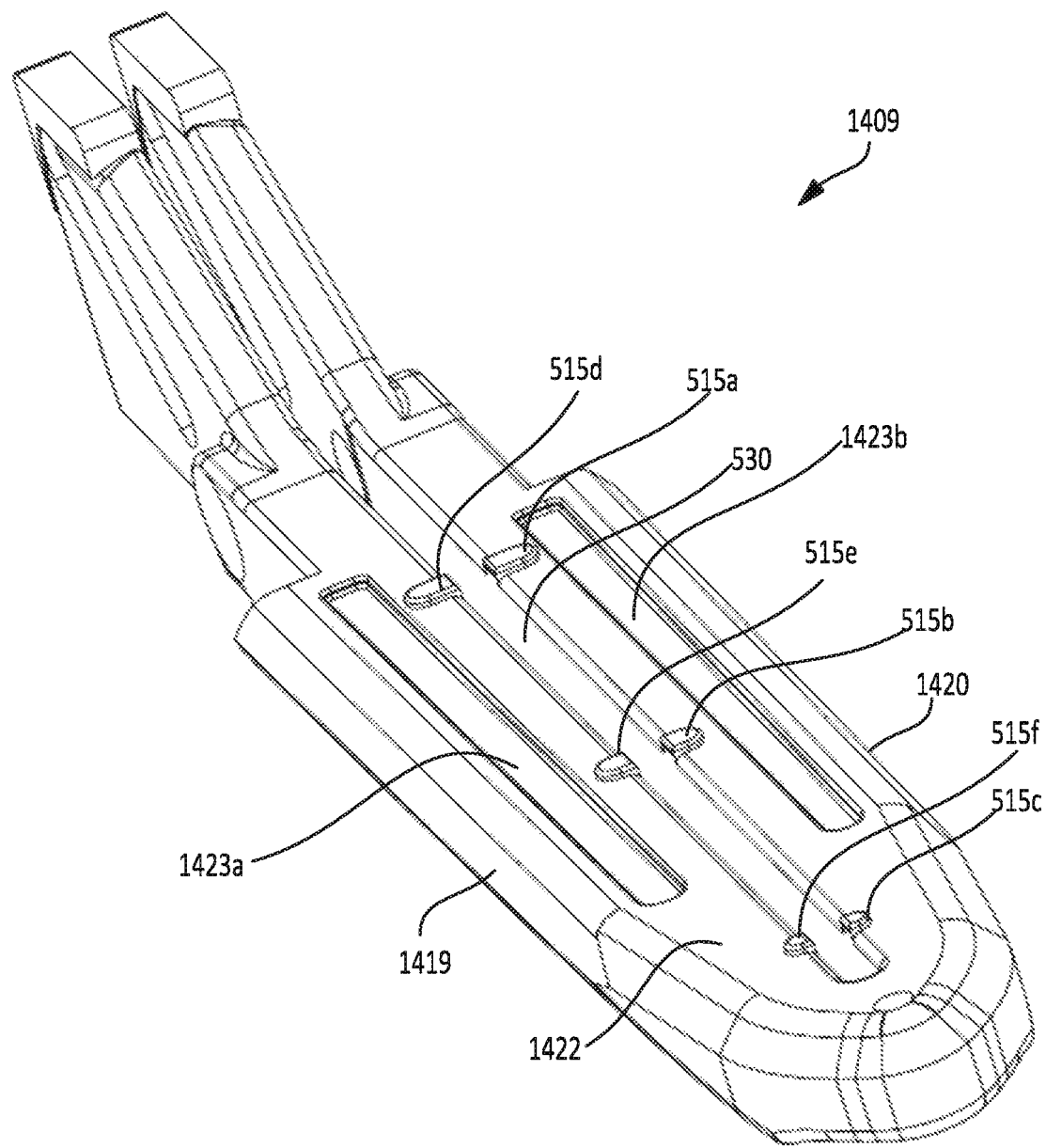
FIG. 14 illustrates a perspective view of a fourth aspect of a movable jaw of the end effector depicted in FIG. 2.

FIG. 14 is a perspective view of a first example of a first jaw member 1409 that may be incorporated into an end effector 108 (see FIG. 2) of an electrosurgical instrument 100 (see FIG. 1). The working portion of the first jaw member 1409 may include a first jaw assembly 1419 including a first electrode 1420 having a surface 1422 configured to contact a portion of a tissue when the first jaw member 1409 is brought into a proximal position with respect to a second jaw member (for example, see 109b of FIG. 2). As depicted in FIG. 14, the surface 1422 of the exemplary first jaw member 1409 may comprise a primarily flat surface. The first jaw member 1409 may also include a knife channel 530 through which a tissue cutting knife may reciprocate.

Additionally, the first electrode 1420 may incorporate features, for example one or more longitudinal channels 1423a,b that may be fabricated in a surface 1422 of the first electrode 1420. In the aspect depicted in FIG. 14, the first electrode 1420 includes multiple longitudinal channels 1423a,b vertically fabricated within the surface 1422. The longitudinal channels 1423a,b depicted in FIG. 14 are depicted as linear longitudinal channels 1423a,b extending along a longitudinal extent of the first electrode 1420. The linear longitudinal channels 1423a,b may be parallel to each other and may be parallel to, and on opposing sides of, the knife channel 530. It may be recognized that the depiction of the longitudinal channels 1423a,b in FIG. 14 is not considered limiting either in number, shape, length, depth, or width of the longitudinal channels 1423, or their disposition about the first electrode 1420. Thus, there may be one, two, three or any number of such longitudinal channels 1423. The longitudinal channels 1423 may have the same length, width, or depth or have independently differing lengths, widths or depths in any combination thereof. Further, the longitudinal channels 1423 may be disposed on opposing sides of the knife channel 530, or on any one side of the knife channel 530. Multiple longitudinal channels 1423 may be disposed symmetrically or asymmetrically about the knife channel 530. Multiple longitudinal channels 1423 may be disposed in a mutually parallel orientation to each other, or may not be disposed in a mutually parallel orientation to each other. While the longitudinal channels 1423 depicted in FIG. 14 are shown as linear channels, such a shape is not limiting. Thus, alternative aspects of the longitudinal channels 1423 may include linear channels, curved channels, a combination of linear and curved channels, or channels including multiple linear and/or curved segments. Further, multiple longitudinal channels 1423 may have the same shape or differing shapes.

Additionally, the first electrode 1420 may incorporate features including one or more raised bosses 515a-f. There may be a single raised boss 515 or there may be multiple raised bosses 515a-f. The raised bosses 515a-f may be placed along a single side of the first electrode 1420 (for example, raised bosses 515a-f along an inner side of a U-shaped first electrode 1420) or along multiple sides of the first electrode 1420 (for example, along an inner side and along an outer side of a U-shaped first electrode 1420). Multiple raised bosses 515a-f may have the same dimensions (for example length and/or width) or may have differing dimensions. In one non-limiting example, the pair of raised bosses 515a,d of the first electrode 1420 that are proximate to a proximal joint in the end effector may be longer and/or wider than a pair of raised bosses 515b,e located in a medial section of the first electrode 1420. Similarly, the pair of raised bosses 515b,e in a medial section of the first electrode 1420 may be longer and/or wider than a pair of raised bosses 515c,f located in a distal section of the first electrode 1420. It may be understood that no limitations are implied regarding the relative dimensions among the multiple raised bosses 515a-f. Multiple raised bosses 515a-f may be equally spaced along a side of the first electrode 1420 or may be variably spaced along a side of the first electrode 1420. The raised bosses 515a-f may have any shape appropriate to the function of the raised bosses 515a-f including, without limitation, a circular or partially circular shape, an elliptical or partially elliptical shape, an oval or partially oval shape, a square shape, or a rectangular shape. The raised bosses 515a-f may all have the same shape or may have differing shapes.

Each of the raised bosses 515a-f may be configured to engage one of the multiple insulating pads 215a-f (see FIG. 2) when the first jaw 109a is moved proximate to the second jaw 109b. It may be understood that the term "engage" in this context may include forming a direct physical contact between a surface of a raised boss 515 and a surface of a mating insulating pad 215. However, the term "engage" in this context may also include a raised boss 515 and a mating insulating pad 215 being brought into a proximate but non-contacting position, for example when a piece of tissue is compressed between a raised boss 515 and a surface of a mating insulating pad 215 when the first jaw 109a is moved proximate to the second jaw 109b.

Figure 16:
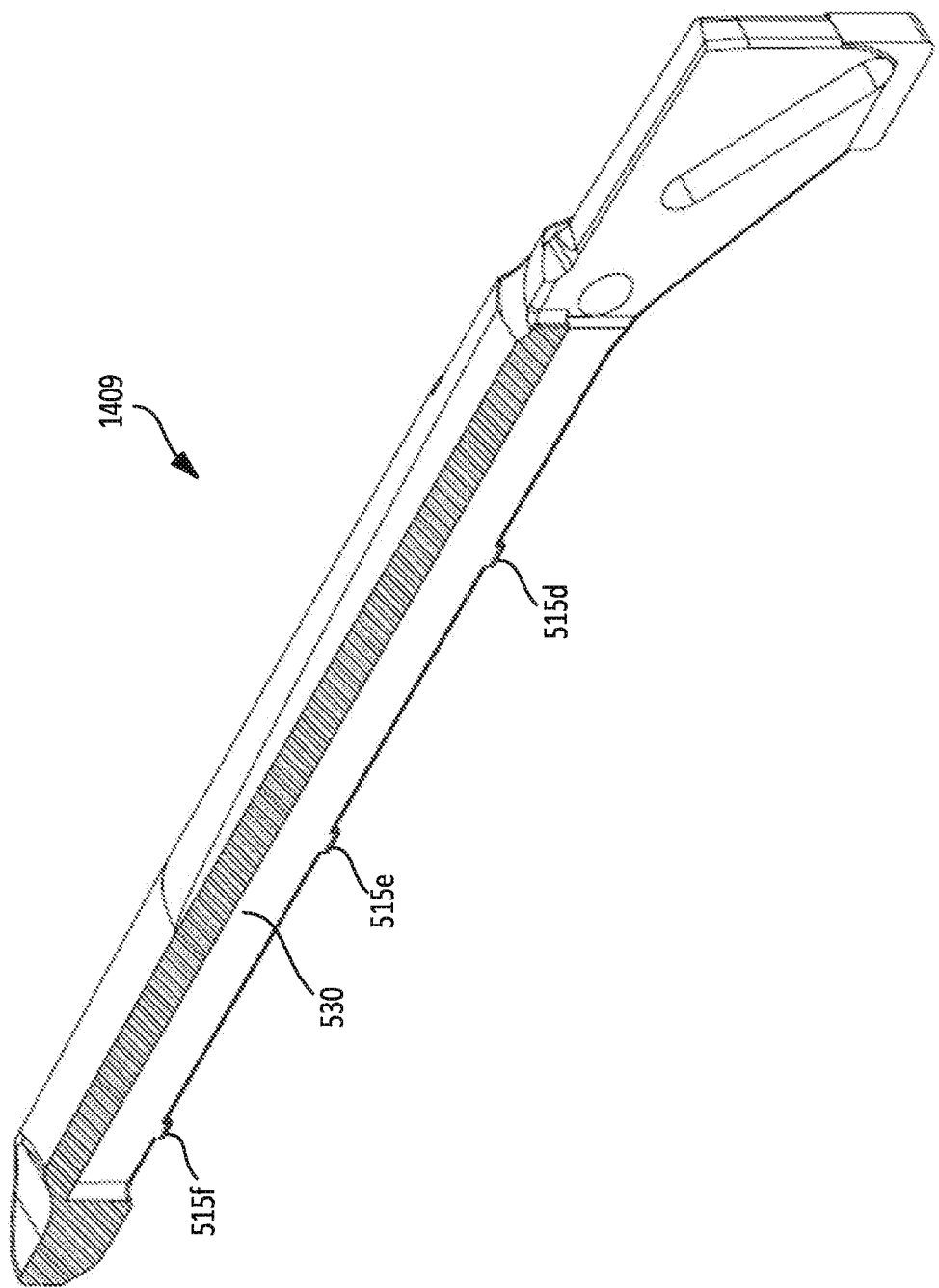
FIG. 16 is a longitudinal sectional view taken along line 16-16 of the aspect of the movable jaw depicted in FIG. 15C.
Figure 17:
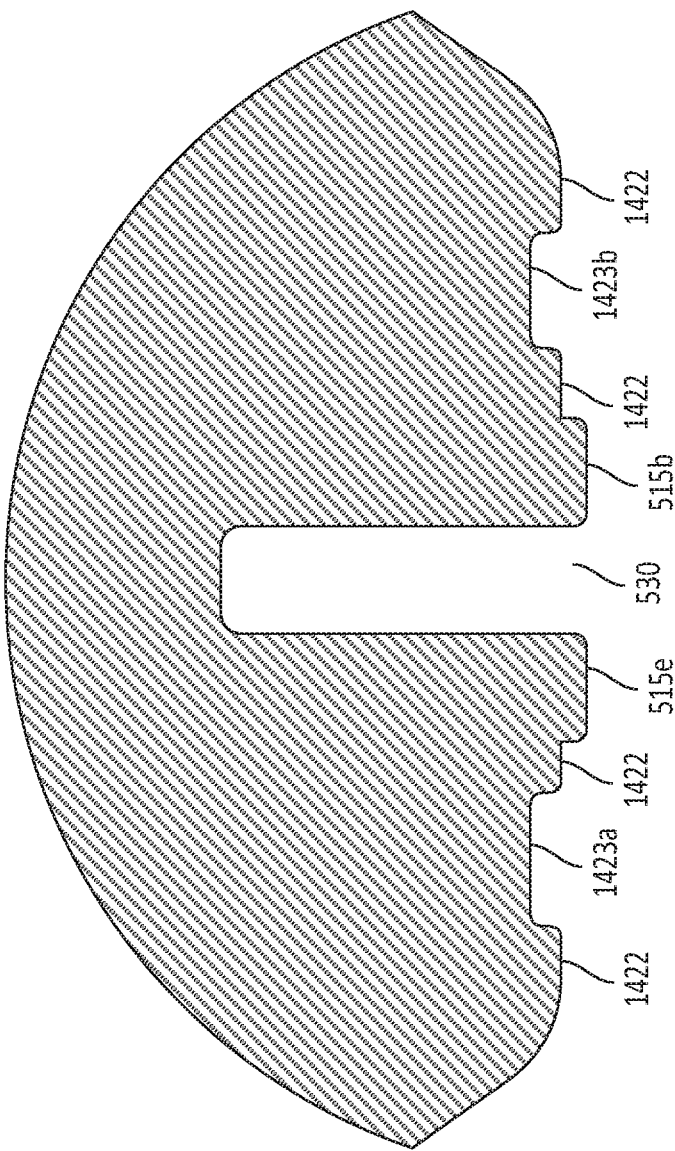
FIG. 17 is a transverse sectional view taken along line 17-17 of the aspect of the movable jaw depicted in FIG. 15C.

FIGS. 15A-C are top, side, and bottom plan views, respectively, of the example of the first jaw member 1409 depicted in FIG. 14. FIG. 16 is a longitudinal cross-sectional view of the example of the first jaw member 1409 depicted in FIG. 15C taken along line 16-16. The longitudinal cross-sectional view depicted in FIG. 16 particularly illustrates the knife channel 530 as well as cross-sectional views of the raised bosses 515d,e,f of first jaw member 1409. FIG. 17 is a transverse cross-sectional view of the example of the first jaw member 1409 depicted in FIG. 15C taken along line 17-17'. The transverse cross-sectional view of FIG. 17 particularly illustrates the knife channel 530, cross-sectional views of raised bosses 515b,e, the essentially flat surface 1422 of the first electrode 1420 of first jaw member 1409 as well as the surface of the one or more longitudinal channels 1423a,b.

Figure 18:
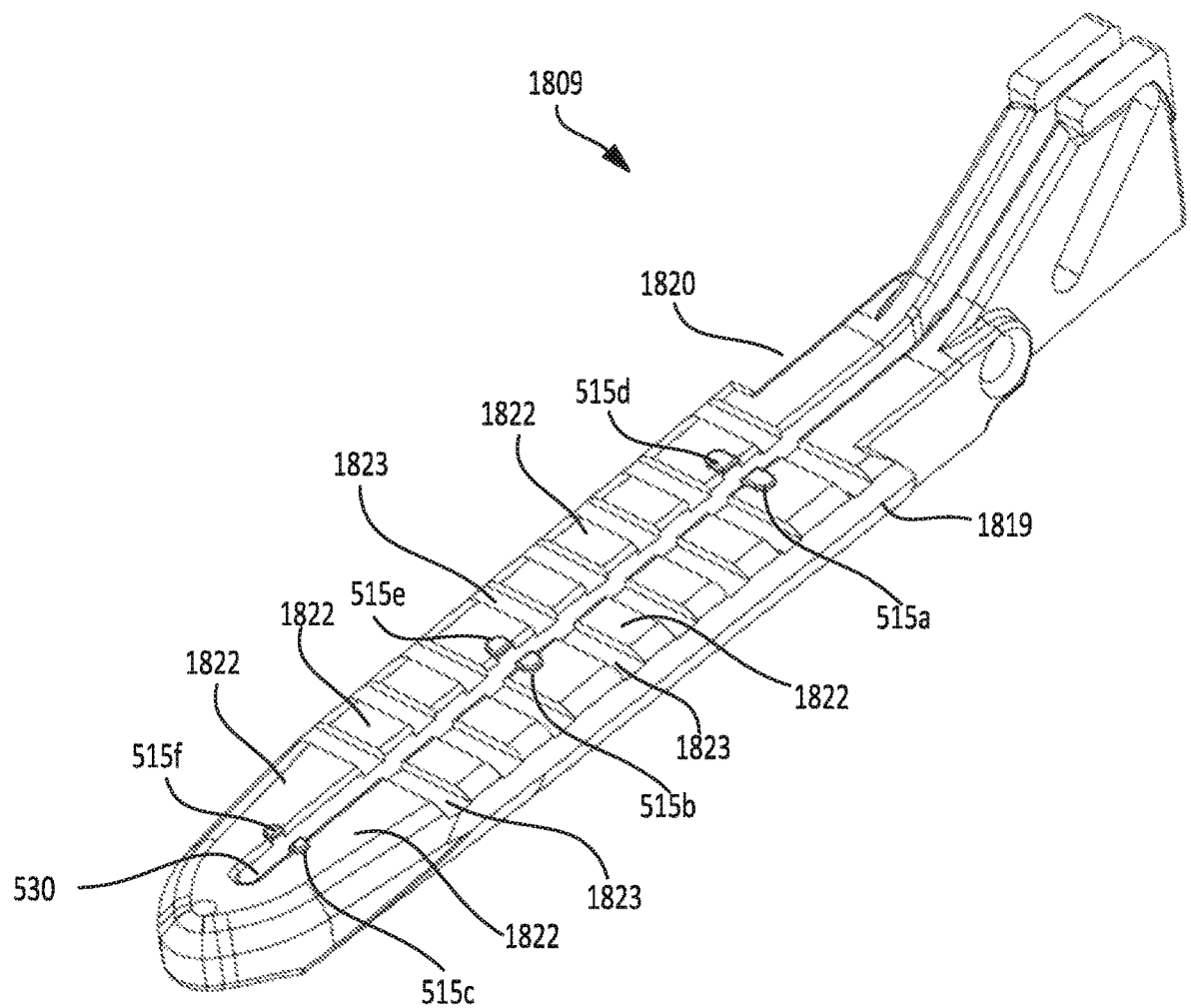
FIG. 18 illustrates a perspective view of a fifth aspect of a movable jaw of the end effector depicted in FIG. 2.

FIG. 18 is a perspective view of a first example of a first jaw member 1809 that may be incorporated into an end effector 108 (see FIG. 2) of an electrosurgical instrument 100 (see FIG. 1). The working portion of the first jaw member 1809 may include a first jaw assembly 1819 including a first electrode 1820 having a surface 1822 configured to contact a portion of a tissue when the first jaw member 1809 is brought into a proximal position with respect to a second jaw member (for example, see 109b of FIG. 2). As depicted in FIG. 18, the surface 1822 of the exemplary first jaw member 1809 may comprise a primarily flat surface. The first jaw member 1809 may also include a knife channel 530 through which a tissue cutting knife may reciprocate.

Additionally, the first electrode 1820 may incorporate features, for example one or more transverse channels 1823 that may be fabricated in a surface 1822 of the first electrode 1820. For the sake of clarity, not all of the transverse channels 1823 are labeled in FIG. 18. Nevertheless, one may understand that all such transverse channels depicted in FIG. 18, labeled or not, are included in this disclosure. In the aspect depicted in FIG. 18, the first electrode 1820 includes multiple transverse channels 1823 vertically fabricated within the surface 1822. The transverse channels 1823 depicted in FIG. 18 are depicted as linear transverse channels 1823 extending along a transverse extent of the first electrode 1820. The linear transverse channels 1823 may be parallel to each other and may be orthogonal to the knife channel 530. It may be recognized that the depiction of the transverse channels 1823 in FIG. 18 is not considered limiting either in number, shape, length, depth, or width of the transverse channels 1823, or their disposition about the first electrode 1820. Thus, there may be one, two, three or any number of such transverse channels 1823. The transverse channels 1823 may have the same length, width, or depth or have independently differing lengths, widths or depths in any combination thereof. Further, the transverse channels 1823 may be disposed on opposing sides of the knife channel 530, or on any one side of the knife channel 530. Multiple transverse channels 1823 may be disposed symmetrically or asymmetrically about the knife channel 530. Multiple transverse channels 1823 may be disposed in a mutually parallel orientation to each other, or may not be disposed in a mutually parallel orientation to each other. While the transverse channels 1823 depicted in FIG. 18 are shown as linear channels, such a shape is not limiting. Thus, alternative aspects of the transverse channels 1823 may include linear channels, curved channels, a combination of linear and curved channels, or channels including multiple linear and/or curved segments. Further, multiple transverse channels 1823 may have the same shape or differing shapes.

Additionally, the first electrode 1820 may incorporate features including one or more raised bosses 515a-f. There may be a single raised boss 515 or there may be multiple raised bosses 515a-f. The raised bosses 515a-f may be placed along a single side of the first electrode 1820 (for example, raised bosses 515a-f along an inner side of a U-shaped first electrode 1820) or along multiple sides of the first electrode 1820 (for example, along an inner side and along an outer side of a U-shaped first electrode 1820). Multiple raised bosses 515a-f may have the same dimensions (for example length and/or width) or may have differing dimensions. In one non-limiting example, the pair of raised bosses 515a,d of the first electrode 1820 that are proximate to a proximal joint in the end effector may be longer and/or wider than a pair of raised bosses 515*b,e* located in a medial section of the first electrode 1420. Similarly, the pair of raised bosses 515*b,e* in a medial section of the first electrode 1820 may be longer and/or wider than a pair of raised bosses 515*c,f* located in a distal section of the first electrode 1820. It may be understood that no limitations are implied regarding the relative dimensions among the multiple raised bosses 515*a-f*. Multiple raised bosses 515*a-f* may be equally spaced along a side of the first electrode 1820 or may be variably spaced along a side of the first electrode 1820. The raised bosses 515*a-f* may have any shape appropriate to the function of the raised bosses 515*a-f* including, without limitation, a circular or partially circular shape, an elliptical or partially elliptical shape, an oval or partially oval shape, a square shape, or a rectangular shape. The raised bosses 515*a-f* may all have the same shape or may have differing shapes.

Each of the raised bosses 515*a-f* may be configured to engage one of the multiple insulating pads 215*a-f* (see FIG. 2) when the first jaw 109*a* is moved proximate to the second jaw 109*b*. It may be understood that the term "engage" in this context may include forming a direct physical contact between a surface of a raised boss 515 and a surface of a mating insulating pad 215. However, the term "engage" in this context may also include a raised boss 515 and a mating insulating pad 215 being brought into a proximate but non-contacting position, for example when a piece of tissue is compressed between a raised boss 515 and a surface of a mating insulating pad 215 when the first jaw 109*a* is moved proximate to the second jaw 109*b*.

Figure 20:
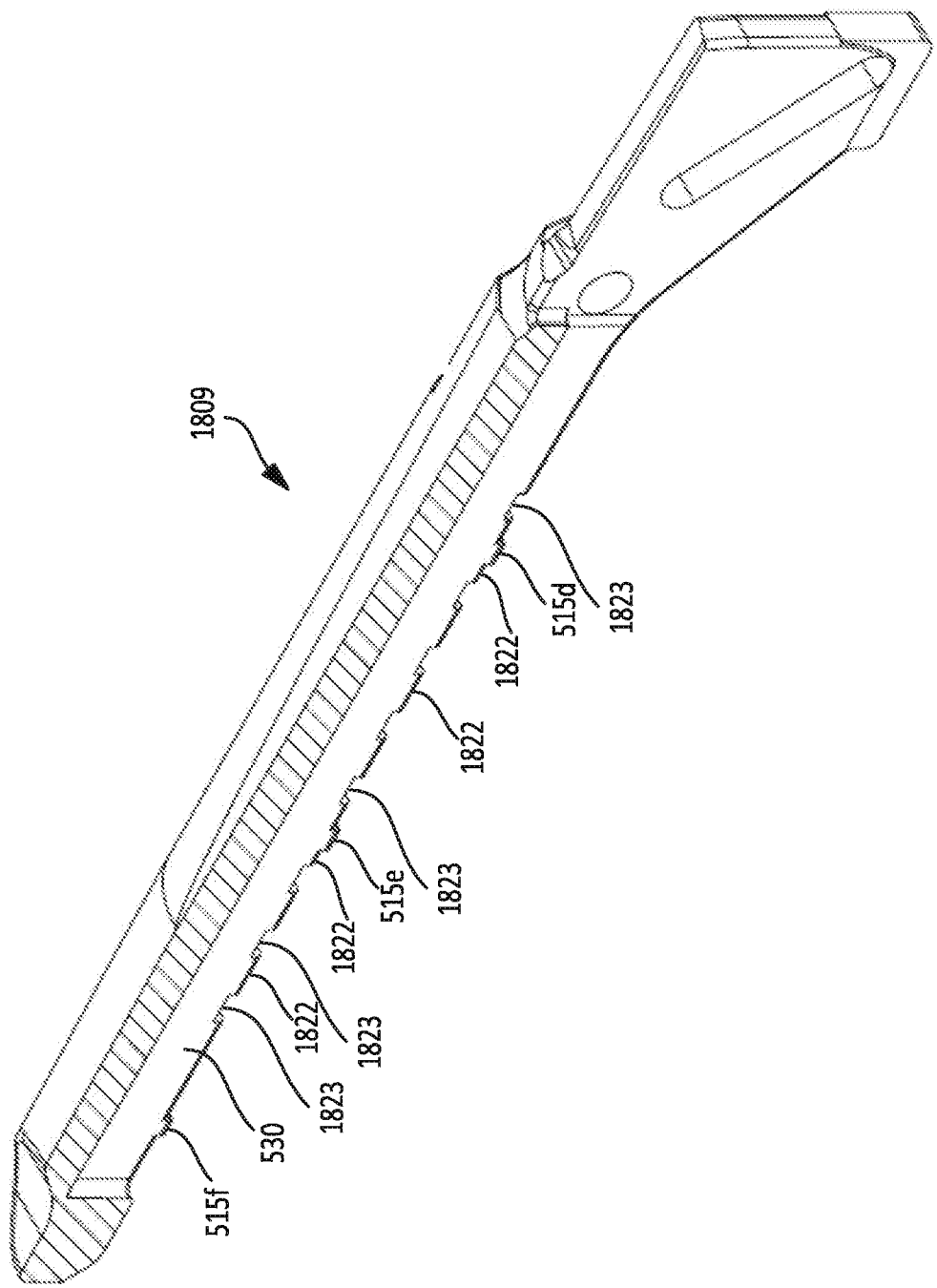
FIG. 20 is a longitudinal sectional view taken along line 20-20 of the aspect of the movable jaw depicted in FIG. 19C.
Figure 21A:
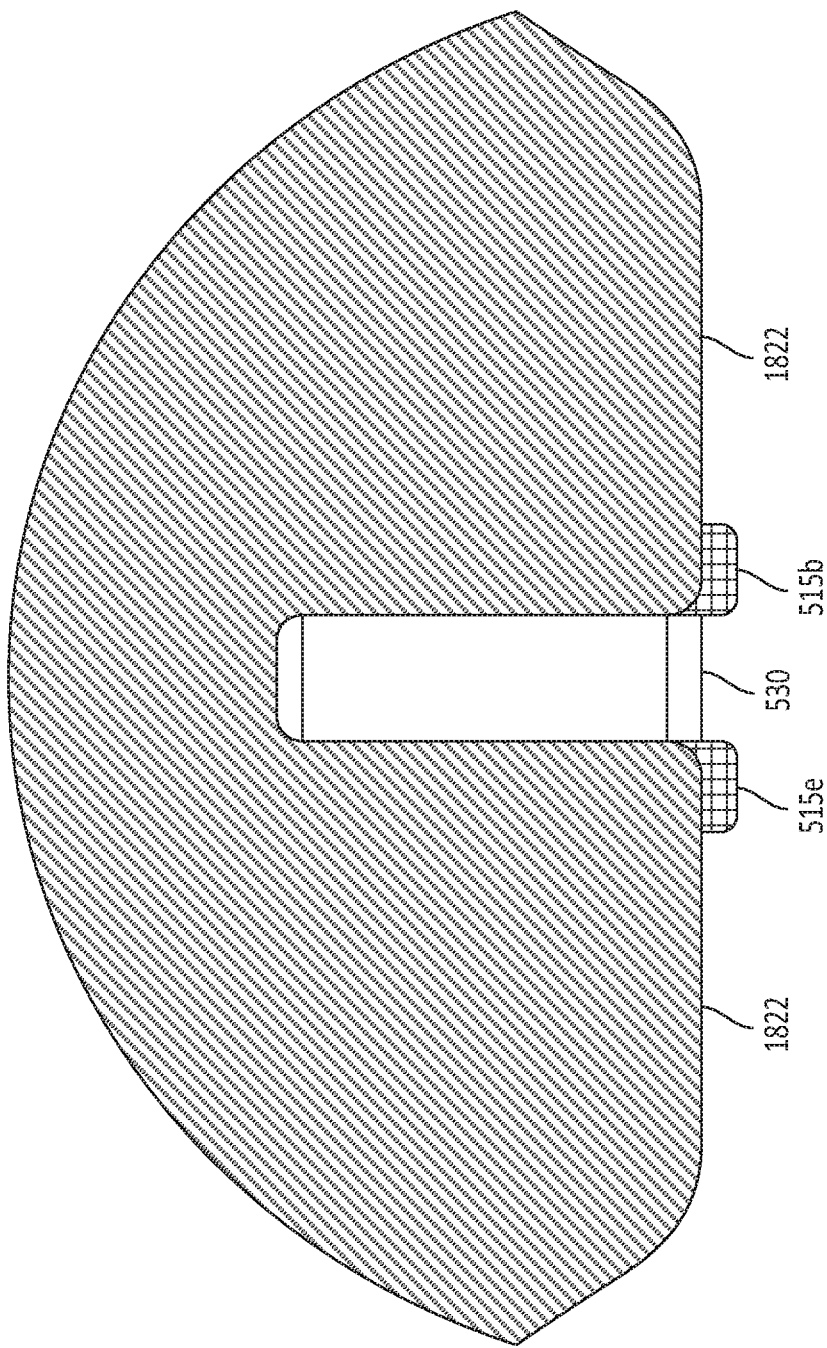
FIG. 21A is a transverse sectional view taken along line 21A-21A of the aspect of the movable jaw depicted in FIG. 19C.
Figure 21B:
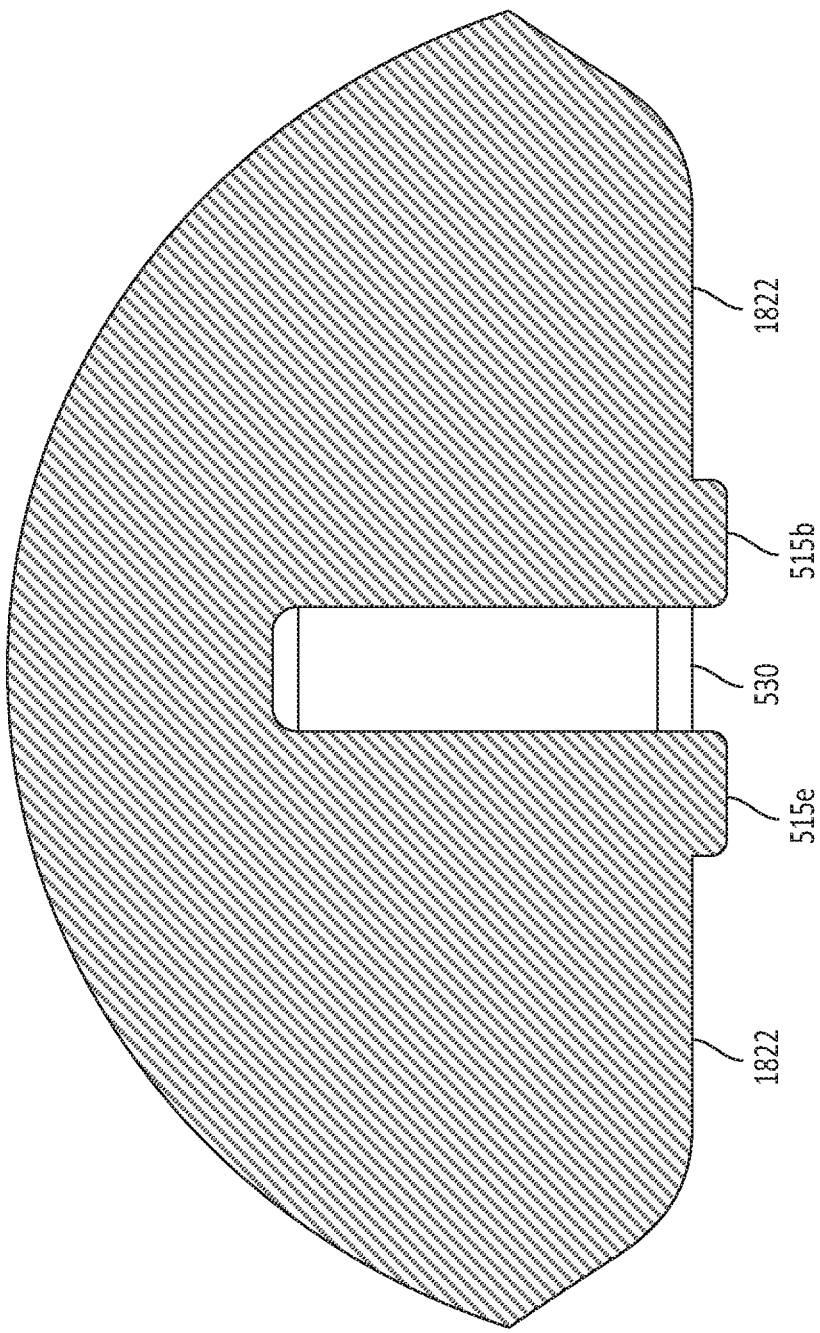
FIG. 21B is a transverse sectional view taken along line 21B-21B of the aspect of the movable jaw depicted in FIG. 19C.

FIGS. 19A-C are top, side, and bottom plan views, respectively, of the example of the first jaw member 1809 depicted in FIG. 18. FIG. 20 is a longitudinal cross-sectional view of the example of the first jaw member 1809 depicted in FIG. 19C taken along line 20-20. The longitudinal cross-sectional view depicted in FIG. 20 particularly illustrates the knife channel 530 as well as cross-sectional views of the raised bosses 515*d,e,f* of first jaw member 1809. Further, FIG. 20 also depicts, in cross-sectional view, multiple transverse channels 1823 taken along with views of the surface 1822 of the first electrode 1820. FIGS. 21A-C depict various transverse cross-sectional views of the example of the first jaw member 1809 depicted in FIG. 19C taken along lines 21A-21A, 21B-21B, and 21C-21C, respectively. The transverse cross-sectional view of FIG. 21A particularly illustrates the knife channel 530 and the essentially flat surface 1822 of the first electrode 1820 of first jaw member 1809. The transverse cross-sectional view of FIG. 21B particularly illustrates the knife channel 530, the essentially flat surface 1822 of the first electrode 1820 of first jaw member 1809, and the raised bosses 515*b,e*. The transverse cross-sectional view of FIG. 21C particularly illustrates the knife channel 530 and the recessed surface of transverse channel 1823 with respect to the essentially flat surface 1822 of the first electrode 1820 of first jaw member 1809.

FIGS. 5-21C and their descriptions as disclosed above present a plurality of aspects of a first jaw member 109*a* comprising a plurality of features, the features configured to form a plurality of textures in the surface of the first jaw member 109*a* and/or its respective first electrode 220*a*. Although a plurality of aspects of such features have been disclosed herein, such aspects are not to be construed as limiting. Thus, the features may include any appropriate features that may be configured to form a texture on a surface of a jaw member or an electrode. The features may generally include raised or elevated features that extend vertically above a surface of the electrode, or depressed features that extend vertically below a surface of the electrode. No limitations, expressed or implied, are herein imposed on methods of fabricating the features.

The features may include a single feature or multiple features. The single feature or multiple features may have a limited extent, such as a boss (a raised feature) or a pit (a depressed feature). The single feature or multiple features may have a more extended extent such as a ridge (a raised feature) or a channel (a depressed feature). The single feature or multiple features—either of limited extent or of extended extent—are not limited in their respective shapes, sizes, or dimensions. The single feature or multiple features—either of limited extent or of extended extent—are not limited in their respective dispositions about the surface of the electrode. Thus, as an example, a ridge or a channel (a feature having an extended extent) may extend along an axis essentially parallel to a longitudinal axis of the first electrode, thereby comprising a longitudinal ridge or a longitudinal channel, respectively. Alternatively, a ridge or a channel (a feature having an extended extent) may extend along an axis essentially perpendicular to a longitudinal axis of the first electrode, thereby comprising a transverse ridge or a transverse channel, respectively. In yet another alternative example, a ridge or a channel (a feature having an extended extent) may extend along an axis neither essentially parallel to nor essentially perpendicular to a longitudinal axis of the first electrode, thereby comprising an oblique ridge or an oblique channel, respectively.

Multiple features may include any combination or combinations of elevated and/or depressed features. Multiple features may be combined. For example, in reference to FIG. 9, a ridge, such as longitudinal ridge 923, may include additional features such as raised bosses 915*a-f* extending vertically from a surface of the longitudinal ridge 923. It may be recognized that one or more ridges essentially perpendicular to a longitudinal axis of the electrode (one or more transvers ridges) may also include additional features such as raised bosses extending vertically from a surface of the transverse ridge. It may also be recognized that one or more ridges neither essentially perpendicular to nor parallel to a longitudinal axis of the electrode (one or more oblique ridges) may also include additional features such as raised bosses extending vertically from a surface of the oblique ridge. Similarly, a channel, (for example a longitudinal channel, a transverse channel, or an oblique channel) having a first depth may also include, on an inner surface, a second channel having a second depth. Further, multiple features may be symmetrically disposed about the surface of the electrode or they may be asymmetrically disposed about the surface of the electrode. Multiple features—either of limited extent or of extended extent—are not limited in their dispositions about the surface of the electrode with respect to each other.

As disclosed above, and depicted in FIGS. 1-21C, an end effector may include a first jaw member and a second jaw member. In aspects disclosed above, the first jaw member may be an upper jaw member configured to move relative to a second jaw member comprising a lower jaw member when a force is applied to the end effector, wherein the second jaw member is in a relatively fixed geometry with respect to an elongated shaft. Aspects disclosed above include features configured to provide a texture to a surface (such as an electrode surface) associated with the upper and movable first jaw member. Additionally, aspects disclosed above include an essentially flat electrode comprising an electrode assembly layer associated with the lower and relatively fixed second jaw member. It may be understood that alternative aspects include a jaw assembly in which the upper jaw member is relatively fixed with respect to an elongated shaft and the lower jaw member may be configured to move relative to the fixed upper jaw member when a force is applied to the end effector. It may further be understood that the plurality of features disclosed above may be associated with the fixed jaw member as opposed to the movable jaw member. Similarly, it may be understood that the electrode assembly layer may be associated with the movable jaw member as opposed to the fixed jaw member.

As disclosed above, and depicted in FIGS. 1-21C, a end effector may include a first jaw member and a second jaw member, in which the first jaw member may include a first electrode having a first electrode surface and the second jaw member may include a second electrode having a second electrode surface. The first electrode may be placed in electrical communication with a first terminal of an RF current generator, and the second electrode may be placed in electrical communication with a second terminal of the RF current generator. It may be understood that the first electrode, the first electrode surface, and any one or more features—including, without limitation, one or more raised ridges, one or more channels, and one or more raised bosses—may all be in mutual electrical communication and in electrical communication with the first terminal of the RF current generator. As a result, a voltage applied to the first electrode may be equally applied to each of the first electrode surfaces and each of the one or more features, including the one or more raised ridges, the one or more channels, and the one or more raised bosses.

Figure 22:
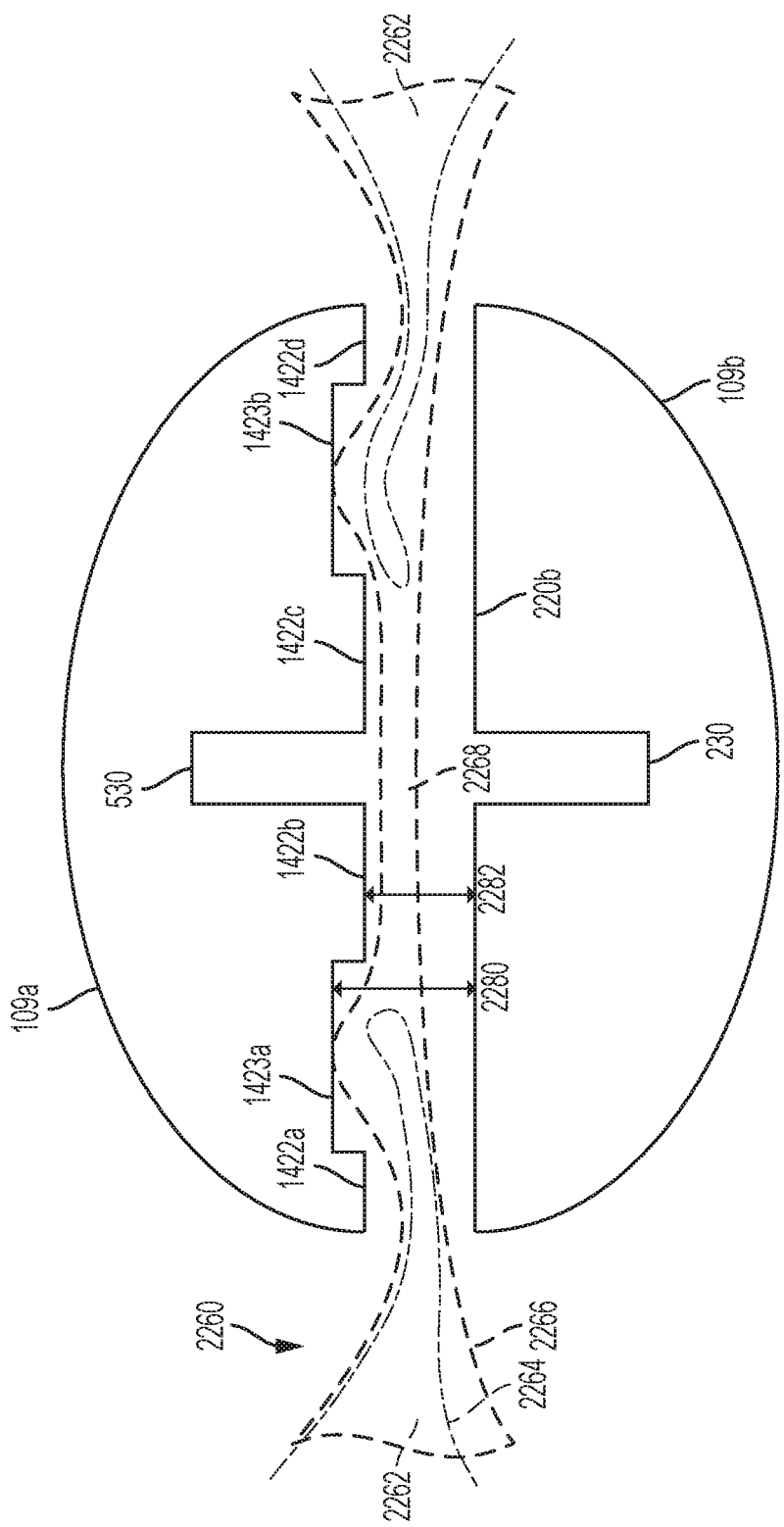
FIG. 22 is a cross-sectional view of one aspect of the end effector of the electrosurgical instrument of FIGS. 1A and 1B with the jaws closed and compressing a blood vessel therebetween.
Figure 23:
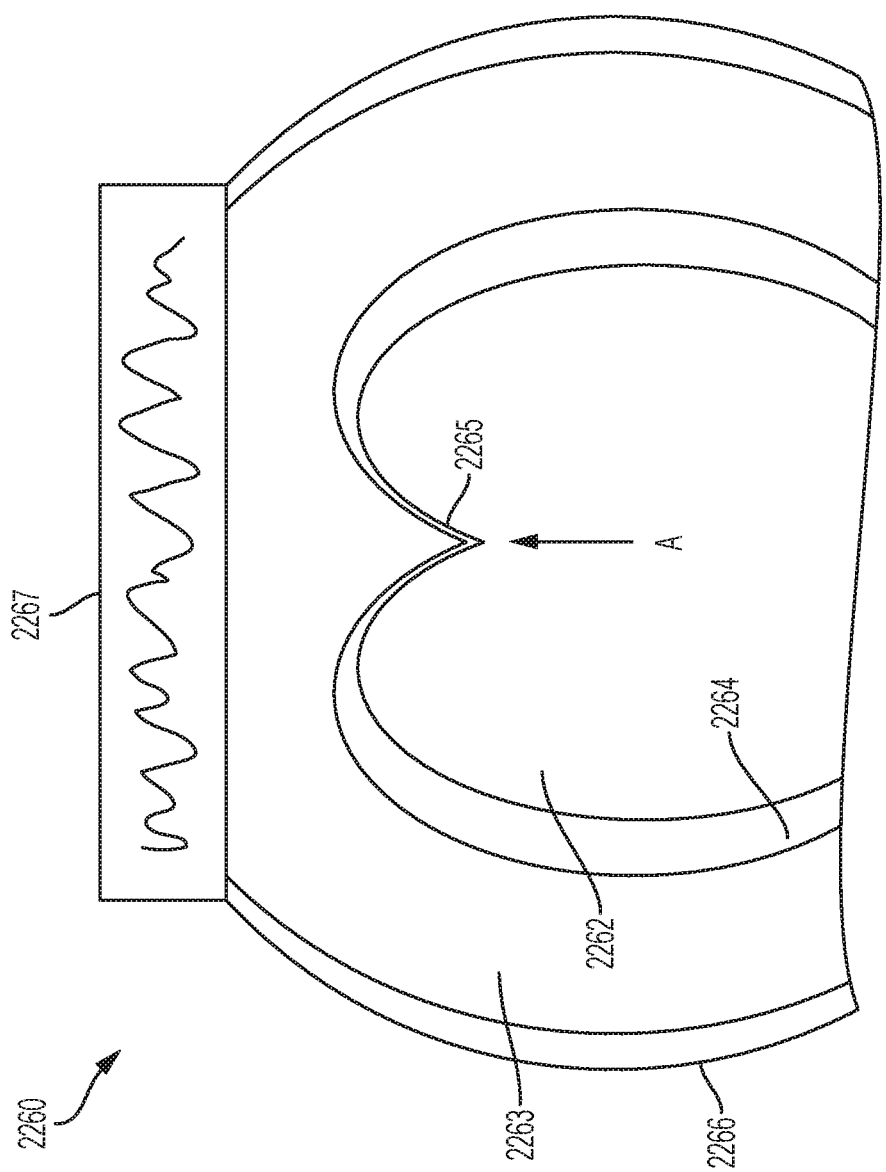
FIG. 23 is a cross-sectional view of one aspect of a blood vessel after a sealing operation has been applied by the electrosurgical instrument of FIGS. 1A and 1B.

FIGS. 22 and 23 depict aspects of effects of the use of a surgical instrument having a textured jaw on an exemplary blood vessel. FIG. 22 depicts a cross-sectional view of a blood vessel 2260 clamped between a first jaw assembly 109a and a second jaw assembly 109b of a surgical instrument. The blood vessel 2260 may comprise a lumen 2262 bounded by an intima 2264, a smooth muscle layer or tunica media, and an outer layer or adventitia 2266. The first jaw assembly 109a is moved to a proximate position with respect to the second jaw assembly 109b and the blood vessel 2260 is compressed therebetween. In FIG. 22, the first jaw assembly 109a comprises a first electrode 1420 similar to that depicted in FIG. 14, and a second jaw assembly 109b that comprises an electrode 109b similar to that depicted in FIG. 3. Thus, FIG. 22 depicts the surface 1422a,b,c,d of the first electrode as well as recessed surfaces of the longitudinal channels 1423a,b. FIG. 22 also depicts the surface of the second electrode 220b. Additionally FIG. 22 depicts the relative positions of the knife channel 530 associated with the first electrode 109a and the knife channel 230 associated with the second electrode 109b. For clarity, FIG. 22 omits the raised bosses 515 of first electrode 1420 or insulating pads 215 of the second jaw assembly 109b.

As depicted in FIG. 22, a portion of the blood vessel 2260 clamped between the first jaw assembly 109a and the second jaw assembly 109b may be deformed so that a portion of the lumen 2262 may be in a compressed state but still patent, for example the portion of the blood vessel 2260 disposed between the channels 1423a,b of the first jaw assembly 109a and the surface of the second electrode 220b. Alternatively, the lumen 2262 may be completely sealed 2268, for example in the portion the blood vessel 2260 between the surface 1422b,c of the first electrode and the surface of the second electrode 220b.

If the blood vessel 2260 is considered a deformable Hook's law solid, then a compressive force imparted to it by the first jaw assembly 109a and the second jaw assembly 109b is proportional to an amount of physical deformation of the blood vessel 2260. The amount of deformation of the blood vessel 2260, in turn, may be related to the distance between the first electrode 220a or any of its features and the second electrode 220b. For example, as depicted in FIG. 22, the distance 2280 between the bottom surface of channel 1423a and the surface of the second electrode 220b is greater than the distance 2282 between the surface of the first electrode 1422b and the surface of the second electrode 220b. As a result, the amount of deformation of the blood vessel 2260 compressed by the surface of channel 1423a is less than that of the blood vessel 2260 compressed by the surface of first electrode 1422b, and thus the compressive force produced at the channel 1423a is less than that produced at the first electrode 1422b. It may be understood that specific the deformations to the blood vessel 2260 depicted in FIG. 22 may result from the specific shape of the electrode 1420 and its features (for example the longitudinal channels 1423a,b).

However, it should be recognized that a blood vessel 2260 clamped between a first jaw assembly 109a having alternative features and the second jaw assembly 109b may include alternative deformations arising from the geometry of those alternative features of the first electrode. For example, a first jaw assembly 909 as depicted in FIG. 9 comprises ridges 923 and raised bosses 915a-f. It may be understood that a portion of a blood vessel compressed between first jaw assembly 909 and the second jaw assembly 109b may experience greater compressive forces between the ridges 923 and/or the raised bosses 915a-f and the second electrode 220b than between the surface 922 of the first electrode 920 and the second electrode 220b. Such greater compressive forces may arise because the distance between the raised features (the ridges 923 and/or the raised bosses 915a-f) and the surface of the second electrode 220b is less than the distance between the surface 922 of the first electrode 920 and the surface of the second electrode 220b.

FIG. 23 depicts the results of the application of the surgical instrument on the blood vessel 2260. It may be observed that the lumen 2262 is generally patent and that the intima 2264, the smooth muscle layer or tunica media 2263, and the outer layer or adventitia 2266 have all assumed the generally circular cross-sectional geometry of a normal blood vessel 2260. Without being bound by theory, the result of the application of the surgical instrument may be observed in the adventitial seal 2267 that closes the wall of the blood vessel 2260. The intima 2264 may also include structures 2265 resulting from the sealing process that may act to mechanically strengthen the adventitial seal 2267 against the transverse force of blood (arrow A) developed during a cardiac systolic pumping motion.

Figure 24:
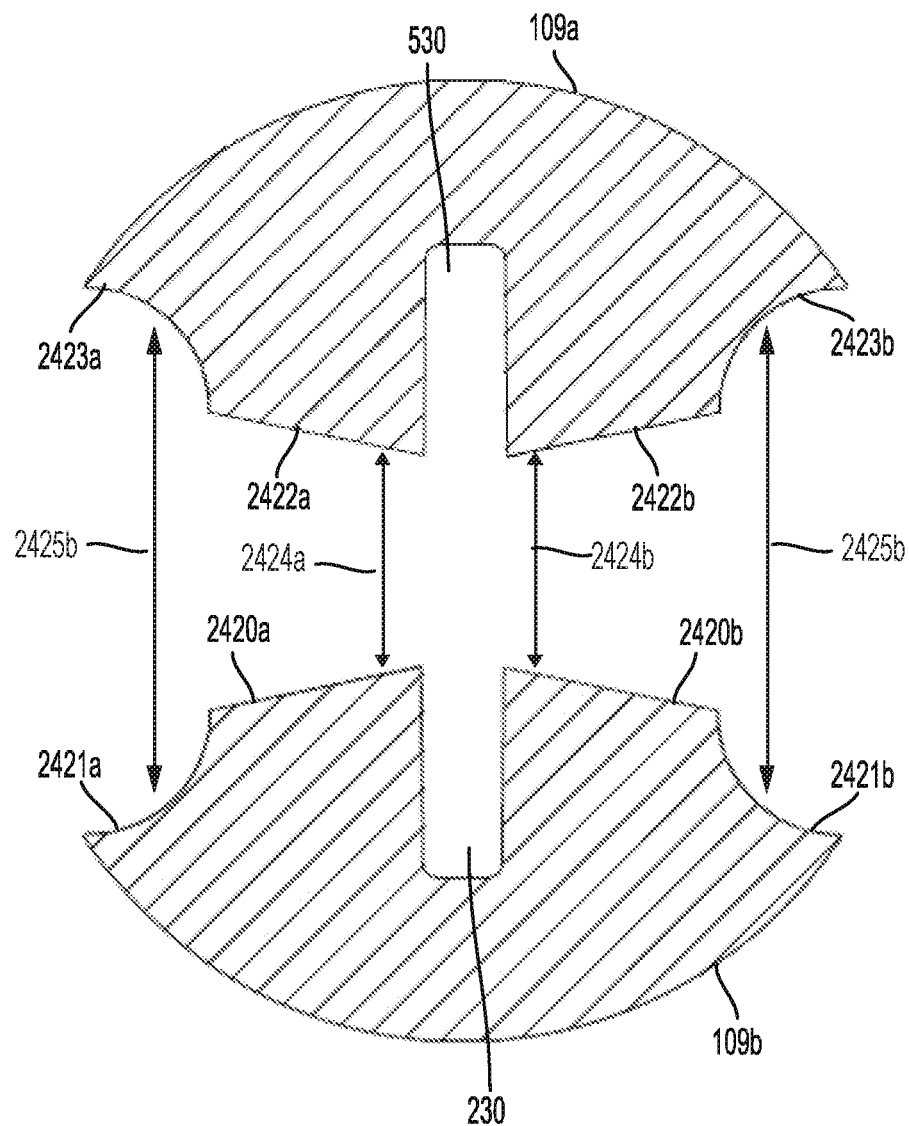
FIG. 24 is a cross-sectional view of an end effector of the electrosurgical instrument of FIGS. 1A and 1B in which the first jaw and the second jaw include interior tapered portions and external concave portions.

FIG. 24 depicts a cross-sectional view of an aspect of an end effector in which both the first jaw member 109a and the second jaw member 109b may include complementary features configured to mold a shape of a blood vessel during compression and cauterization. The first jaw member 109a may include a knife channel 530 through which a tissue cutting knife may reciprocate. Similarly, the second jaw member 109b may include a knife channel 230 through which the tissue cutting knife may reciprocate.

In the aspect depicted in FIG. 24, at least a portion of the first electrode may comprise one or more first tapered portions 2422a,b. The first tapered portions 2422a,b may be disposed in one or more interior sections of the first jaw member 109a, for example proximate to the knife channel 530. In the aspect depicted in FIG. 24, at least a portion of the second electrode may comprise one or more second tapered portions 2420a,b. The second tapered portions 2420a,b may be disposed in one or more interior sections of the second jaw member 109b, for example proximate to the knife channel 230. When the first jaw member 109a and the second jaw member 109b are placed in a proximate position, for example when compressing a blood vessel therebetween, a compression zone comprising a first tapered space 2424a and a second tapered space 2424b may be formed. The first tapered space 2424a may be bounded by first tapered portion 2422a and second tapered portion 2420a, and a second tapered space 2424b, may be bounded by first tapered portion 2422b and second tapered portion 2420b. The first tapered space 2424a may have a wider spacing towards the exterior of the jaw members 109a,b than a spacing towards the interior of the jaw members 109a,b. Similarly, the second tapered space 2424b may have a wider spacing towards the exterior of the jaw members 109a,b than a spacing towards the interior of the jaw members 109a,b. The first tapered portions 2422a,b may be in electrical communication with a conductor providing electrical energy to the first jaw member 109a and the second tapered portions 2420a,b may be in electrical communication with a conductor providing electric energy to the second jaw member 109b.

The tapered portions 2422a,b depicted in FIG. 24 may extend along the entire length of the first jaw member 109a or only along a portion of the length of first jaw member 109a. Further, first jaw member 109a may include multiple tapered portions, each tapered portion extending along a partial length of the first jaw member 109a. Although the tapered portions 2422a,b depicted in FIG. 24 may have a linear taper, the tapered portions 2422a,b may include alternative tapers, such as curved tapers. Additionally, the tapered portions 2420a,b depicted in FIG. 24 may extend along the entire length of the second jaw member 109b or only along a portion of the length of second jaw member 109b. Further, second jaw member 109b may include multiple tapered portions, each tapered portion extending along a partial length of the second jaw member 109b. Although the tapered portions 2420a,b depicted in FIG. 24 may have a linear taper, the tapered portions 2420a,b may include alternative tapers, such as curved tapers.

In the aspect depicted in FIG. 24, at least a portion of the first electrode may further comprise one or more first concave portions 2423a,b. The first concave portions 2423a,b may be disposed adjacent to an exterior section of the first jaw member 109a, for example proximate to the exterior edges of the first jaw member 109a. In some aspects, the first concave portion 2423a may be proximal to the first tapered portion 2422a; similarly the first concave portion 2423b may be proximal to the first tapered portion 2422b. In the aspect depicted in FIG. 24, at least a portion of the second electrode may comprise one or more second concave portions 2421a,b. The second concave portions 2421a,b may be disposed adjacent to an exterior section of the second jaw member 109b, for example proximate to the exterior edges of the second jaw member 109b. In some aspects, the second concave portion 2421a may be proximal to the second tapered portion 2420a; similarly the second concave portion 2421b may be proximal to the second tapered portion 2420b.

When the first jaw member 109a and the second jaw member 109b are placed in a proximate position, for example when compressing a blood vessel therebetween, a first mold zone 2425a and a second mold zone 2425b may be formed. The first mold zone 2425a may be bounded by first concave portion 2423a and second concave portion 2421a, and a second mold zone 2425b, may be bounded by first concave portion 2423b and second concave portion 2421b. The first concave portions 2423a,b may be in electrical communication with a conductor providing electrical energy to the first jaw member 109a and the second concave portions 2421a,b may be in electrical communication with a conductor providing electric energy to the second jaw member 109b. Alternatively, the first concave portions 2423a,b may not be in electrical communication with a conductor providing electrical energy to the first jaw member 109a. Additionally, the second concave portions 2421a,b may not be in electrical communication with a conductor providing electrical energy to the first jaw member 109b. Concave portions 2423a,b and/or concave portions 2421a,b that are not in electrical communication with conductors providing electrical energy to the first jaw member 109a and/or second jaw member 109b, may nevertheless be in thermal communication with their respective tapered portions (2422a,b and 2420a,b, respectively). Thus, concave portion 2423a may be in thermal communication with tapered portion 2422a, concave portion 2423b may be in thermal communication with tapered portion 2422b, concave portion 2421a may be in thermal communication with tapered portion 2420a, and concave portion 2421b may be in thermal communication with tapered portion 2420b.

The concave portions 2423a,b depicted in FIG. 24 may extend along the entire length of the first jaw member 109a or only along a portion of the length of first jaw member 109a. Further, first jaw member 109a may include multiple concave portions, each concave portion extending along a partial length of the first jaw member 109a. Although the concave portions 2423a,b depicted in FIG. 24 may have a curved geometry, the concave portions 2423a,b may include geometry, such as a linear geometry. Additionally, the concave portions 2421a,b depicted in FIG. 24 may extend along the entire length of the second jaw member 109b or only along a portion of the length of second jaw member 109b. Further, second jaw member 109b may include multiple concave portions, each concave portion extending along a partial length of the second jaw member 109b. Although the concave portions 2421a,b depicted in FIG. 24 may have a curved geometry, the concave portions 2421a,b may include alternative geometries, such as a linear geometry.

Figure 25:
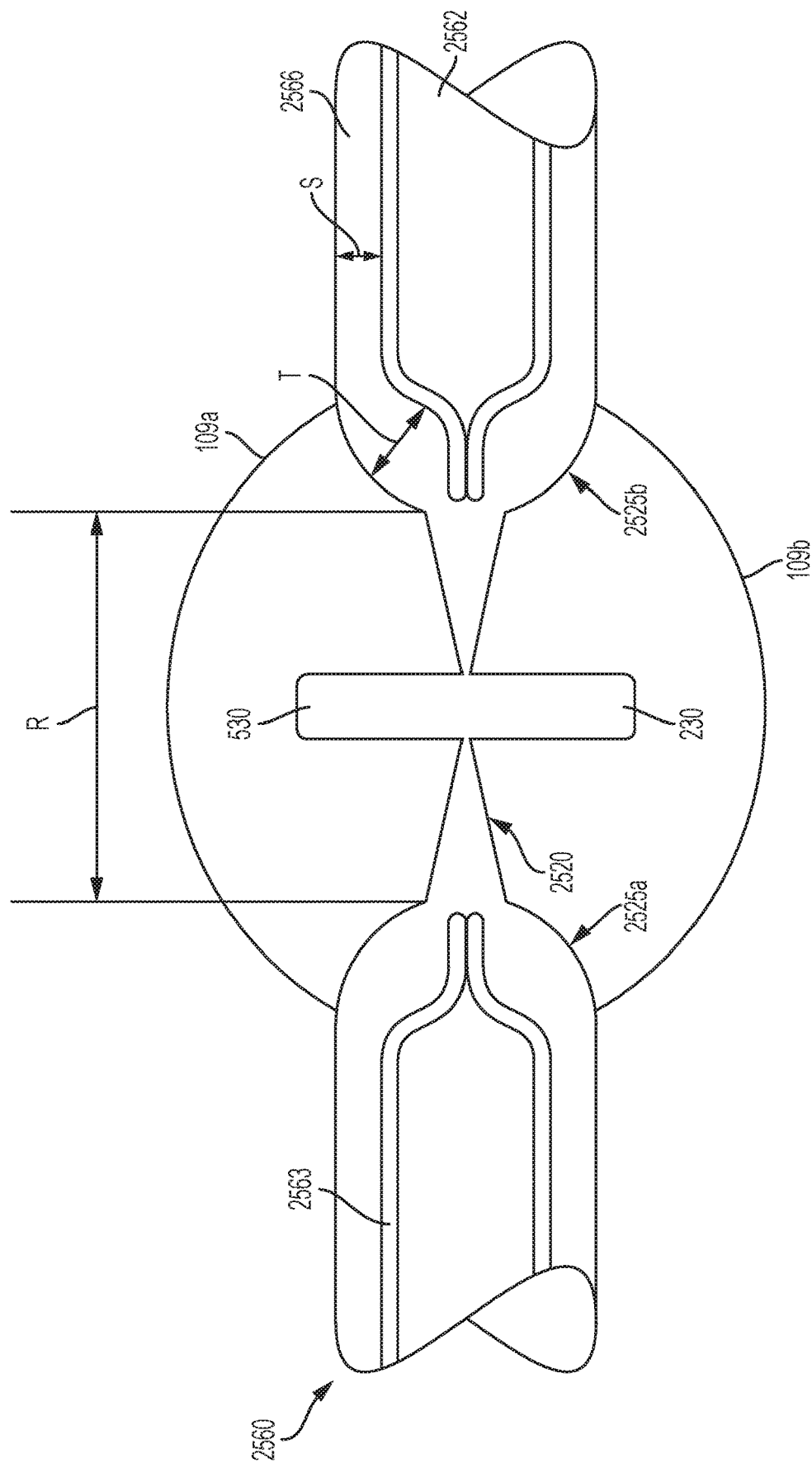
FIG. 25 is a cross-sectional view of a second aspect of a blood vessel compressed between the first jaw and the second jaw of the end effector depicted in FIG. 24.

FIG. 25 depicts the results of compressing and cauterizing a blood vessel 2560 between the jaw members illustrated in FIG. 24. In the aspect depicted in FIG. 25, a blood vessel 2560 may comprise a lumen 2562, a tunica media 2563, and an adventitia 2566. When the blood vessel 2560 is compressed between the first jaw member and the second jaw member, a compression zone R is created in an interior space between the jaw members. The compression zone R may include a combination of the first tapered space 2424a and the second tapered space 2424b, as depicted in FIG. 24. Upon the application of the electrical energy to the jaw members, the tissue of the vessel 2560 may be heated to form a coagulum. Without being bound by theory, the coagulum may be subjected to plastic flow forces directed by the taper 2520 of the jaw members within the compression zone R. As a result, the coagulum, along with the tunica media 2563, may flow from the compression zone R into mold zones 2525a,b. It may be noted that mold zones 2525a,b in FIG. 25 correspond to mold zones 2425a,b in FIG. 24. Because excess tissue, as coagulum, may accumulate in the mold zones 2525a,b, the thickness T of the adventitia in the mold zone 2525a,b may be greater than the normal thickness S of the adventitia of the blood vessel 2560. The sealed blood vessel 2560 may be cut by means of a reciprocating knife operating within the knife channels 530 and 230. The resulting seal may include the thickened portion of the blood vessels 2560 created by the coagulum being molded in the mold zones 2525a,b. In this manner, the blood vessel seals may be fabricated with greater reproducibility, consistency, and predictability.

As depicted in FIGS. 22, 23, and 25, blood vessels that may be subjected to cauterization procedures using a surgical instrument having jaw members as depicted herein may have a complex structure including multiple layers. As disclosed above, such blood vessels may include arteries and veins comprising an intima, a tunica media, and an adventitia (along with venous valves). However, it should be recognized that blood vessels of any size and structure may be compressed and sealed using the jaw members disclosed above. Such blood vessels may include, without limitation, arterioles, capillaries, and venules. Further, non-vascular tissue, including dermal tissue, muscle tissue, gastrointestinal tissue, and urinary tissue, may also be suitably cauterized and cut using a surgical instrument having such jaw members as discloses herein.

While various aspects herein have been illustrated by description of several aspects and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices (e.g. floppy disk, hard disk drive, Compact Disc (CD), Digital Video Disk (DVD), or digital tape). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components, and/or electrically interacting components, and/or electrically interactable components, and/or optically interacting components, and/or optically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered examples:

Example 1

An electrosurgical system comprising:
an RF current generator; a handle body; and
an end effector in mechanical communication with the handle body, the end effector comprising:
  a first jaw comprising a first electrode having a first electrode surface, wherein the first electrode is in electrical communication with a first terminal of the RF current generator; and
  a second jaw comprising a second electrode having a second electrode surface, wherein the second electrode is in electrical communication with a second terminal of the RF current generator;
  wherein the first jaw comprises at least one feature configured to apply an amount of a compressive force to a tissue compressed between the at least one feature and the second electrode surface that differs from an amount of a compressive force applied to the tissue compressed between the first electrode surface and the second electrode surface when the first jaw is placed in a proximate position to the second jaw, and
  and wherein the second electrode is a planar surface.

Example 2

The electrosurgical system of Example 1, wherein the at least one feature comprises an at least one longitudinal channel disposed in the first electrode.

Example 3

The electrosurgical system of any one of Examples 1 through 2, wherein the at least one feature comprises an at least one transverse channel disposed in the first electrode.

Example 4

The electrosurgical system of any one of Examples 1 through 3, wherein the second electrode is disposed on an insulating layer.

Example 5

The electrosurgical system of Example 4, further comprising a plurality of insulating pads wherein each of the plurality of insulating pads has a surface co-planar with the second electrode surface;
wherein the at least one feature comprises a plurality of raised bosses extending from and in electrical communication with the first electrode; and
wherein at least one of the plurality of raised bosses is configured to engage at least one of the plurality of insulating pads when the first jaw is placed in the proximate position to the second jaw.

Example 6

The electrosurgical system of Example 5, wherein the at least one feature further comprises an at least one longitudinal ridge extending from and in electrical communication with the first electrode and wherein the plurality of raised bosses extend from a surface of the at least one longitudinal ridge.

Example 7

The electrosurgical system of Example 6, wherein the at least one feature further comprises an at least one longitudinal channel disposed in the first electrode.

Example 8

The electrosurgical system of Example 5, wherein the at least one feature further comprises an at least one transverse ridge extending from and in electrical communication with the first electrode and wherein the plurality of raised bosses extend from a surface of the at least one transverse ridge.

Example 9

The electrosurgical system of Example 8, wherein the at least one feature further comprises an at least one transverse channel disposed in the first electrode.

Example 10

The electrosurgical system of any one of Examples 1 through 9, wherein the second jaw is movable with respect to the first jaw when a force is applied to the end effector.

Example 11

The electrosurgical system of any one of Examples 1 through 10, wherein the first jaw is movable with respect to the second jaw when a force is applied to the end effector.

Example 12

An end effector for an electrosurgical device, the end effector comprising:
a first jaw comprising a first electrode having a first electrode surface, in which the first electrode is configured to be in electrical communication with a first terminal of an RF current generator; and
a second jaw comprising a second electrode having a second electrode surface, in which the second electrode is configured to be in electrical communication with a second terminal of the RF current generator;
in which the first jaw comprises at least one feature configured to apply an amount of a compressive force to a tissue compressed between the at least one feature and the second electrode surface that differs from an amount of a compressive force applied to the tissue compressed between the first electrode surface and the second electrode surface by the first electrode when the first jaw is placed in a proximate position to the second jaw, and
in which the second electrode is a planar surface.

Example 13

The end effector of Example 12, wherein the at least one feature is configured to apply an amount of a compressive force to the tissue compressed between the at least one feature and the second jaw that is greater than the amount of a compressive force applied to the tissue compressed between the first electrode surface and the second electrode surface by the first electrode when the first jaw is placed in the proximate position to the second jaw.

Example 14

The end effector of any one of Examples 12 through 13, wherein the at least one feature comprises at least one longitudinal ridge extending from and in electrical communication with the first electrode.

Example 15

The end effector of any one of Examples 12 through 14, wherein the at least one feature comprises at least one transverse ridge extending from and in electrical communication with the first electrode.

Example 16

The end effector of any one of Examples 12 through 15, wherein the at least one feature is configured to apply an amount of a compressive force to the tissue compressed between the a least one feature and the second electrode surface that is less than the amount of a compressive force applied to the tissue compressed between the first electrode surface and the second electrode surface by the first electrode when the first jaw is placed in the proximate position to the second jaw.

Example 17

The end effector of Example 16, wherein the at least one feature comprises at least one longitudinal channel disposed in the first electrode.

Example 18

The end effector of Example 16, wherein the at least one features comprises at least one transverse channel disposed in the first electrode.

Example 19 wherein at least one feature is configured to apply an amount of a compressive force to the tissue compressed between the at least one feature and the second electrode surface that is greater than the amount of a compressive force applied to the tissue compressed between the first electrode surface and the second electrode surface by the first electrode when the first jaw is placed in the proximate position to the second jaw, and
wherein at least a second feature is configured to apply an amount of a compressive force to the tissue compressed between the at least second feature and the second electrode surface that is less than the amount of a compressive force applied to the tissue compressed between the first electrode surface and the second electrode surface by the first electrode when the first jaw is placed in the proximate position to the second jaw.

Example 20

The end effector of any one of Examples 12 through 19, wherein the second electrode is disposed on an insulating layer.

Example 21

The end effector of Example 20, further comprising at least one insulating pad wherein the at least one insulating pad has a surface co-planar with the second electrode;
wherein the at least one feature comprises at least one raised boss extending from and in electrical communication with the first electrode; and
wherein the at least one raised boss is configured to engage the at least one insulating pad when the first jaw is placed in the proximate position to the second jaw.

Example 22

The end effector of Example 21, wherein the at least one feature further comprises at least one longitudinal ridge extending from and in electrical communication with the first electrode and wherein the at least one raised boss extends from a surface of the at least one longitudinal ridge.

Example 23

The end effector of any one of Examples 21 through 22, wherein the at least one feature further comprises at least one transverse ridge extending from and in electrical communication with the first electrode and wherein the at least one raised boss extends from a surface of the at least one transverse ridge.

Example 24

The end effector of any one of Examples 12 through 23, wherein the second jaw is movable with respect to the first jaw.

Example 25

The end effector of any one of Examples 1 through 11, wherein the first jaw is movable with respect to the second jaw.

What is claimed is:

1. An electrosurgical system comprising:
   an RF current generator;
   a handle body; and
   an end effector in mechanical communication with the handle body, the end effector comprising:
   a first jaw comprising a first electrode having a first electrode surface, wherein the first electrode is in electrical communication with a first terminal of the RF current generator; and
   a second jaw comprising a second electrode having a second electrode surface, wherein the second electrode is in electrical communication with a second terminal of the RF current generator;
   wherein:
   the first jaw comprises at least one feature configured to apply an amount of a compressive force to a tissue compressed between the at least one feature and the second electrode surface that differs from an amount of a compressive force applied to the tissue compressed between the first electrode surface and the second electrode surface when the first jaw is placed in a proximate position to the second jaw;
   the at least one feature comprises at least one raised longitudinal ridge extending from and in electrical communication with the first electrode to create a first raised level above the first electrode;
   the at least one feature comprises a plurality of raised bosses positioned on the at least one raised longitudinal ridge and extending from and in electrical communication with the first electrode, the plurality of raised bosses being positioned on the at least one raised longitudinal ridge creating a second raised level above the first electrode that is higher than the first raised level; and
   the second electrode surface is a planar surface.

2. The electrosurgical system of claim 1, wherein the at least one feature further comprises at least one longitudinal channel disposed in the first electrode.

3. The electrosurgical system of claim 1, wherein the at least one feature further comprises at least one transverse channel disposed in the first electrode.

4. The electrosurgical system of claim 1, wherein the second electrode is disposed on an insulating layer.

5. The electrosurgical system of claim 4, further comprising a plurality of insulating pads wherein each of the plurality of insulating pads has a surface co-planar with the second electrode surface and wherein at least one of the plurality of raised bosses is configured to engage at least one of the plurality of insulating pads when the first jaw is placed in the proximate position to the second jaw.

6. The electrosurgical system of claim 5, wherein the at least one feature further comprises at least one transverse ridge extending from and in electrical communication with the first electrode and wherein the plurality of raised bosses extend from a surface of the at least one transverse ridge.

7. The electrosurgical system of claim 6, wherein the at least one feature further comprises at least one transverse channel disposed in the first electrode.

8. The electrosurgical system of claim 1, wherein the second jaw is movable with respect to the first jaw when a force is applied to the end effector.

9. The electrosurgical system of claim 1, wherein the first jaw is movable with respect to the second jaw when a force is applied to the end effector.

10. An end effector for an electrosurgical device, the end effector comprising:
    a first jaw comprising a first electrode having a first electrode surface, wherein the first electrode is configured to be in electrical communication with a first terminal of an RF current generator; and
    a second jaw comprising a second electrode having a second electrode surface, wherein the second electrode is configured to be in electrical communication with a second terminal of the RF current generator;
    wherein:
    the first jaw comprises at least one feature configured to apply an amount of a compressive force to a tissue compressed between the at least one feature and the second electrode surface that differs from an amount of a compressive force applied to the tissue compressed between the first electrode surface and the second electrode surface by the first electrode when the first jaw is placed in a proximate position to the second jaw;
    the at least one feature comprises a first raised longitudinal ridge extending from and in electrical communication with the first electrode to create a first raised level above the first electrode;
    the at least one feature further comprises a second raised longitudinal ridge extending from and in electrical communication with the first electrode to create a second raised level above the first electrode that is higher than the first raised level;

the at least one feature further comprises a first raised boss positioned on the first raised longitudinal ridge and extending from and in electrical communication with the first electrode;

the at least one feature further comprises a second raised boss positioned on the second raised longitudinal ridge and extending from and in electrical communication with the first electrode; and the second electrode surface is a planar surface.

11. The end effector of claim 10, wherein the at least one feature is configured to apply the amount of the compressive force to the tissue compressed between the at least one feature and the second jaw that is greater than the amount of the compressive force applied to the tissue compressed between the first electrode surface and the second electrode surface by the first electrode when the first jaw is placed in the proximate position to the second jaw.

12. The end effector of claim 11, wherein the at least one feature comprises at least one transverse ridge extending from and in electrical communication with the first electrode.

13. The end effector of claim 10, wherein the at least one feature is configured to apply the amount of the compressive force to the tissue compressed between the at least one feature and the second electrode surface that is less than the amount of the compressive force applied to the tissue compressed between the first electrode surface and the second electrode surface by the first electrode when the first jaw is placed in the proximate position to the second jaw.

14. The end effector of claim 13, wherein the at least one feature comprises at least one longitudinal channel disposed in the first electrode.

15. The end effector of claim 13, wherein the at least one feature comprises at least one transverse channel disposed in the first electrode.

16. The end effector of claim 10, wherein the at least one feature is at least a first feature that is configured to apply the amount of the compressive force to the tissue compressed between the at least one feature and the second electrode surface that is greater than the amount of the compressive force applied to the tissue compressed between the first electrode surface and the second electrode surface by the first electrode when the first jaw is placed in the proximate position to the second jaw, and wherein the first jaw comprises at least a second feature that is configured to apply an amount of a compressive force to the tissue compressed between the at least second feature and the second electrode surface that is less than the amount of the compressive force applied to the tissue compressed between the first electrode surface and the second electrode surface by the first electrode when the first jaw is placed in the proximate position to the second jaw.

17. The end effector of claim 10, wherein the second electrode is disposed on an insulating layer.

18. The end effector of claim 17, further comprising at least one insulating pad wherein the at least one insulating pad has a surface co-planar with the second electrode surface;

wherein the at least one feature further comprises at least one third raised boss extending from and in electrical communication with the first electrode; and wherein the at least one third raised boss is configured to engage the at least one insulating pad when the first jaw is placed in the proximate position to the second jaw.

19. The end effector of claim 18, wherein the at least one feature further comprises at least one third longitudinal ridge extending from and in electrical communication with the first electrode and wherein the at least one third raised boss extends from a surface of the at least one third longitudinal ridge.

20. The end effector of claim 18, wherein the at least one feature further comprises at least one transverse ridge extending from and in electrical communication with the first electrode and wherein the at least one third raised boss extends from a surface of the at least one transverse ridge.

21. The end effector of claim 10, wherein the second jaw is movable with respect to the first jaw.

22. The end effector of claim 10, wherein the first jaw is movable with respect to the second jaw.

* * * * *